US006103727A

United States Patent [19]
Gangjee

[11] Patent Number: 6,103,727
[45] Date of Patent: Aug. 15, 2000

[54] PYRIMIDINE DERIVATIVES AND METHODS OF MAKING AND USING THESE DERIVATIVES

[75] Inventor: Aleem Gangjee, Allison Park, Pa.

[73] Assignee: Duquesne University of the Holy Ghost, Pittsburgh, Pa.

[21] Appl. No.: 09/435,401

[22] Filed: Nov. 5, 1999

Related U.S. Application Data

[62] Division of application No. 09/190,374, Nov. 12, 1998, which is a division of application No. 08/683,869, Jul. 19, 1996, Pat. No. 5,877,178, which is a continuation-in-part of application No. 08/660,023, Jun. 6, 1996, Pat. No. 5,939,420, which is a continuation-in-part of application No. 08/515,491, Aug. 15, 1995, Pat. No. 5,736,547, which is a division of application No. 08/304,044, Sep. 12, 1994, Pat. No. 5,508,281, which is a continuation-in-part of application No. 07/950,982, Sep. 23, 1992, Pat. No. 5,346,900, which is a continuation of application No. 07/829,519, Jan. 31, 1992, abandoned, which is a continuation of application No. 07/682,043, Apr. 8, 1991, abandoned.

[51] Int. Cl.[7] .................................................. A61K 31/505
[52] U.S. Cl. .......................... 514/258; 514/256; 514/257
[58] Field of Search ..................................... 514/258, 280

[56] References Cited

U.S. PATENT DOCUMENTS

| | | | |
|---|---|---|---|
| 3,904,624 | 9/1975 | Perronnet et al. ................... | 260/251 P |
| 4,996,206 | 2/1991 | Taylor et al. ........................... | 514/258 |
| 5,028,608 | 7/1991 | Taylor et al. ........................... | 514/258 |
| 5,248,775 | 9/1993 | Taylor et al. ........................... | 544/280 |
| 5,254,687 | 10/1993 | Taylor et al. ........................... | 544/280 |
| 5,344,932 | 9/1994 | Taylor ................................... | 544/280 |
| 5,346,900 | 9/1994 | Gangjee ................................. | 514/258 |
| 5,508,281 | 4/1996 | Gangjee ................................. | 514/258 |
| 5,877,178 | 3/1999 | Gangjee ................................. | 514/258 |

OTHER PUBLICATIONS

Hurlbert et al., "Studies on Condensed Pyrimidine Systems. XXIII. Synthesis of 2,4–Diaminopyrido[2,3–d]pyrimidines from β–Keto Esters", *J. Med. Chem.*, vol. 11, pp. 703–707 (1968).

Hurlbert et al., "Studies on Condensed Pyrimidine Systems. XXIV. The Condensation of 2,4,6–Triaminopyrimidine with Malondialdehyde Derivatives", *J. Med. Chem.*, vol. 11, pp. 708–710 (1968).

Hurlbert et al., "Studies on Condensed Pyrimidine Systems. XXV. 2,4–Diaminopyrido[2,3–d]pyrimidines. Biological Data", *J. Med. Chem.*, vol. 11, pp. 711–717 (1968).

Grivsky et al., "Synthesis and Antitumor Activity of 2,4–Diamino–6–(2,5–dimethoxybenzyl)–5–methylpyrido[2,3–d]pyrimidine", *J. Med. Chem.*, vol. 23, pp. 327–329 (1980).

Elslager et al., "Folate Antagonists. 20. Synthesis and Antitumor and Antimalarial Properties of Trimetrexate and Related 6–[(phenylamino)methyl]–2,4–quinazolinediamines", *J. Med. Chem.*, vol. 26, pp. 1753–1760 (1983).

Piper et al., "Synthesis and Antifolate Activity of 5–Methyl–5–deaza Analogues of Aminopterin, Methotrexate, Folic Acid, and $N^{10}$–Methylfolic Acid", *J. Med. Chem.*, vol. 29, pp. 1080–1087 (1986).

Werbel et al., "Synthesis and Antimalarial Activity of a Series of 2,4–Diamino–6–[(N–alkylanilino)methyl]quinazolines", *J. Heterocyclic Chem.*, vol. 24, pp. 345–349 (1987).

Gangjee et al., "Classical and Nonclassical Furo[2,3–d]pyrimidines as Novel Antifolates: Synthesis and Biological Activities", *J. Med. Chem.*, vol. 37, No. 8, pp. 1169–1176 (1994).

Gangjee et al., "Novel 2,4–Diamino–5–Substituted–pyrrolo[2,3–d]pyrimidines as Classical and Nonclassical Antifolate Inhibitors of Dihydrofolate Reductases", *J. Med. Chem.*, vol. 38, No. 12, pp. 2158–2165 (1995).

Gangjee et al., "Effect of Bridge Region Variation on Antifolate and Antitumor Activity of Classical 5–Substituted 2,4–Diaminofuro[2,3–d]pyrimidines", *J. Med. Chem.*, vol. 38, No. 19, pp. 3798–3805 (1995).

Gangjee et al., "5–Arylthio–Substituted 2–Amino–4–oxo–6–methylpyrrolo[2,3–d]pyrimidine Antifolates as Thymidylate Synthase Inhibitors and Antitumor Agents", *J. Med. Chem.*, vol. 38, No. 22, pp. 4495–4502 (1995).

Nishimura et al., *Chem. Abstracts*, C.A. vol. 99:70481a (1983).

*Primary Examiner*—Mukund J. Shah
*Assistant Examiner*—Pavanaram K Sripad
*Attorney, Agent, or Firm*—Diane R. Meyers; Eckert Seamans Cherin & Mellott, LLC

[57] ABSTRACT

This invention discloses compounds, and pharmaceutically acceptable salts thereof, useful in therapeutically and/or prophylactically treating patients with an illness. Such illnesses include cancer, and secondary infections caused by *Pneumocystis carinii* and *Toxoplasmosis gondii* in immunocompromised patients. The compounds themselves, methods of making these compounds, and methods of using these compounds are all disclosed.

12 Claims, 18 Drawing Sheets

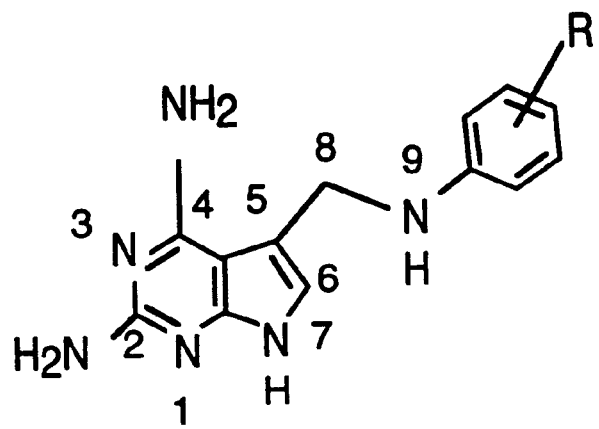
1: R=3',4',5' -(OCH3)3
2: R=3',4' -(OCH3)2
3: R=4' -(OCH3)
4: R=2',5' -(OCH3)2
5: R=2',5' -(OC2H5)2
6: R=3',4'-(Cl)2
7: R=2',3' -(CH)4
8: R=H
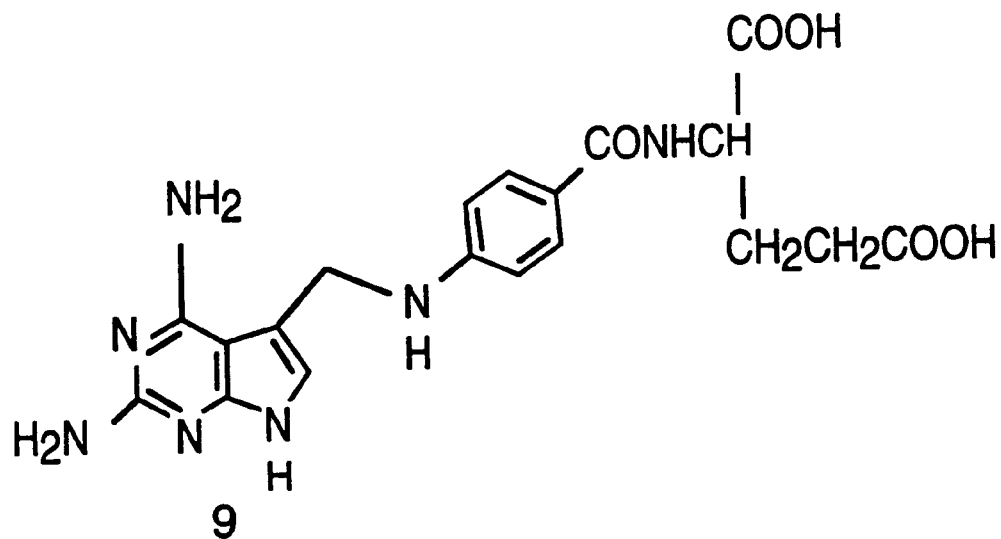
FIG. 2

(A): Raney Ni/HCOOH; (B): NaBH3; (C): 30% HBr-AcOH; (D): DMF; (E): NaH/DMF

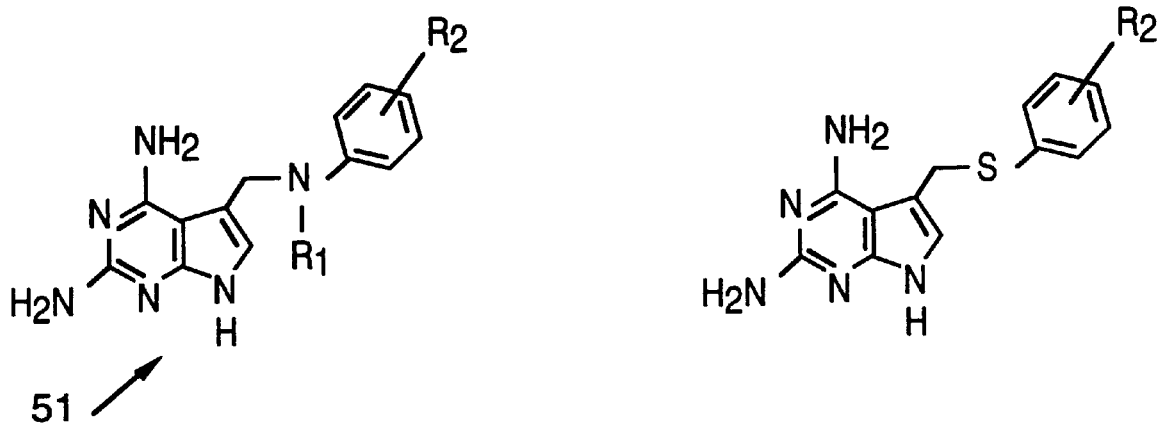
R₁ = H: R₂ =
51a : 2', 5' - (OCH₃)₂
51b : 3', 4' - (Cl)₂
51c : 2', 3' - (CH)₄
R₁ = CH₃: R₂ =
52 : 2', 5' - (OCH₃)₂
53 : 3', 4' - (Cl)₂
54 : 2', 3' - (CH)₄
R =
55 : 3', 4' - (OCH₃)₂
56 : 3', 4' - (Cl)₂
57 : 2', 3' - (CH)₄
58 : 3', 4' - (CH)₄
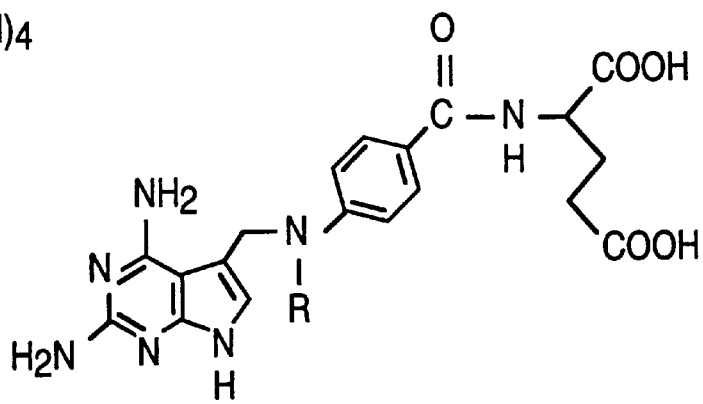
R =
59 : H
60 : CH₃
FIG. 9

FIG. 10g  R=H
FIG. 10h  R=3,4,5 trimethoxy
FIG. 10i  R=3,5 dimethoxy
FIG. 10j  R=2,4 dichloro
FIG. 10k  R=3,4 dichloro
FIG. 10l  R=2,6 dichloro
FIG. 10m  R=-CONHCH2CH2COOH
                    |
                   COOH $R_1$ = H, $R_2$ = 3',4'-diOMe
$R_1$ = H, $R_2$ = H
$R_1$ = H, $R_2$ = 2',5'-diOMe
$R_1$ = H, $R_2$ = 4'-Cl
$R_1$ = H, $R_2$ = 2'-OMe
$R_1$ = H, $R_2$ = 4'-OMe
$R_1$ = H, $R_2$ = 3',4',5'-triOMe
$R_1$ = $CH_3$, $R_2$ = 3',4',5'-triOMe
$R_1$ = $CH_3$, $R_2$ = 2',5'-diOMe
$R_1$ = $CH_3$, $R_2$ = 3',4'-diOMe
$R_1$ = $CH_3$, $R_2$ = 3',4',5'-triOMe
$R_1$ = $CH_3$, $R_2$ = H
$R_1$ = H, $R_2$ = 3',4'-$C_4H_4$
$R_1$ = $CH_3$, $R_2$ = 3',4'-$C_4H_4$
$R_1$ = $CH_3$, $R_2$ = 2',3'-$C_4H_4$

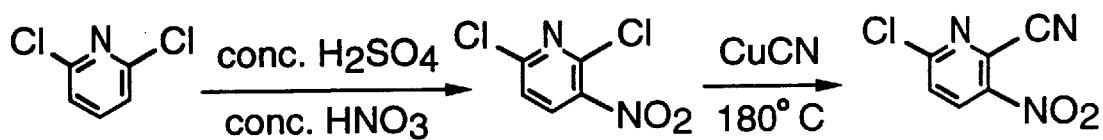
FIG. 12a
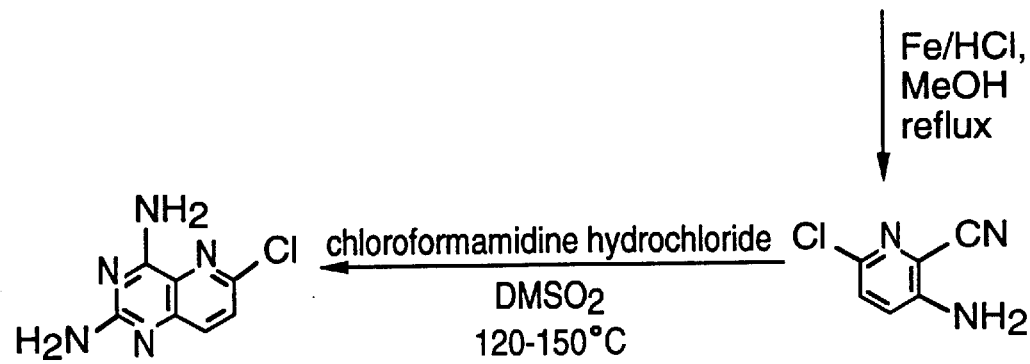
FIG. 12c
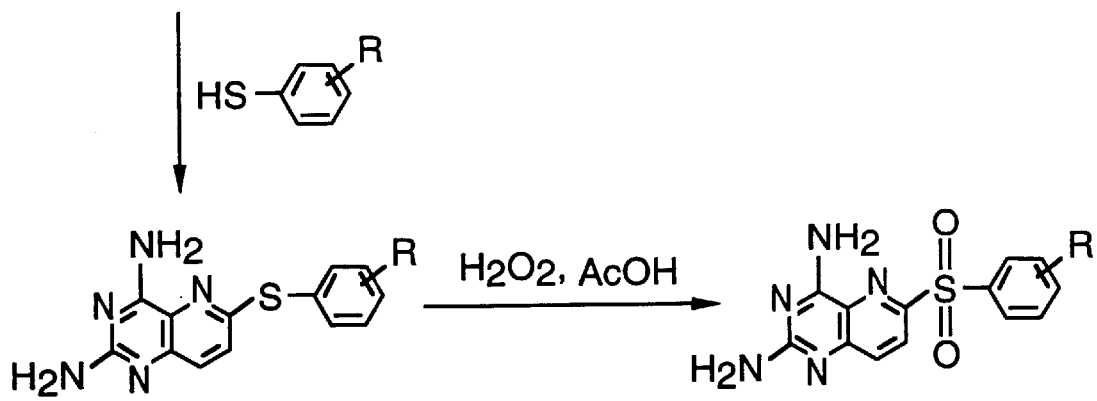
FIG. 12d
FIG. 12e
FIG. 12f R=4'-OMe
FIG. 12g R=3',4'-OMe
FIG. 12h R=2'-OMe
FIG. 12i R=4'-OMe
FIG. 12j R=3',4'-OMe
FIG. 12k R=2'-OMe

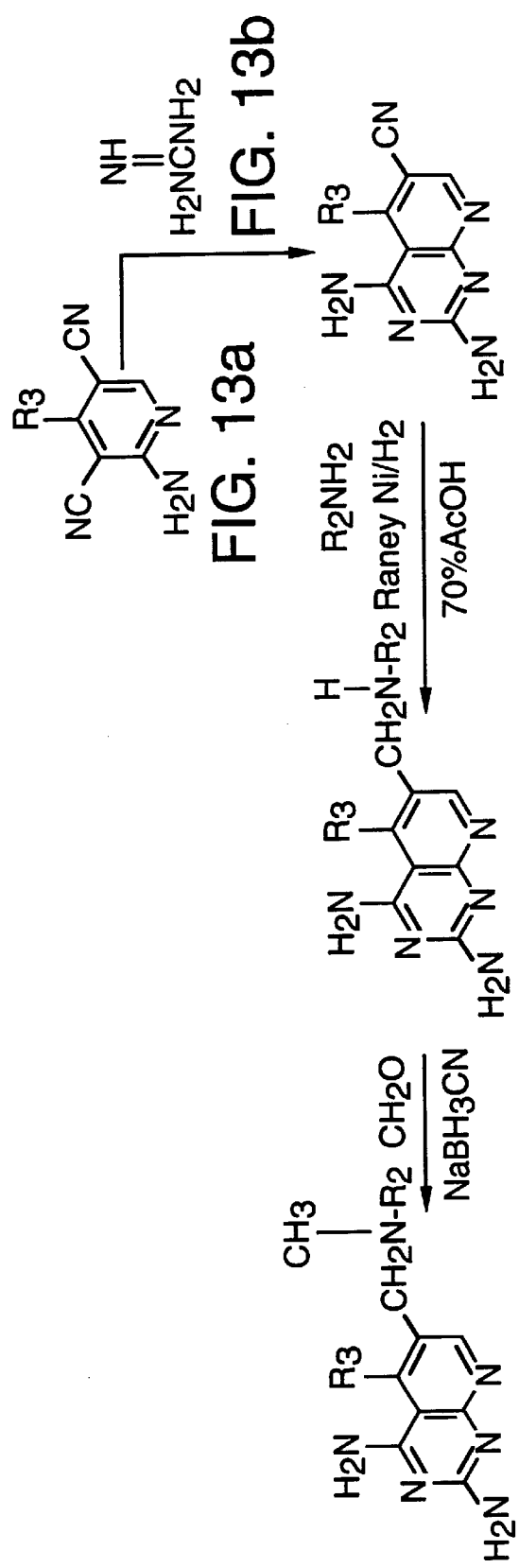

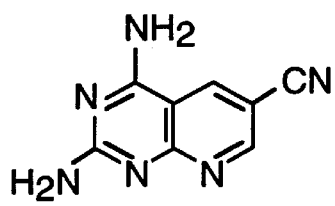
FIG. 14a
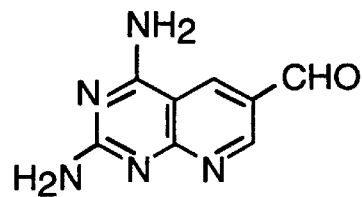
FIG. 14b
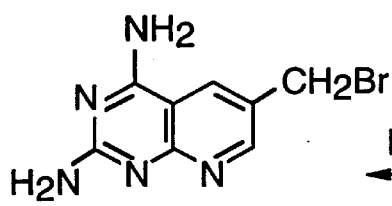
FIG. 14d
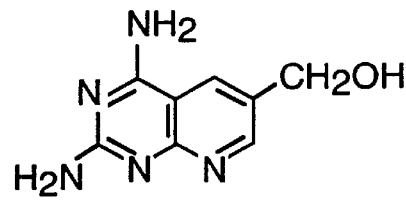
FIG. 14c
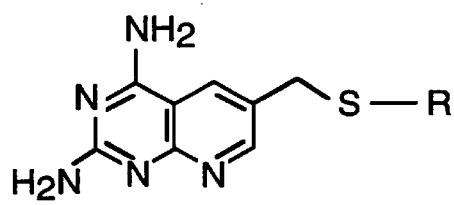
FIG. 14e  R = Phenyl
FIG. 14f  R = Napthylene

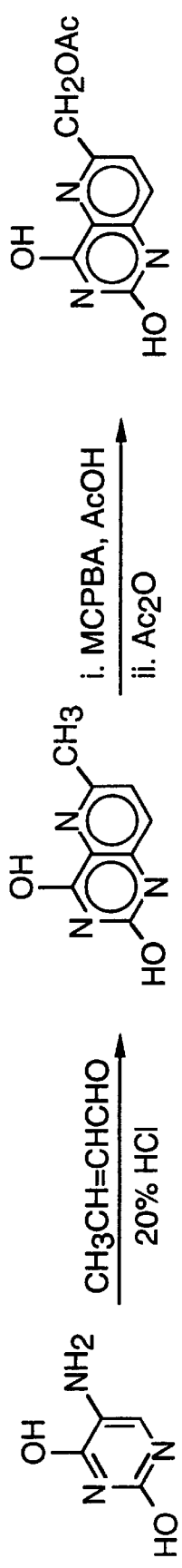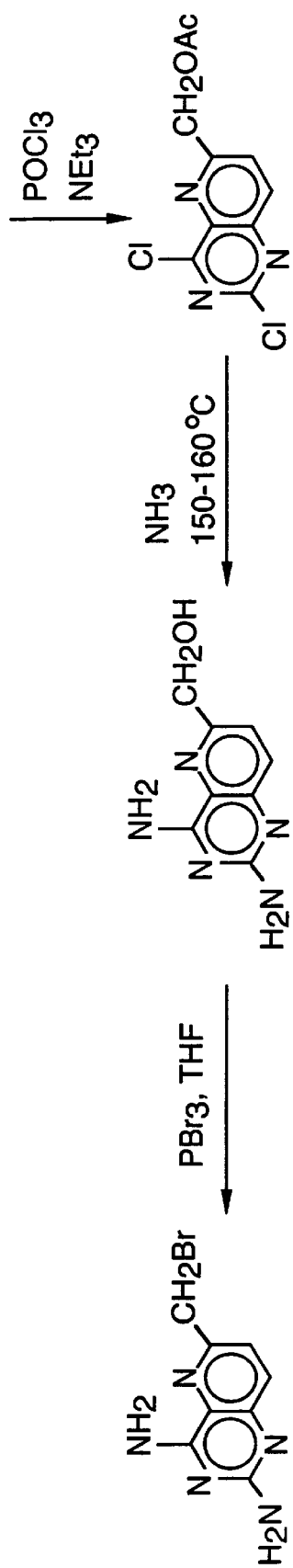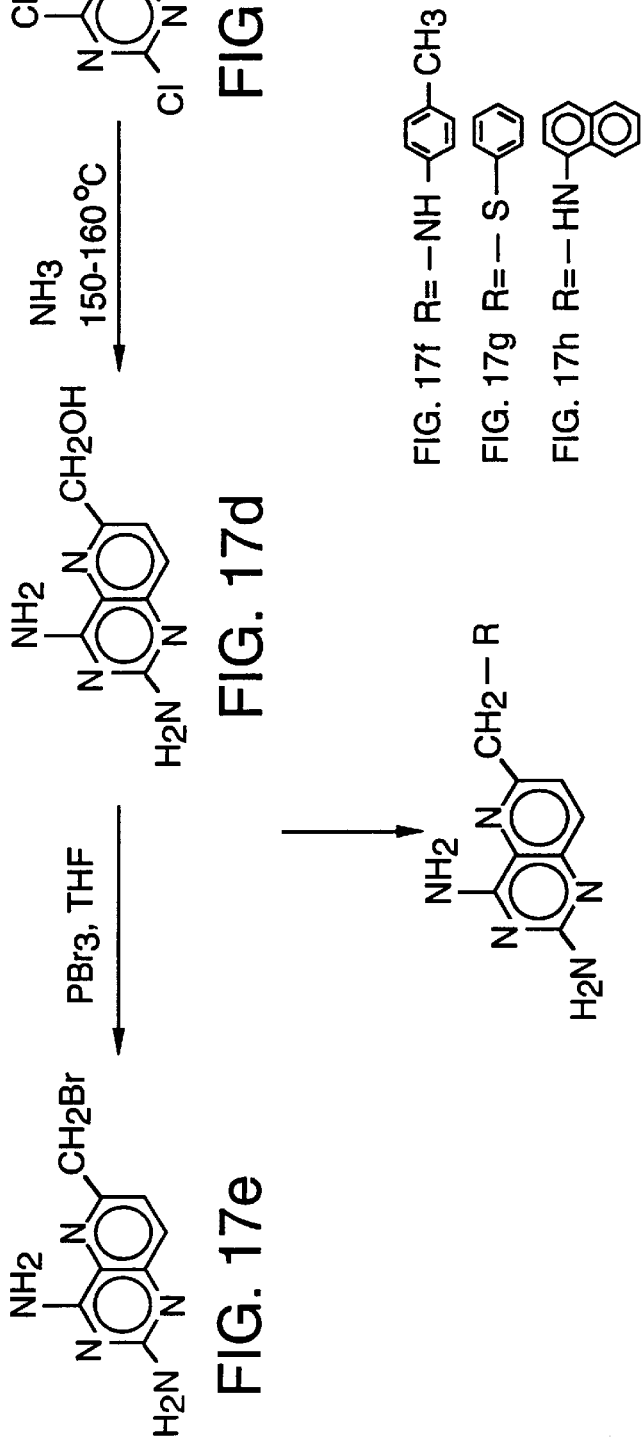
FIG. 17a
FIG. 17b
FIG. 17c
FIG. 17d
FIG. 17e
FIG. 17f R=—NH—⟨C6H4⟩—CH3
FIG. 17g R=—S—⟨C6H5⟩
FIG. 17h R=—HN—⟨naphthyl⟩

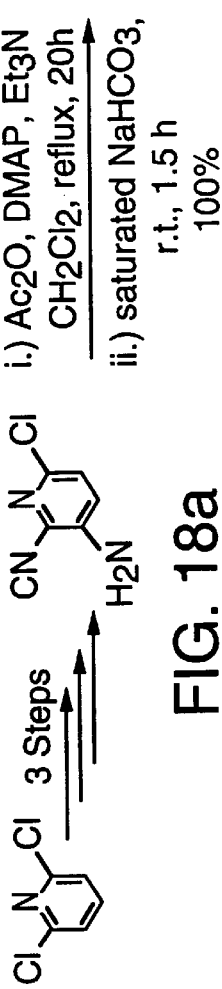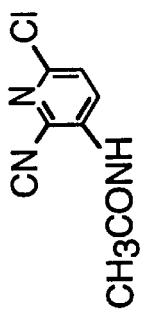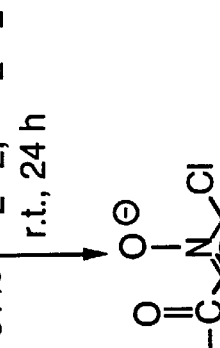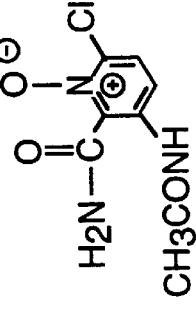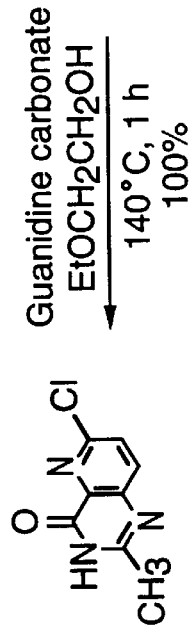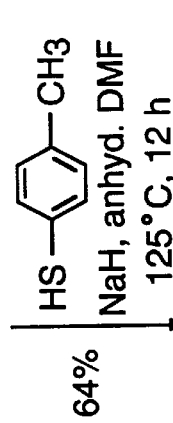
FIG. 18a FIG. 18b FIG. 18c FIG. 18d FIG. 18e

PYRIMIDINE DERIVATIVES AND METHODS OF MAKING AND USING THESE DERIVATIVES

This is divisional of U.S. application Ser. No. 09/190,374, filed Nov. 12, 1998, pending which is a divisional of U.S. application Ser. No. 08/683,869, filed Jul. 19, 1996 now U.S. Pat. No. 5,877,178 a continuation-in-part application of U.S. application Ser. No. 08/660,023 filed Jun. 6, 1996, U.S. Pat. No. 5,939,420 which is a continuation-in-part application of U.S. application Ser. No. 08/515,491 filed Aug. 15, 1995, U.S. Pat. No. 5,736,547 which is a divisional of U.S. application Ser. No. 08/304,044, filed Sep. 12, 1994 now U.S. Pat. No. 5,508,281, which is a continuation-in-part of U.S. application Ser. No. 07/950,982 filed Sep. 23, 1992, now U.S. Pat. No. 5,346,900, which is a continuation of U.S. application Ser. No. 07/829,519 filed Jan. 31, 1992, now abandoned, which in turn is a continuation of U.S. application Ser. No. 07/682,043 filed Apr. 8, 1991, now abandoned.

The invention described herein was made in the course of work supported in part by the National Institutes of General Medical Sciences, Grant No. 1-RO1-GM-40998 from the National Institutes of Health, U.S. Department of Health and Human Services. The Government has certain rights in this invention.

BACKGROUND OF THE INVENTION

1. Field of the Invention

This invention relates to pyrimidine derivative compounds and pharmaceutically acceptable salts thereof. More specifically, this invention relates to furo[2,3-d]pyrimidines, pyrrolo[2,3-d]pyrimidines, pyrrolo[3,2-d]pyrimidines, pyrrolo[3,4-d]pyrimidines, thieno[2,3-d]pyrimidines, cyclopentapyrimidines, cyclopenta[d]pyrimidines, pyrido[2,3-d]pyrimidines and pyrido[3,2-d]pyrimidines. These compounds have been found useful in resisting and treating *Pnewnocystis carinii* and *Toxoplasmosis gondii* infections in immunocompromised patients, such as, for example, patients with autoimmune deficiency syndrome (AIDS). These compounds are also useful as potential antitumor, antibiotic, antimalarial, antifungal or antiprotozoal agents, or as synergistic agents when used with sulfonamides and may require the use of leucovorin rescue. These compounds are also useful as antitumor agents in cancer patients. Methods of preparing and using these compounds are also provided.

2. Description of the Background Art

Various pyrimidine systems, such as the pyrido[2,3-d] pyrimidine ring system, have been studied due to their involvement in the inhibition of dihydrofolate reductase (DHFR) enzymes activity. The pyrimidine derivatives disclosed herein function as DHFR inhibitors. Because DHFR reduces dihydrofolate to tetrahydrofolate, inhibition of DHFR deprives the cell of tetrahydrofolate, without which the cell cannot produce 5,10-methylenetetrahydrofolate. 5,10-Methylenetetrahydrofolate is essential for cell growth. The inhibition of DHFR by the compounds, and pharmaceutically acceptable salts thereof, of this invention results in the inhibition of DNA synthesis and leads to cell death. Methotrexate (MTX), trimetrexate (TMQ), piritrexim (PTX) and other folic acid analogues function as inhibitors of cell growth by similar mechanisms involving the inhibition of dihydrofolate reductase.

The pyrimidine derivatives disclosed herein also function as thymidylate synthase (TS) inhibitors. TS, along with DHFR, forms part of the systems responsible for the synthesis of deoxythymidylate (dTMP) from deoxyuridylate (dUMP). TS catalyzes the sole de novo synthesis of dTMP from dUMP. Inhibition of TS, therefore, deprives the cell of thymidine, which is an essential constituent of DNA. Typically, the compounds as described herein where X and Y are both $NH_2$ or where X is $NH_2$ and Y is H or $CH_3$ and will function as DHFR inhibitors, and compounds where X is OH and Y is $NH_2$, H, or $CH_3$ will function as TS inhibitors, although the inventor does not wish to be bound by this generality.

Drugs useful for the reduction of cancerous cells are also known.

Elslager, Edward F., et al., "Folate Antagonists. 20. Synthesis and Antitumor and Antimalarial Properties of Trimetrexate and Related 6-[(Phenylamino)methyl]-2,4-quinazolinediamines" *J. Med. Chem.*, Vol. 26 pp. 1753–1760 (1983)), discloses the preparation of quinazolinediamines. This article states that the quinazolinediamines exhibit potent antimalarial, antibacterial and antitumor activity.

Methods of synthesizing diaminopyrido[2,3-d] pyrimidines having various substituents are known. See Hurlbert, B. S., et al., "Studies on Condensed Pyrimidine Systems. XXIII. Synthesis of 2,4-Diaminopyrido[2,3-d] pyrimidines from 6-Keto Esters", *J. Med. Chem.*, Vol. 11, pp. 703–707 (1968), and Hurlbert, B. S., and Valenti, B. F., "Studies on Condensed Pyrimidine Systems. XXIV. The Condensation of 2,4,6-Triaminopyridimine with Malondialdehyde Derivatives", *J. Med. Chem.*, Vol. 11, pp. 708–710 (1968).

Hurlbert, B. S., et al., "Studies on Condensed Pyrimidine Systems. XXV. 2,4-d]Diaminopyrido[2,34pyrimidines. Biological Data", *J. Med. Chem.*, Vol. 11, pp. 711–717 (1968), discloses the antimicrobial activities of several subgroups of pyridopyrimidines. This article states that 2,4-diaminopyrido[2,3-d]pyrimidines bearing alkyl and aralkyl substituents in the pyrimidine moiety are inhibitors of dihydrofolate reductase having antibacterial and antiprotozoal activity and that these compounds potentiate sulfonamides.

Grivsky, E. M., et al., "Synthesis and Antitumor Activity of 2,4-Diamino-6-(2,5Sdimethoxybenzyl)-5-methylpyrido [2,3-d]pyridimine", *J. Med. Chem.*, Vol. 23, pp. 327–329 (1980), discloses the synthesis of 2,4-diamino-6-(2,5-dimethoxybenzyl)-5-methylpyrido[2,3-d]pyridimine (BW301U,7). This article states that BW301U,7 is as effective as methotrexate as an inhibitor of dihydrofolate reductase purified from human leukemic cells and, in contrast to metoprine, has minimal activity as an inhibitor of histamine metabolism.

Werbel, Leslie, M., et al., "Synthesis and Antimalarial Activity of a Series of 2,4-Diamino-6-[(N-alkylanilino) methyl]quinazolines [1,2]", *J. Heterocyclic Chem.*, Vol. 24, pp. 345–349 (1987), discloses the synthesis of N6 substituted quinazoline dihydrofolate reductase inhibitors. This article states that these analogs demonstrate substantial activity against Plasmodium berghei infections in mice.

Piper, J. R., et al., "Syntheses and Antifolate Activity of 5-Methyl-5-deaza Analogues of Aminopterin, Methotrexate, Folic Acid, and $N^{10}$-Methylfolic Acid", *J. Med. Chem.*, Vol. 29, pp. 1080–1087 (1986), discloses that 5-methyl- 5-deaza analogues of aminopterin and methotrexate are much more growth inhibitory than methotrexate.

Pyrido [2,3-d] and [3,2-d] pyrimidines are also disclosed in U.S. Pat. Nos. 5,346,900 and 5,508,281, and co-pending application Ser. No. 08/515,491, all of which are hereby expressly incorporated by reference.

Pyrrolo[2,3d]pyrimidines are disclosed by Gangjee et al. in "Novel 2,4-diamino-5-substituted-pyrrolo[2,3-d] pyrimidines As Classical and Non-Classical Antifolate Inhibitors of Dihydrofolate Reducteses", *J. Med. Chem.*, Vol. 38, pp. 2158–2165 (Jun. 6, 1995).

Gangjee, A., et al., "Classical and Non-Classical Furo[2,3-d]-Pyrimidines As Novel Antifolates: Synthesis and Biological Activities", *J. Med. Chem.*, Vol. 37, pp. 1169–1176 (1994), discloses the furo[2,3-d]pyrimidines.

In spite of the art discussed above, there remains a very real and substantial need for compounds that are more active and more selective than known compounds at resisting and treating infections caused by *Pnewnocystis carinii* and *Toxoplasmosis gondii* in immunocompromised patients, reducing the tumor size and/or the number of cancerous cells in cancer patients, and for methods of preparing and using such compounds.

SUMMARY OF THE INVENTION

The present invention has met the above described need. The present invention provides pyrrolo[2,3-d]pyrimidine compounds, and pharmaceutically acceptable salts thereof, having the formula (1):

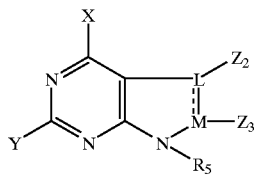

(1)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_2$ and $Z_3$ are different and are selected from the group consisting of $R_4$ and

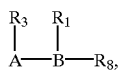

where $Z_2$ is $R_4$ when $Z_3$ is

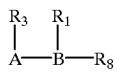

and $Z_2$ is

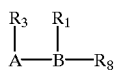

when $Z_3$ is $R_4$;

wherein A is selected from the group consisting of CH and zero;

wherein B is selected from the group consisting of CH, nitrogen, N—$CH_2$, $CH_2$—N, $CH_2$—$CH_2$, oxygen, sulfur, sulfoxide, sulfone and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_3$ is selected from the group consisting of hydrogen, a lower alkyl group and zero, and $R_3$ is zero when A is zero;

wherein $R_4$ is selected from the group consisting of hydrogen and a lower alkyl group;

wherein $R_5$ is selected from the group consisting of hydrogen and a lower alkyl group;

wherein $R_8$ is selected from the group consisting of naphthyl, mono-, di- and tri-substituted naphthyl, thionaphthyl, thiophenyl and hydroxyphenyl when $R_1$ is hydrogen and $R_4$ is hydrogen;

wherein $R_8$ is selected from the group consisting of phenyl, mono-, di- and tri-substituted phenyl, naphthyl, mono-, di- and tri-substituted naphthyl, pyridine and p-aroyl-L-glutamate when $R_1$ is a lower alkyl group and $R_4$ is hydrogen;

wherein $R_8$ is selected from the group consisting of pyridine, phenyl, mono-, di- and tri-substituted phenyl, naphthyl, and mono-, di- and tri-substituted naphthyl and p-aroyl-L-glutamate when $R_1$ is zero;

wherein $R_8$ is selected from the group consisting of phenyl, mono-, di- and tri-substituted phenyl, naphthyl, mono-, di- and tri-substituted naphthyl and p-aroyl-L-glutamate when $R_1$ is hydrogen and $R_4$ is a lower alkyl group; and wherein $R_8$ is not p-benzoyl-L-glutamate or pyridine when X is OH, A is zero, B is sulfur, $R_4$ is methyl and $R_5$ is hydrogen, and $R_8$ is not p-benzoyl-L-glutamate when X is OH, A is CH, B is CH, $R_4$ is hydrogen and $R_5$ is hydrogen; and wherein each lower alkyl group is independently selected from the group consisting of lower alkyl groups having from 1 to 6 carbons.

The present invention also provides methods of synthesizing pyrrolo-[2,3d]pyrimidine compounds, and pharmaceutically acceptable salts thereof, having the formula (2):

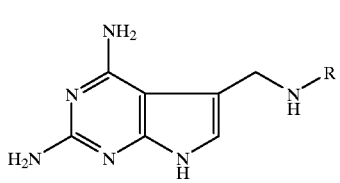

(2)

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen; and wherein each lower alkyl group is independently selected from the group consisting of lower alkyl groups having from about 1 to 6 carbons, comprising the steps of:

a) debrominating a pyrrole;
b) fusing the product of step a) with an amidine;
c) condensing the product of step b) with a nucleophile;
d) reducing the product of step c); and
e) purifying the compounds of step d).

The present invention also provides furo[2,3-d] pyrimidine compounds, and pharmaceutically acceptable salts thereof, having the formula (4):

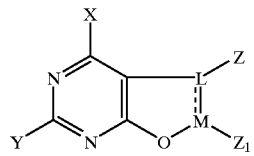

(4)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

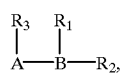

where Z is $R_4$ when $Z_1$ is

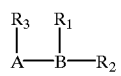

and Z is

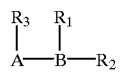

when $Z_1$ is $R_4$;

wherein A is selected from the group consisting of CH and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl, an alkoxy, an alkoxyaryloxy group, a halogen and zero but $R_2$ is not 3,4,5-trimethoxyphenyl, 3,4,5-trichlorophenyl, 3,4-dichlorophenyl, 2,5-dimethoxyphenyl or a p-benzoyl-L-glutamate when $R_1$ is hydrogen and $R_4$ is hydrogen, and $R_2$ is not p-benzoyl-L-glutamate when $R_1$ is methyl;

wherein $R_3$ is selected from the group consisting of hydrogen, a lower alkyl group, and zero and $R_3$ is zero when A is zero;

wherein $R_4$ is selected from the group consisting of hydrogen, a lower alkyl group and S-$R_7$ where $R_7$ is selected from the group consisting of phenyl, mono-, di- and tri-substituted phenyl, naphthyl, mono-, di- and tri-substituted naphthyl and p-aroyl-L-glutamate; and wherein each lower alkyl group is independently selected from the group consisting of lower alkyl groups having from 1 to 6 carbons.

The present invention also provides thieno[2,3-d] pyrimidine compounds, and pharmaceutically acceptable salts thereof, having the formula (5):

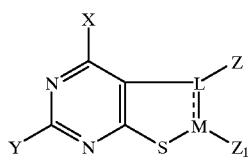

(5)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

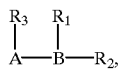

where Z is $R_4$ when $Z_1$ is

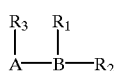

and Z is

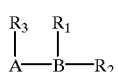

when $Z_1$ is $R_4$;

wherein A is selected from the group consisting of CH and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_2$ is selected from the group consisting of a lower alkyl group, an aryl group, p-aroyl-L-glutamate, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and lower alkyl group; and wherein each lower alkyl group is independently selected from the group consisting of lower alkyl groups having from about 1 to 6 carbons.

The present invention also provides pyrrolo[3,24d] pyrimidine compounds, and pharmaceutically acceptable salts thereof, having the formula (6):

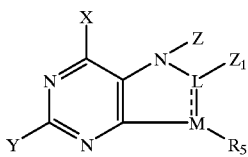

(6)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

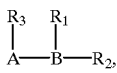

where Z is $R_4$ when $Z_1$ is

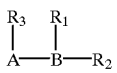

and Z is

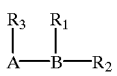

when $Z_1$ is $R_4$;

wherein A is selected from the group consisting of CH and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and lower alkyl group;

wherein $R_5$ is selected from the group consisting of hydrogen and lower alkyl group; and wherein each lower alkyl group is independently selected from the group consisting of lower alkyl groups having from about 1 to 6 carbons.

The present invention also provides pyrrolo[3,4-d] pyrimidine compounds, and pharmaceutically acceptable salts thereof, having the formula (7):

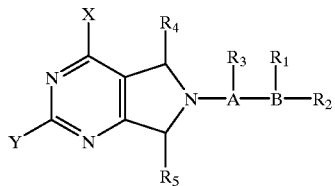

(7)

wherein X and Y are the same or different and are selected from the group consisting of OH, $NH_2$, H and $CH_3$;

wherein A is selected from the group consisting of CH and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group, and zero, and $R_3$ is zero when A is zero;

wherein $R_4$ is selected from the group consisting of hydrogen and lower alkyl group; and wherein each lower alkyl group is independently selected from the group consisting of lower alkyl groups having from about 1 to 6 carbons.

The present invention also provides cyclopentapyrimidine and cyclopenta[d]pyrimidine compounds, and pharmaceutically acceptable salts thereof, having the formula (8):

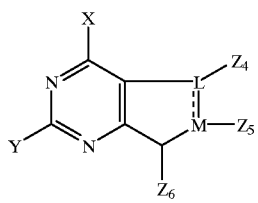

(8)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_4$, $Z_5$ and $Z_6$ are different and are selected from the group consisting of $R_4$, $R_5$ and

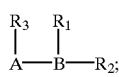

wherein A is selected from the group consisting of CH, sulfur and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and a lower alkyl group;

wherein $R_5$ is selected from the group consisting of hydrogen and a lower alkyl group;

wherein $R_4$ is the same or different than $R_5$;

wherein each of said $R_4$, $R_5$ and

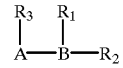

substituents is used once; and wherein each lower alkyl group is independently selected from the group consisting of lower alkyl groups having from about 1 to 6 carbons.

The present invention is also directed to tricyclic [3,2-d] and [2,3-d]pyrimidine compounds, and pharmaceutically acceptable salts thereof, having the formula (10):

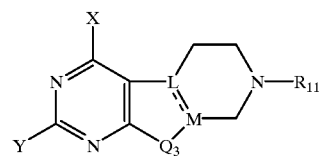

(10)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $R_{11}$ is selected from the group consisting of a lower alkyl group, an aryl group, p-aroyl-L-glutamate, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero;

$Q_3$ is selected from the group consisting of oxygen, NH, sulfur and $CH_2$.

The present invention is also directed to pyrido[2,3-d] and [3,2-d] pyrimidine compounds and pharmaceutically acceptable salts having the formula (11):

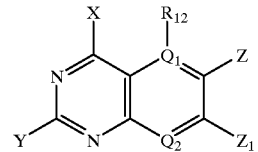

(11)

wherein X and Y may be the same or different and are selected from the group consisting of OH, $NH_2$, H and $CH_3$;

wherein Z and $Z_1$ are different and are selected from the group consisting of $R_4$ and $$\begin{array}{cc} R_3 & R_1 \\ | & | \\ A\text{—}B\text{—}R_2, \end{array}$$

where Z is $R_4$ when $Z_1$ is $$\begin{array}{cc} R_3 & R_1 \\ | & | \\ A\text{—}B\text{—}R_2 \end{array}$$

and Z is $$\begin{array}{cc} R_3 & R_1 \\ | & | \\ A\text{—}B\text{—}R_2 \end{array}$$

when $Z_1$ is $R_4$;

wherein $Q_1$ and $Q_2$ are the same or different and are selected from the group consisting of CH and nitrogen;

wherein A is selected from the group consisting of nitrogen, CH, sulfur and zero;

wherein B is selected from the group consisting of sulfur, sulfoxide, sulfone, CH, oxygen, nitrogen and zero; but B is not sulfur, sulfoxide, sulfone, oxygen or nitrogen when A is sulfur;

wherein $R_2$ is selected from the group consisting of hydrogen, a nitroso group, an aldehyde, a lower alkyl group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an aklyltriaryl group, a substituted diaryl group and a substituted triaryl group, and each substituent of the substituted aryl group, diaryl group, and triaryl group is the same or different and is selected from the group consisting of a lower alkyl group, an alkoxy, a substituted alkoxyaryloxy group, a halogen and zero;

wherein $R_3$ is selected from the group consisting of H, a lower alkyl and zero, and $R_3$ is zero when A is zero;

wherein $R_{12}$ is selected from the group consisting of hydrogen and methyl;

but $R_2$ is not 2,5-dimethoxyphenyl when X is $NH_2$, Y is $NH_2$, $Q_1$ is CH, $Q_2$ is N, $Z_1$ is H, B is CH, $R_1$ is H and $R_{12}$ is methyl; and wherein each lower alkyl group is independently selected from the group consisting of lower alkyl groups having from about 1 to 6 carbons.

The present invention is also directed to pyrido[2,3-d] and [3,4-d]pyrimidine compounds and pharmaceutically acceptable salts having the formula (12):

(12)

wherein X and Y may be the same or different and are selected from the group consisting of OH, $NH_2$, H and $CH_3$;

wherein Z and $Z_1$ are different and are selected from the group consisting of $R_4$ and $$\begin{array}{cc} R_3 & R_1 \\ | & | \\ A\text{—}B\text{—}R_2, \end{array}$$

where Z is $R_4$ when $Z_1$ is $$\begin{array}{cc} R_3 & R_1 \\ | & | \\ A\text{—}B\text{—}R_2 \end{array}$$

and Z is $$\begin{array}{cc} R_3 & R_1 \\ | & | \\ A\text{—}B\text{—}R_2 \end{array}$$

when $Z_1$ is $R_4$;

wherein $Q_1$ and $Q_2$ are the same or different and are selected from the group consisting of CH and nitrogen;

wherein A is selected from the group consisting of nitrogen, CH, sulfur and zero;

wherein B is selected from the group consisting of sulfur, sulfoxide, sulfone, CH, oxygen, nitrogen and zero; but B is not sulfur, sulfone, oxygen or nitrogen when A is sulfur;

wherein $R_1$ is selected from the group consisting of hydrogen, a nitroso group, an aldehyde, a lower alkyl group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryi group, an alicyclic hydrocarbon group, an aklyltriaryl group, a substituted diaryl group and a substituted triaryl group, and each substituent of the substituted aryl group, diaryl group, and triaryl group is the same or different and is selected from the group consisting of a lower alkyl group, an alkoxy, a substituted alkoxyaryloxy group, a halogen and zero;

wherein $R_3$ is selected from the group consisting of H, a lower alkyl and zero, and $R_3$ is zero when A is zero;

wherein $R_{12}$ is selected from the group consisting of hydrogen and methyl; and wherein each lower alkyl group is independently selected from the group consisting of lower alkyl groups having from about 1 to 6 carbons.

Methods of synthesizing the above compounds are also disclosed.

As used herein, the term "pharmaceutically acceptable salts" includes, but is not limited to, acetate, formate, glucuronate, ethantate, sulfonate, or other salts known to those skilled in the art.

In formulas 1 and 4–11, when X and Y are the same or different and are selected from the group consisting of OH, $NH_2$, H and $CH_3$, the enol form of the compounds is represented. The enol form is equivalent to and includes the keto form of the compounds.

As used herein, the term "lower alkyl group" refers to an alkyl group having between 1 and 6 carbons. The number of carbons in each lower alkyl group in each of formulas 1 and 3–11 can vary. For example, with reference to Formula 4, $R_1$ could represent a lower alkyl group having 1 carbon, $R_2$ could represent a lower alkyl group having 2 carbons, $R_3$ could represent a lower alkyl group having 3 carbons, and $R_4$ could represent a lower alkyl group having 4 carbons.

As will be understood one skilled in the art, when any of the variables used herein equal zero, that variable is not present in a particular embodiment of the general formula. In any of the above described formulas, when A equals zero, $R_3$ also equals zero, and B is either zero or is attached directly to the carbon ring. When B is zero, $R_1$ also equals zero, and $R_2$ and $R_8$ are either zero or are attached directly to A. When both A and B are zero, $R_1$ and $R_3$ are also zero and $R_2$ and $R_8$ are either zero or are attached directly to the carbon ring.

As used herein, the term aroyl, such as for example when used within the term p-aroyl-L-glutamate, refers to heteroaroyl, benzoyl, napthoyl, thiophenoyl, furophenoyl, pyrroyl, and any other aroyl as that term would be understood by one skilled in the art.

This invention also provides methods for therapeutically and/or prophylactically using the compounds, and pharmaceutically acceptable salts thereof, described herein.

This invention provides a method of using the pyrimidine derivatives of Formulas 1, and 4–11 described herein for therapeutic and prophylactic purposes including employing these compounds to resist and treat secondary infections caused by *Pheumocystis carini* and *Toxoplasmosis gondii* or other organisms in immunocompromised patients, such as for example patients with AIDS. The immunocompromised patient has a primary infection caused by a retrovirus, including for example, human immunodeficiency virus (HIV). In addition, this invention provides methods of using pyrimidine derivatives as antitumor, antibiotic, antimalarial, antifungal and antiprotozoal agents and as synergistic agents with sulfonamides in such patients.

This invention also provides methods of using pyrimidine derivatives for therapeutic purposes as antitumor agents or to otherwise destroy cancerous cells in cancer patients.

It is an object of this invention to provide pyrimidine derivative compounds, and pharmaceutically acceptable salts thereof, for substantially inhibiting dihydrofolate reductase enzymes.

It is an object of this invention to provide pyrimidine derivative compounds, and pharmaceutically acceptable salts thereof, for substantially inhibiting thymidylate synthase enzymes.

It is an object of the present invention to provide pyrimidine derivative compounds, and pharmaceutically acceptable salts thereof, having antitumor, antibiotic, antimalarial, antifungal or antiprotozoal activity or synergistic activity with sulfonamides.

It is a further object of this invention to provide pyrimidine derivative compounds, and pharmaceutically acceptable salts thereof, having effective activity against secondary infections, such as for example infections caused by *Pneumocystis carinii* and *Toxoplasmosis gondii* that occur in immunocompromised patients, such as for example patients with AIDS.

It is another object of this invention to provide pyrimidine derivative compounds, and pharmaceutically acceptable salts thereof, having effective activity against tumors and other cancerous cells, such as those caused by cancer.

It is an object of this invention to provide a method of synthesizing various pyrimidine derivative compounds, and pharmaceutically acceptable salts thereof.

It is a further object of this invention to provide methods of using in a patient a therapeutically effective amount of pyrimidine derivative compounds, or pharmaceutically acceptable salts thereof.

It is a further object of this invention to provide methods of using in a patient a prophylactically effective amount of pyrimidine derivative compounds, or pharmaceutically acceptable salts thereof.

These and other objects of the invention will be more fully understood from the drawing and the following description of the invention and the claims appended hereto.

BRIEF DESCRIPTION OF THE DRAWINGS

FIG. 2 shows compounds 1–9 as synthesized by the methods shown in FIG. 1.

FIG. 9 shows of compounds having formula 9 as synthesized by the methods shown in FIG. 8.

FIG. 10 shows a schematic diagram of methods of preparing tricyclic[2,3-d]pyrimidines.

FIG. 12 shows a schematic diagram of the methods of preparing pyrido[3,2-d]pyrimidines.

FIG. 13 shows a schematic diagram of the methods of preparing pyrido[2,3-d]pyrimidines.

FIG. 14 shows a schematic diagram of the methods of preparing various 2,4-diaminopyrido[2,3-d]pyrimidines.

FIG. 17 shows a schematic diagram of the methods of preparing pyrido[3,2-d]pyrimidines.

FIG. 18 shows a schematic diagram of the methods of preparing pyrido[3,2-d]pyrimidines.

DESCRIPTION OF THE PREFERRED EMBODIMENT

Figure 1:
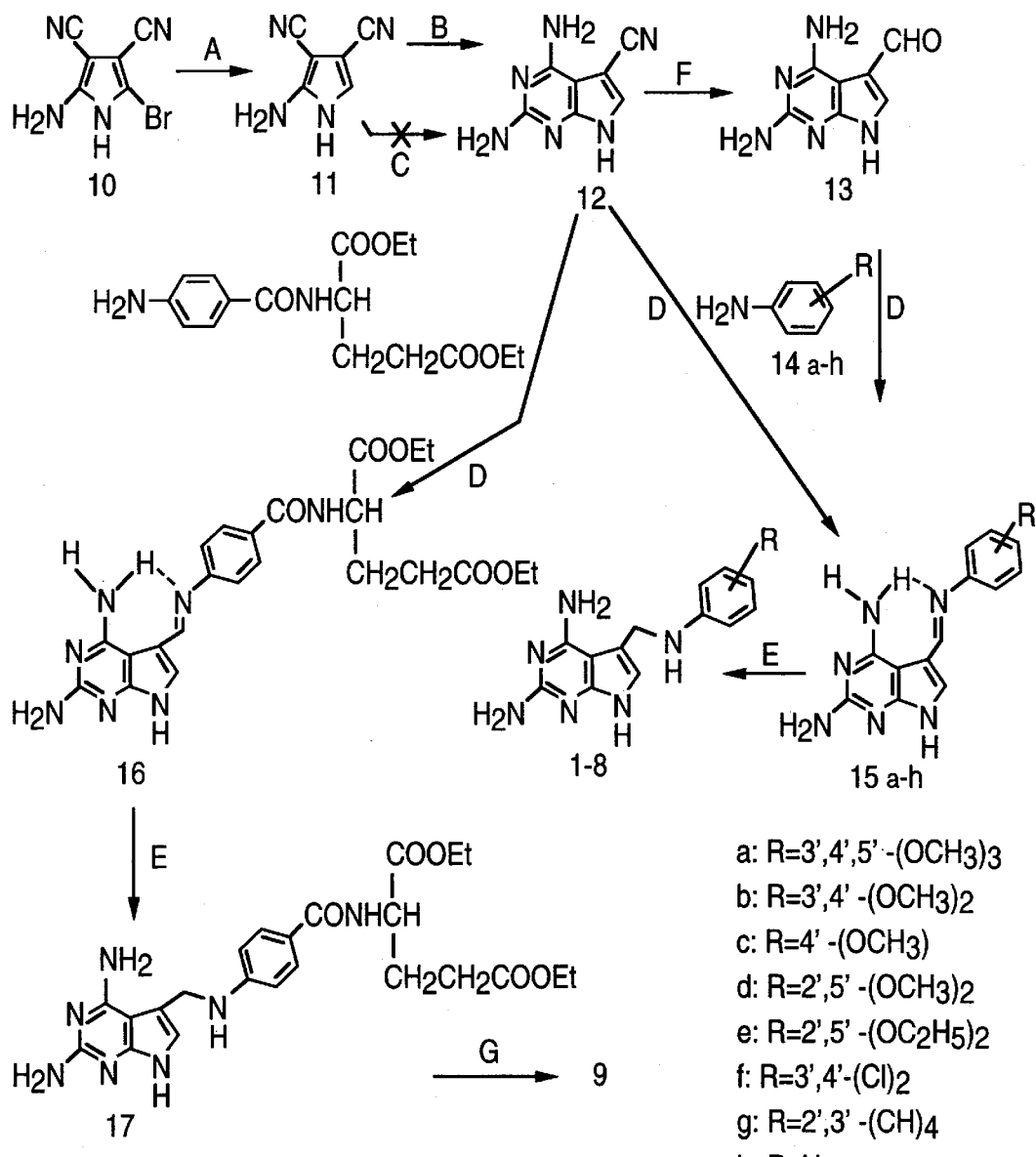
FIG. 1 shows a schematic diagram of methods of preparing 2,4-diamino-5-substituted-pyrrolo[2,3-d]pyrimidines.
Figure 3:
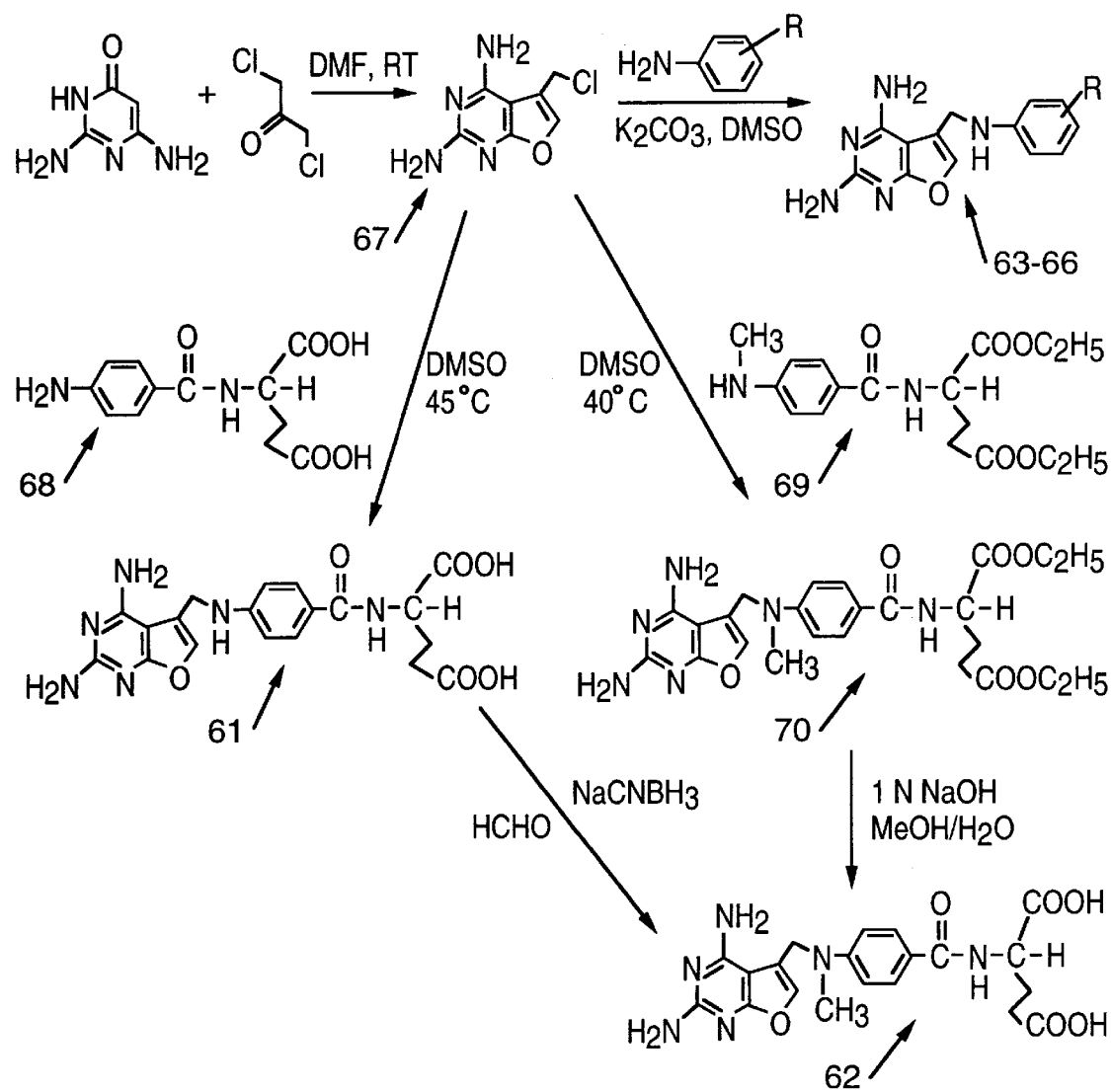
FIG. 3 shows a schematic diagram of the methods of preparing N-[4-[N-[2,4-diaminofuro[2,3-d]pyrimidin-5-yl]methyl]amino]benzoyl]-L-glutamic acid and the N-9 methyl analogue thereof.
Figure 4:
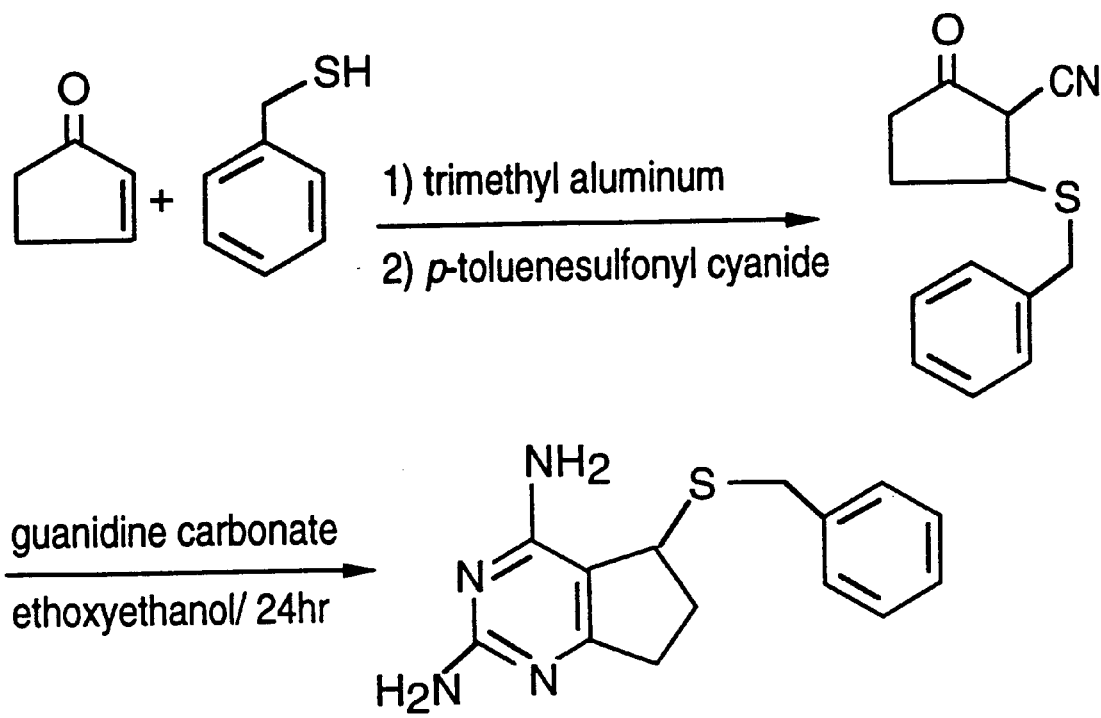
FIG. 4 shows a schematic diagram of the methods of preparing of a compound having formula 8.

As used herein, the term "patients" means members of the animal kingdom including but not limited to human beings.

The pyrimidine derivative compounds, and pharmaceutically acceptable salts thereof, and methods of preparing and using the compounds of this invention provide for the therapeutic and prophylactic treatment of secondary infections caused by *Pneumocystis carinii* and *Toxoplasmosis gondii* in immunocompromised patients. The patients have a primary infection caused by a retrovirus including human immunodeficiency virus (HIV). As will be appreciated by one skilled in the art, embodiments of the compounds, and pharmaceutically acceptable salts thereof, of the present invention which contain benzoyl-L-glutamate groups will not be applicable to these methods. That is because *Pneumocystis carinii* and *Toxoplasmosis gondii* are not generally known to take up enough of the benzoyl-L-glutamate forms of these compounds to be effective.

In addition, these compounds function as antitumor, antibiotic, antifungal, antimalarial and antiprotozoal agents, and as synergistic agents with sulfonamides.

In addition, the compounds of this invention provide for the therapeutic treatment of tumors, or other cancerous cells, in cancer patients. As used herein, the term "cancer" refers to any type of cancer including, but not limited to, leukemia, lung cancer, colon cancer, CNS cancer, melanoma, ovarian cancer, renal cancer, prostate cancer, and breast cancer.

The compounds disclosed in the present invention can all be generally described as antifolates. The pyrrolo[2,3-d]pyrimidine compounds, furo[2,3-d]pyrimidine compounds, pyrrolo[3,2-d] and pyrrolo[3,4-d]pyrimidine compounds, thieno[2,3-d]pyrimidine compounds, cyclopentapyrimidine compounds, cyclopenta-[d]pyrimidine compounds, pyrido[2,3-d]pyrimidine compounds, and pyrido[3,2-d]pyrimidine compounds, and pharmaceutically acceptable salts thereof, of this invention inhibit dihydrofolate reductase (DHFR) enzymes. The DHFR enzymes are needed for normal cell growth because they reduce dihydrofolate to tetrahydrofolate. Tetrahydrofolate is a precursor of 5,10-methylenetetrahydrofolate, which is essential for DNA replication and thus cell growth. The derivatives of the present invention inhibit dihydrofolate reductase and consequently inhibit DNA synthesis. Inhibition of DNA synthesis results in cell death.

In addition, the pyrimidine derivative compounds of the present invention, and pharmaceutically acceptable salts thereof, inhibit thymidylate synthase (TS). TS, along with DHFR, forms part of the system responsible for the synthesis of deoxythymidylate (dTMP) from deoxyuridylate (dUMP). Inhibition of TS deprives the cell of thymidine, which is an essential component of DNA.

The pyrrolo[2,3-d]pyrimidine compounds, and pharmaceutically acceptable salts thereof, of the present invention have the general formula (1):

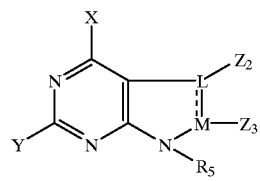

(1)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_3$ are different and are selected from the group consisting of $R_4$ and

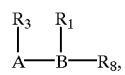

where $Z_2$ is $R_4$ when $Z_3$ is

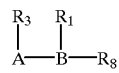

and $Z_2$ is

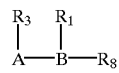

when $Z_3$ is $R_4$;

wherein A is selected from the group consisting of CH and zero;

wherein B is selected from the group consisting of CH, nitrogen, N—$CH_2$, $CH_2$—N, $CH_2$—$CH_2$, oxygen, sulfur, sulfoxide, sulfone and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_3$ is selected from the group consisting of hydrogen, a lower alkyl group and zero, and $R_3$ is zero when A is zero;

wherein $R_4$ is selected from the group consisting of hydrogen and a lower alkyl group;

wherein $R_5$ is selected from the group consisting of hydrogen and a lower alkyl group;

wherein $R_8$ is selected from the group consisting of naphthyl, mono-, di- and tri-substituted naphthyl, thionaphthyl, thiophenyl and hydroxyphenyl when $R_1$ is hydrogen and $R_4$ is hydrogen;

wherein $R_8$ is selected from the group consisting of phenyl, mono-, di- and tri-substituted phenyl, naphthyl, mono-, di- and tri-substituted naphthyl, pyridine and p-aroyl-L-glutamate when $R_1$ is a lower alkyl group and $R_4$ is hydrogen;

wherein $R_8$ is selected from the group consisting of pyridine, phenyl, mono-, di- and tri-substituted phenyl, naphthyl, and mono-, di- and tri-substituted naphthyl and p-aroyl-L-glutamate when $R_1$ is zero;

wherein $R_8$ is selected from the group consisting of phenyl, mono-, di- and tri-substituted phenyl, naphthyl, mono-, di- and tri-substituted naphthyl and p-aroyl-L-glutamate when $R_1$ is hydrogen and $R_4$ is a lower alkyl group; and wherein $R_8$ is not p-benzoyl-L-glutamate or pyridine when X is OH, A is zero, B is sulfur, $R_4$ is methyl and $R_5$ is hydrogen, and $R_8$ is not p-benzoyl-L-glutamate when X is OH, A is CH, B is CH, $R_4$ is hydrogen and $R_5$ is hydrogen; and wherein each lower alkyl group is independently selected from the group consisting of lower alkyl groups having from 1 to 6 carbons.

Preferred embodiments of formula 1 are further recited in Table 1.

More specifically, the present invention is directed to a method of synthesizing a compound, and pharmaceutically acceptable salts thereof, having the formula:

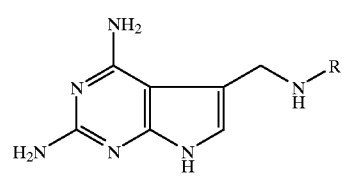

(2)

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group,

TABLE 1

| Compound | X | Y | L-M Bond | A | B | $R_1$ | $R_3$ | $R_4$ | $R_5$ | $R_6$ |
|---|---|---|---|---|---|---|---|---|---|---|
| 301 | $NH_2$ | $NH_2$ | dbl | CH | N | H | H | H | H | 1-naphthyl |
| 303 | $NH_2$ | $NH_2$ | dbl | CH | N | H | H | H | H | 4-OHphenyl |
| 304 | $NH_2$ | $NH_2$ | dbl | CH | N | $CH_3$ | H | H | H | 2,5-dimethoxy-phenyl |
| 305 | $NH_2$ | $NH_2$ | dbl | CH | N | $CH_3$ | H | H | H | 3,4-dichloro-phenyl |
| 306 | $NH_2$ | $NH_2$ | dbl | CH | N | $CH_3$ | H | H | H | 1-naphthyl |
| 307 | $NH_2$ | $NH_2$ | dbl | CH | S | —* | H | H | H | 3,4-dimethoxy-phenyl |
| 308 | $NH_2$ | $NH_2$ | dbl | CH | S | — | H | H | H | 3,4-dichloro-phenyl |
| 309 | $NH_2$ | $NH_2$ | dbl | CH | S | — | H | H | H | 1-naphthyl |
| 310 | $NH_2$ | $NH_2$ | dbl | CH | S | — | H | H | H | 2-naphthyl |
| 312 | $NH_2$ | $NH_2$ | dbl | CH | N | $CH_3$ | H | H | H | p-benzoyl-L-glutamate |
| 313 | OH | $NH_2$ | dbl | CH | N | H | H | $CH_3$ | H | p-benzoyl-L-glutamate |
| 314 | OH | $NH_2$ | dbl | CH | N—$CH_2$ | H | H | $CH_3$ | H | p-benzoyl-L-glutamate |
| 315 | OH | $NH_2$ | dbl | CH | S | — | H | $CH_3$ | H | 4-pyridine |
| 317 | OH | $NH_2$ | dbl | — | S | — | — | $CH_3$ | H | 3,4-di-methoxy-phenyl |
| 318 | OH | $NH_2$ | dbl | — | S | — | — | $CH_3$ | H | 3,4-dichloro-phenyl |
| 319 | OH | $NH_2$ | dbl | — | S | — | — | $CH_3$ | H | 4-chloro-phenyl |
| 320 | OH | $NH_2$ | dbl | — | S | — | — | $CH_3$ | H | 4-$NO_2$phenyl |
| 321 | OH | $NH_2$ | dbl | -- | S | — | — | $CH_3$ | H | phenyl |
| 322 | OH | $NH_2$ | dbl | — | S | — | — | $CH_3$ | H | 2-naphthyl |

"—" indicates that the substituent is zero, that is, not present in the particular embodiment.

The most preferred embodiments of formula 1 are identified as compounds 312 and 320.

The present invention is further directed to methods of synthesizing 5-substituted pyrrolo[2,3-d] pyrimidines. Synthesis of these compounds according to the methods of the present invention can be accomplished by convergent synthesis. As will be understood by one skilled in the art, convergent synthesis involves the production of an intermediate product from which numerous additional compounds can be made. Here, the preferred intermediate product is 2,4-diamino-5-cyano pyrrolo-[2,3-d]pyrimidine.

alkyltriaryl group is the same or different and is selected from the group consisting of a lower alkyl group, an alkoxy, a substituted alkoxyaryloxy group and a halogen; and wherein each lower alkyl group is independently selected from the group consisting of lower alkyl groups having from about 1 to 6 carbons, comprising the steps of:
a) debrominating a pyrrole;
b) fusing the product of step a) with an amidine;
c) condensing the product of step b) with a nucleophile;
d) reducing the product of step c); and
e) purifying the compounds of step d).

Preferably, the debromination of step a) is performed in a mixture of dimethylformamide (DMF) and methanol under hydrogenation in the presence of a palladium catalyst. Either a 5% Pd—BaCO$_3$ or a 10% Pd—C catalyst can be used; 5% Pd—BaCO$_3$ is preferred. Typically, the debromination step will be completed in about 3 hours, and the reaction performed under hydrogen at a pressure of between about 40 and 60 psi, preferably at about 50 psi.

The fusion of step b) is preferably performed with chlorformamidine hydrochloride, and more preferably performed by heating a uniformly stirred suspension of the product of step a) and chlorformamidine hydrochloride in a liquid heat transfer media and heating to a temperature of between about 150° C. and 180° C., preferably between about 160° C. and 170° C., for a period of between about 36 and 50 hours, preferably about 48 hours. Any liquid heat transfer media can be used, including Dowtherm-A®, available from Dow Chemical Company.

The selective nucleophile as disclosed in condensing step c) is selected from the group consisting of an aniline, diethyl(p-aminoaroyl)-L-glutamate, N-methyl and diethyl (p-aminoaroyl)-L-glutamate. Any suitable aniline can be used, including but not limited to an aniline of the formula

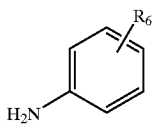

(3)

wherein R$_6$ is selected from the group consisting of 3',4',5'-trimethoxy, 3',4'-dimethoxy, 4'-methoxy, 2',5'-dimethoxy, 2',5'-diethoxy, 3',4'-dichloro, 2',3'-tetramethyl, hydrogen trimethoxy, dimethoxy and monomethoxy groups, trihalo, dihalo and monohalo groups, trialkyl, dialkyl and monoalkyl groups and combinations of methoxy groups, halo groups and lower alkyls.

Anilines of formula 3 are preferred for use in the methods of the present invention.

Preferably, the condensation of step c) is performed in 70% to 80% acetic acid under hydrogenation, and in the presence of a Raney nickel catalyst. Hydrogenation times of from about 24 to 72 hours, and hydrogenation pressures of between about 50 and 60 psi, preferably 55 psi, are preferred. Under these conditions, the Schiff bases are expected to form.

Alternatively, condensation can be accomplished by heating a mixture of the product of step b) with formaldehyde and Raney nickel at a temperature between about 70° and 90° C., preferably 80° C., for about 2 hours.

Reduction of the Schiff bases, step d), is preferably performed by stirring a solution of the product of step c) in methanol at room temperature using NaCNBH as the reducing agent. In addition, 50% methanolic hydrochloric acid or glacial acetic acid can be used to maintain the pH of the reaction mixture at about 2. The reduction step should take about 4 hours.

Preferably, the purification of step e) is performed by a method selected from the group consisting of silica gel column chromatography and dissolution of the product of step d) in methanol, filtration, evaporation of the filtrate, and trituration of the residue in anhydrous diethylether.

When either diethylip-aminoaroyl)-L-glutamate or N-methyl diethyl(p-aminoaroyl)-L-glutamate are used in the condensation of step c), an additional hydrolysis step, step f), is preferably performed following step e). Preferably, the hydrolysis of step f) is accomplished by stirring a solution of the product of step e) in a 1:1 sodium hydroxide:methanol solution at room temperature for between about 60 and 84 hours, preferably about 72 hours.

Specific embodiments of these methods are discussed in the examples below.

Preferred embodiments of the compounds produced by the methods of the present invention are further recited in Table 2.

TABLE 2

| Compound Number | R Group |
|---|---|
| 1 | 3,4,5-trimethoxyphenyl |
| 2 | 3,4-dimethoxyphenyl |
| 3 | 2,5-dimethoxyphenyl |
| 4 | 4-methoxyphenyl |
| 5 | 2,5-diethoxyphenyl |
| 6 | 3,4-dichlorophenyl |
| 7 | 2',3'-(CH)$_4$phenyl |
| 8 | phenyl |
| 9 | p-benzoyl-L-glutamate |

Compounds 4, 8 and 9, as defined in the above table, are preferred for therapeutically treating cancer patients, and compounds 4 and 8 for therapeutically and prophylactically treating infections caused by *Pneumocystis carinii* and *Toxoplasmosis gondii*.

The present invention also provides pyrrolo[2,3-d] pyrimidine compounds, and pharmaceutically acceptable salts thereof, having the formula (9):

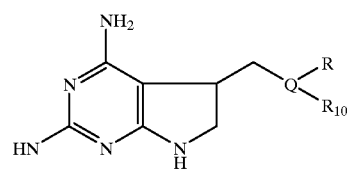

(9)

wherein Q is selected from the group consisting of nitrogen and sulfur;

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen;

wherein R$_{10}$ is selected from the group consisting of hydrogen and a lower alkyl group; and wherein R$_{10}$ is a lower alkyl when Q is nitrogen.

Methods of synthesizing compounds having formula 9 as described above are also provided. These methods comprise the steps of:

a) debrominating a pyrrole;

b) fusing the product of step a) with an amide;

c) condensing the product of step b) with a nucleophile;

d) reducing the product of step c); and e) purifying the compounds of step d); wherein the nucleophile of step c) is a compound having the general structure

wherein Q is selected from the group consisting of nitrogen and sulfur;

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen;

wherein $R_{10}$ is selected from the group consisting of hydrogen and a lower alkyl group; and wherein $R_{10}$ is a lower alkyl when Q is nitrogen.

The present invention is also directed to furo[2,3-d] pyrimidine compounds, and pharmaceutically acceptable salts thereof, having the following general formula:

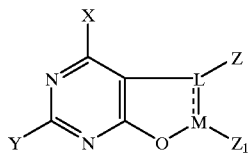

(4)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

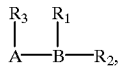

where Z is $R_4$ when $Z_1$ is

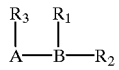

and Z is

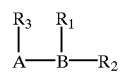

when $Z_1$ is $R_4$;

wherein A is selected from the group consisting of CH and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl, an alkoxy, an alkoxyaryloxy group, a halogen and zero but $R_2$ is not 3,4,5-trimethoxyphenyl, 3,4,5-trichlorophenyl, 3,4-dichlorophenyl, 2,5-dimethoxyphenyl or a p-benzoyl-L-glutamate when $R_1$ is hydrogen and $R_4$ is hydrogen, and $R_2$ is not p-benzoyl-L-glutamate when $R_1$ is methyl;

wherein $R_3$ is selected from the group consisting of hydrogen, a lower alkyl group, and zero and $R_3$ is zero when A is zero;

wherein $R_4$ is selected from the group consisting of hydrogen, a lower alkyl group and S-$R_7$ where $R_7$ is selected from the group consisting of phenyl, mono-, di- and tri-substituted phenyl, naphthyl, mono-, di- and tri-substituted naphthyl and p-aroyl-L-glutamate; and wherein each lower alkyl group is independently selected from the group consisting of lower alkyl groups having from 1 to 6 carbons.

Particularly preferred embodiments of formula 4 are recited below in Table 3. For all of the embodiments described in Table 3, X is $NH_2$, Y is $NH_2$ and the bond between L and M is a double bond.

TABLE 3

| Compound | A | B | $R_1$ | $R_2$ | $R_3$ | $R_4$ |
|---|---|---|---|---|---|---|
| 159 | CH | S | — | phenyl | H | H |
| 160 | CH | S | — | 1-naphthyl | H | H |
| 161 | CH | S | — | 2-naphthyl | H | H |
| 162 | CH | N | H | 1-naphthyl | H | H |
| 163 | CH | N | H | 2-naphthyl | H | H |
| 164 | CH | O | — | 2-naphthyl | H | H |
| 165 | CH | N | H | 2-phenoxyphenyl | H | H |
| 166 | CH | N | H | 4-phenoxyphenyl | H | H |
| 167 | CH | N | H | 2-phenylphenyl | H | H |
| 169 | CH | N | H | 2',5'-dichlorophenyl | H | H |
| 171 | CH | N | $CH_3$ | 3',4'-dichlorophenyl | H | H |
| 172 | CH | N | $CH_3$ | 3',4',5'-trichlorophenyl | H | H |
| 175 | CH | N | H | 3'-methoxyphenyl | H | H |
| 177 | CH | H | — | — | H | S-$R_7$* |

TABLE 3-continued

| Compound | A | B | $R_1$ | $R_2$ | $R_3$ | $R_4$ |
|---|---|---|---|---|---|---|
| 178 | CH | H | — | — | H | S-$R_7$* |
| 179 | — | — | — | phenyl | — | H |

*$R_7$ equals 1-naphthyl
'$R_7$ equals 2-naphthyl

Compounds 161 and 167 as described in Table 3 are most preferred for therapeutically treating cancer patients, and therapeutically and prophylactically treating infections caused by *Pneumocystis carinii* and *Toxoplasmosis gondii*.

The present invention is also directed to methods for synthesizing the compound, and pharmaceutically acceptable salts thereof, having the formula

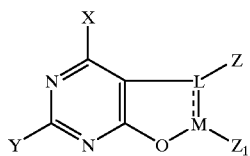

(4)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

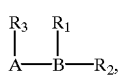

where Z is $R_4$ when $Z_1$ is

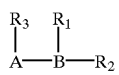

and Z is

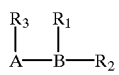

when $Z_1$ is $R_4$;

wherein A is selected from the group consisting of CH and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero, but $R_2$ is not 3,4,5-trimethoxyphenyl, 3,4,5-trichlorophenyl, 3,4-dichlorophenyl, 2,5-dimethoxyphenyl or p-benzoyl-L-glutamate when $R_1$ is hydrogen and $R_4$ is hydrogen, and $R_2$ is not p-benzoyl-L-glutamate when $R_1$ is methyl;

wherein $R_3$ is selected from the group consisting of hydrogen, a lower alkyl group, and zero and $R_3$ is zero when A is zero;

wherein $R_4$ is selected from the group consisting of hydrogen, a lower alkyl group and S-$R_7$ where $R_7$ is selected from the group consisting of phenyl, mono-, di- and tri-substituted phenyl, naphthyl, mono-, di- and tri-substituted naphthyl and p-aroyl-L-glutamate; and wherein each lower alkyl group is independently selected from the group consisting of lower alkyl groups having from 1 to 6 carbons, comprising the steps of:

a) stirring a pyrimidine and a substituted acetone in a solvent;
b) purifying the product of step a);
c) performing nucleophilic displacement of the chloride in the product of step b); and
d) purifying the product of step c).

In one embodiment of the methods described above, step a) is performed by stirring one equivalent each of 2,6-diamino-4-hydroxypyrimidine and 1,3-dichloroacetone in DMF at room temperature for a period of between about 12 and 36 hours, preferably 24 hours.

Purification of the product of step a) can be accomplished by any means known in the art; column chromatography is preferred. The product resulting from the purification step b) is not generally stable for long durations at room temperature. It is, therefore, preferred that the nucleophilic displacement of step c) be performed within about 1 hour of completion of step b).

The nucleophilic displacement of step c) can be accomplished by any of various compounds including those selected from the group consisting of (p-aminoaroyl)-L-glutamic acid, diethyl N-(p-methylaminoaroyl)glutamate, and a nucleophile. As used in reference to the methods for synthesizing a compound, and pharmaceutically acceptable salts thereof, having formula (4), nucleophile includes, but is not limited to aniline, substituted analines, phenols, thiophenols and substituted phenols and thiophenols.

When step c) is performed with (p-aminoaroyl)-L-glutamic acid, the purification of step d) is preferably performed by precipitating the product of step c) by diluting said product with a suitable solvent, preferably water, and separating said product from unreacted starting materials and impurities by any means known in the art; cellulose column chromatography is preferred. Acidification of the product is then preferred.

When the nucleophilic displacement of step c) is performed with diethyl N-[p-methylamino(aroyl)]glutamate, the purification of step d) is preferably accomplished by stirring the product of step c) with 1 N sodium hydroxide at room temperature for between about 12 to 36, preferably 24 hours, followed by acidification.

Alternatively, when conducting the nucleophilic displacement with (p-aminoaroyl)-L-glutamic acid, the desired product can also be obtained by reductive methylation of the intermediate with a suitable aldehyde, preferably formaldehyde, and sodium cyanoborohydride at a pH of approximately 6 to 7. Purification is then accomplished by any means known in the art, preferably by wet cellulose column, and acidification of the product performed.

When the nucleophilic displacement reactions are accomplished with an aniline, the product of step b) is preferably mixed with anhydrous dimethylsulfoxide and two equivalents of potassium carbonate for approximately 60 to 84 hours, preferably 72 hours, at room temperature. Heating the reaction mixture to between about 35° and 45° C. for a period of between about 60 and 84 hours, preferably 72 hours, increases the yield of the desired product. The product is then isolated from impurities and other unreacted starting materials by any means known in the art. Preferably, isolation is accomplished by adding excess water to the reaction mixture and stirring at room temperature for a period of approximately 6 to 8 hours to separate the product; chromatographic purification is then performed.

The present invention is also directed to compounds, and pharmaceutically acceptable salts thereof, having the general formula 5

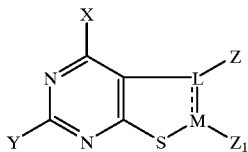

(5)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

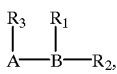

where Z is $R_4$ when $Z_1$ is

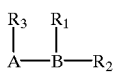

and Z is

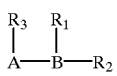

when $Z_1$ is $R_4$;

wherein A is selected from the group consisting of CH and zero;

wherein B is selected from the group consisting of sulfur, sulfoxide, sulfone, nitrogen, oxygen, CH, $N-CH_2$, $CH_2-N$, $CH_2-CH_2$, and zero;

wherein $R_1$ is selected from the group consisting of hydrogen, a lower alkyl group, a nitroso group, a formyl group and zero and $R_1$ is zero when B is zero, oxygen, sulfur, sulfoxide or sulfone;

wherein $R_2$ is selected from the group consisting of a lower alkyl group, an aryl group, p-aroyl-L-glutamate, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and lower alkyl group; and wherein each lower alkyl group is independently selected from the group consisting of lower alkyl groups having from about 1 to 6 carbons.

The present invention is also directed to compounds, and pharmaceutically acceptable salts thereof, having the general formula:

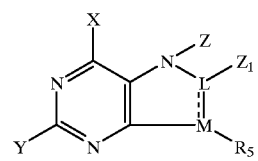

(6)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

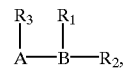

where Z is $R_4$ when $Z_1$ is

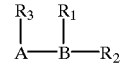

and Z is

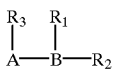

when $Z_1$ is $R_4$;
wherein A is selected from the group consisting of CH and zero;
wherein B is selected from the group consisting of sulfur, sulfoxide, sulfone, nitrogen, oxygen, CH, N—CH$_2$, CH$_2$—N, CH$_2$—CH$_2$, and zero;
wherein $R_1$ is selected from the group consisting of hydrogen, a lower alkyl group, a nitroso group, a formyl group and zero, and $R_1$ is zero when B is zero, oxygen, sulfur, sulfoxide or sulfone;
wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, an alkoxyaryloxy group, a halogen and zero;
wherein $R_3$ is selected from the group consisting of hydrogen, a lower alkyl group and zero, and $R_3$ is zero when A is zero;
wherein $R_4$ is selected from the group consisting of hydrogen and lower alkyl group;
wherein $R_5$ is selected from the group consisting of hydrogen and lower alkyl group; and
wherein each lower alkyl group is independently selected from the group consisting of lower alkyl groups having from about 1 to 6 carbons.

In preferred embodiments of formula 6, Y and X are NH$_2$, the bond between L and M is a double bond, A is zero, B is CH, $R_1$ is hydrogen, $R_2$ is selected from the group consisting of phenyl and 3,4-dichlorophenyl, $R_3$ is zero, $R_4$ is selected from the group consisting of hydrogen and lower alkyl and $R_5$ is selected from the group consisting of hydrogen and lower alkyl.

The present invention is also directed to compounds, and pharmaceutically acceptable salts thereof, having the general formula:

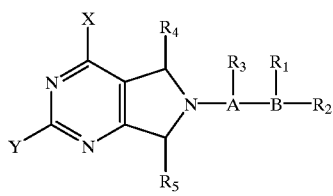

(7)

wherein X and Y are the same or different and are selected from the group consisting of OH, NH$_2$, H and CH$_3$;
wherein A is selected from the group consisting of CH and zero;
wherein B is selected from the group consisting of sulfur, sulfoxide, sulfone, nitrogen, oxygen, CH, N—CH$_2$, CH$_2$—N, CH$_2$—CH$_2$, and zero;
wherein $R_1$ is selected from the group consisting of hydrogen, a lower alkyl group, a nitroso group, a formyl group and zero, and $R_1$ is zero when B is zero, oxygen, sulfur, sulfoxide or sulfone;
wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, an alkoxyaryloxy group, a halogen and zero;
wherein $R_3$ is selected from the group consisting of hydrogen, a lower alkyl group, and zero, and $R_3$ is zero when A is zero;
wherein $R_4$ is selected from the group consisting of hydrogen and lower alkyl group; and
wherein each lower alkyl group is independently selected from the group consisting of lower alkyl groups having from about 1 to 6 carbons.

Figure 5:
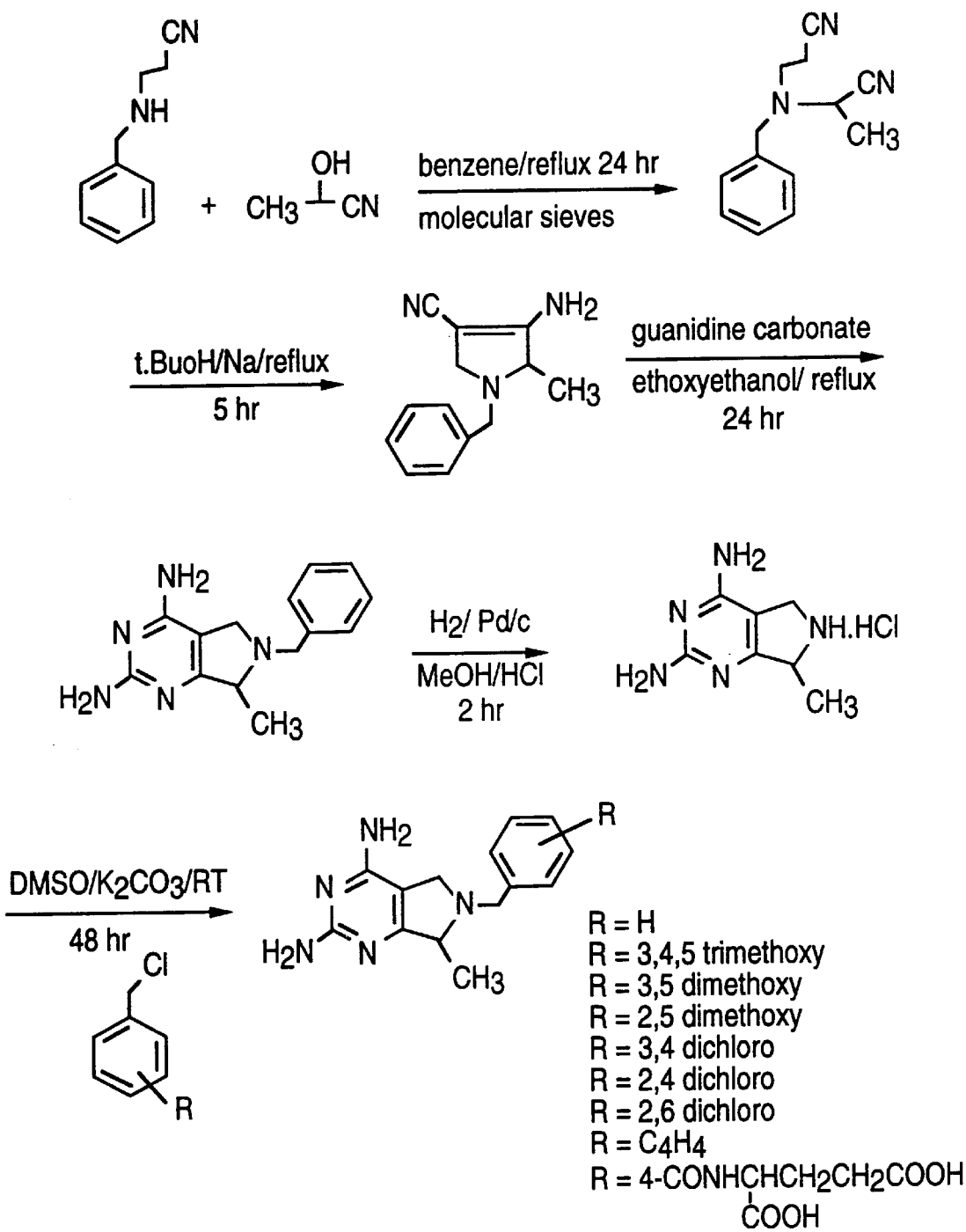
FIG. 5 shows a schematic diagram of the methods of preparing several compounds having formula 7.

In preferred embodiments of formula 7, X and Y are NH$_2$, A is zero, B is CH, $R_1$ is hydrogen, $R_2$ is selected from the group consisting of 3,4,5-trimethoxybenzyl, 3,5-dimethoxybenzyl, 2,5-dimethoxybenzyl, 3,4-dichlorobenzyl, 2,6-dichlorobenzyl, 2,4dichlorobenzyl, 2-CH$_2$-naphthyl, C$_4$H$_4$benzyl and 4-benzyl-L-glutamate, $R_3$ is zero, $R_4$ is hydrogen, and $R_5$ is selected from the group consisting of hydrogen and methyl. The most preferred embodiments of formula (7) are illustrated in FIG. 5.

The present invention is also directed to compounds, and pharmaceutically acceptable salts thereof, having the formula:

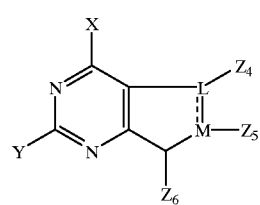

(8)

wherein X and Y are the same or different and are selected from the group consisting of OH, NH$_2$, H and CH$_3$;
wherein L and M are selected from the group consisting of carbon and CH, the chemical bond between L and M is selected from the group consisting of a single bond and a double bond, L and M are carbon when the bond is a double bond, and L and M are CH when the bond is a single bond;
wherein $Z_4$, $Z_5$ and $Z_6$ are different and are selected from the group consisting of $R_4$, $R_5$ and

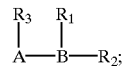

wherein A is selected from the group consisting of CH, sulfur and zero;

wherein B is selected from the group consisting of sulfur, sulfoxide, sulfone, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and a lower alkyl group;

wherein $R_5$ is selected from the group consisting of hydrogen and a lower alkyl group;

where $R_4$ is the same or different than $R_5$;

wherein each of said $R_4$, $R_5$ and

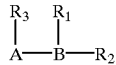

substituents is used once; and wherein each lower alkyl group is independently selected from the group consisting of lower alkyl groups having from about 1 to 6 carbons, In a preferred embodiment of formula 8, X and Y are $NH_2$, the bond between L and M is single, A is sulfur, B is carbon, $R_1$ is hydrogen, $R_2$ is phenyl and $R_3$ is zero.

The present invention is also directed to tricyclic [3,2-d] and [2,3-d]pyrimidine compounds, and pharmaceutically acceptable salts thereof, having the formula (10):

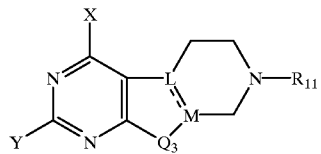

(10)

wherein X and Y are the same or different and are selected from the group consisting of OH, $NH_2$, H and $CH_3$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $R_{11}$ is selected from the group consisting of a lower alkyl group, an aryl group, p-aroyl-L-glutamate, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero;

$Q_3$ is selected from the group consisting of oxygen, NH, sulfur and $CH_2$.

In a preferred embodiment of formula 10, X and Y are $NH_2$, the bond between L and M is double, $Q_3$ is oxygen, and R is selected from the group consisting of phenyl, 3,4,5-trimethoxyphenyl, 3,5-dimethoxyphenyl, 2,4-dichlorophenyl, 3,4-dichlorophenyl, 2,6-dichlorophenyl and p-benzoyl-L-glutamate.

The present invention is also directed to a method for synthesizing the tricyclic pyrimidine compounds generally represented by formula (10). These methods generally include the steps of condensing a biselectrophile derived from a piperidone with a pyrimidine, preferably 2,4-diamino-6-hydroxy pyrimidine. Any compatible piperidone can be used; the piperdine chosen will depend on the final pyrimidine compound desired.

In a preferred method, the piperidone is 4-piperidone hydrochloride; protection of the piperidone is effected with ditertiary butyl-dicarbonate in DMF at room temperature. Bromination of this protected piperidine is then performed in chloroform at room temperature to yield a mixed product containing a bromopiperidine hydrobromide compound and an N-Boc brominated compound. These compounds are then condensed with a pyrimidine at room temperature for about 36 to 50 hours, preferably 48 hours. The resulting product is then reacted with the desired benzyl halide in anhydrous DMSO and anhydrous potassium carbonate for between about 48 and 72 hours at room temperature. Alternatively, the resulting product can be reacted with a benzoyl-L-glutamic acid diethyl ester instead of a benzyl halide.

The desired products of the above synthesis methods can be isolated using any purification means known in the art; chromatographic purification is preferred. The isolation of the products may be simplified by adding an excess of water to the reaction mixture and stirring at room temperature for between about 1 and 3 hours, which allows the products to separate.

The present invention is also directed to pyrido[2,3-d] and [3,2-d]pyrimidine compounds and pharmaceutically acceptable salts having the formula (11):

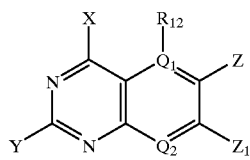

(11)

wherein X and Y may be the same or different and are selected from the group consisting of OH, $NH_2$, H and $CH_3$;

wherein Z and $Z_1$ are different and are selected from the group consisting of $R_4$ and

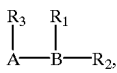

where Z is $R_4$ when $Z_1$ is

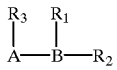

and Z is

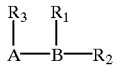

when $Z_1$ is $R_4$;

wherein $Q_1$ and $Q_2$ are the same or different and are selected from the group consisting of CH and nitrogen;

wherein A is selected from the group consisting of nitrogen, CH, sulfur and zero;

wherein B is selected from the group consisting of sulfur, sulfoxide, sulfone, CH, oxygen, nitrogen and zero; but B is not sulfur, sulfoxide, sulfone, oxygen or nitrogen when A is sulfur;

wherein $R_1$ is selected from the group consisting of hydrogen, a nitroso group, an aldehyde, a lower alkyl group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an aklyltriaryl group, a substituted diaryl group and a substituted triaryl group, and each substituent of the substituted aryl group, diaryl group, and triaryl group is the same or different and is selected from the group consisting of a lower alkyl group, an alkoxy, a substituted alkoxyaryloxy group, a halogen and zero;

wherein $R_3$ is selected from the group consisting of H, a lower alkyl and zero, and $R_3$ is zero when A is zero;

wherein $R_{12}$ is selected from the group consisting of hydrogen and methyl;

but $R_2$ is not 2,5-dimethoxyphenyl when X is $NH_2$, Y is $NH_2$, $Q_1$ is CH, $Q_2$ is N, $Z_1$ is H, B is CH, $R_1$ is H and $R_{12}$ is methyl; and wherein each lower alkyl group is independently selected from the group consisting of lower alkyl groups having from about 1 to 6 carbons.

In one embodiment of formula 11, X and Y are both $NH_2$, $Q_1$ is nitrogen, $Q_2$ is CH, $Z_1$ is hydrogen, A is zero, B is nitrogen, $R_1$ is hydrogen, $R_2$ is selected from the group consisting of phenyl, 2-methoxyphenyl, 4-methoxyphenyl, 4-chlorophenyl, 3,4-dimethoxyphenyl, 2,5-dimethoxyphenyl, 3,4,5-trimethoxyphenyl and 3,4-$C_4H_4$phenyl, $R_3$ is zero and $R_{12}$ is hydrogen.

In another embodiment of formula 11, X and Y are both $NH_2$, $Q_1$ is nitrogen, $Q_2$ is CH, $Z_1$ is hydrogen, A is zero, B is sulfur, $R_1$ is zero, $R_2$ is selected from the group consisting of 2-methoxyphenyl, 4-methoxyphenyl and 3,4-dimethoxyphenyl, $R_3$ is zero and $R_{12}$ is hydrogen.

In another embodiment of formula 11, X and Y are both $NH_2$, $Q_1$ is nitrogen, $Q_2$ is CH, $Z_1$ is hydrogen, A is zero, B is nitrogen, $R_1$ is methyl, $R_2$ is selected from the group consisting of 3,4,5-trimethoxyphenyl, 2,5-dimethoxyphenyl, 3,4-dimethoxyphenyl, 3,4,5-trimethoxyphenyl, phenyl, 3,4-$C_4H_4$phenyl and 2,3-$C_4H_4$phenyl, $R_3$ is zero and $R_{12}$ is hydrogen.

In another embodiment of formula 11, X and Y are both $NH_2$, $Q_1$ is nitrogen, $Q_2$ is CH, $Z_1$ is hydrogen, A is zero, B is sulfone, $R_1$ is zero, $R_2$ is selected from the group consisting of 2-methoxyphenyl, 4-methoxyphenyl, and 3,4-dimethoxyphenyl, $R_3$ is zero and $R_{12}$ is hydrogen.

The present invention is also directed to pyrido[2,3-] and [3,2-d]pyrimidine compounds and pharmaceutically acceptable salts having the formula (12):

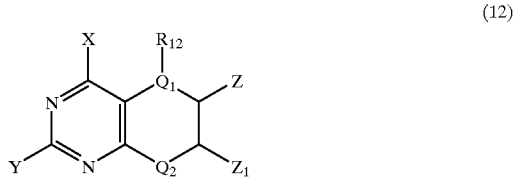

(12)

wherein X and Y may be the same or different and are selected from the group consisting of OH, $NH_2$, H and $CH_3$;

wherein Z and $Z_1$ are different and are selected from the group consisting of $R_4$ and

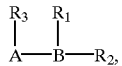

where Z is $R_4$ when $Z_1$ is

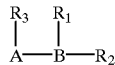

and Z is

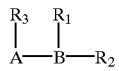

when $Z_1$ is $R_4$;

wherein $Q_1$ and $Q_2$ are the same or different and are selected from the group consisting of CH and nitrogen;

wherein A is selected from the group consisting of nitrogen, CH, sulfur and zero;

wherein B is selected from the group consisting of sulfur, sulfoxide, sulfone, CH, oxygen, nitrogen and zero; but B is not sulfur, sulfoxide, sulfone, oxygen or nitrogen when A is sulfur;

wherein $R_1$ is selected from the group consisting of hydrogen, a nitroso group, an aldehyde, a lower alkyl group, a formyl group and zero, and $R_1$ is zero when B is zero, oxygen, sulfur, sulfoxide or sulfone;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an aklyltriaryl group, a substituted diaryl group and a substituted triaryl group, and each substituent of the substituted aryl group, diaryl group, and triaryl group is the same or different and is selected from the group consisting of a lower alkyl group, an alkoxy, a substituted alkoxyaryloxy groug, a halogen and zero;

wherein $R_3$ is selected from the group consisting of H, a lower alkyl and zero, and $R_3$ is zero when A is zero;

wherein $R_{12}$ is selected from the group consisting of hydrogen and methyl; and wherein each lower alkyl group is independently selected from the group consisting of lower alkyl groups having from about 1 to 6 carbons.

For all of the formulas described above, the lower alkyl groups are the same or different and are independently selected from those lower alkyl groups having one to six carbon atoms, such as for example methyl, ethyl, propyl, butyl, pentyl, hexyl, cyclopropyl, cyclobutyl, cyclohexyl, cyclopropylmethyl or cyclobutylmethyl groups. Alkyl groups sharing one to about six carbon atoms are preferred. These lower alkyl groups are straight chain, branched chain or cyclic (alicyclic hydrocarbon) arrangements. The carbon atoms of these straight chain, branched chain or cyclic arranged alkyl groups may have one or more substituents for the hydrogens attached to the carbon atoms.

Suitable aryl groups include for example phenyl and benzyl groups. Suitable substituted aryl groups include for example: mono-, di- and tri-substituted alkoxy phenyl groups; mono-, di- and tri-halogenated phenyl groups; mono-, di and tri-substituted alkyl phenyl groups; mono-, di- and tri-substituted alkoxy benzyl groups and mono-, di- and tri-substituted halogenated benzyl groups.

The term "alkylaryl" refers to groups having an alkyl moiety attached to an aryl ring such as a phenyl or benzyl ring. The alkyl moiety is preferably a lower alkyl chain having one to about seven carbon atoms. This alkyl moiety may also contain oxygen, nitrogen or sulfur atoms, such as for example methoxy groups. The aryl moiety of the alkylaryl group is unsubstituted, mono-substituted, di-substituted or tri-substituted. If substituted, each substituent may independently be selected from the group consisting of a lower alkyl group having one to about seven carbon atoms, an alkoxy group such as for example a methoxy group and a halogen, such as for example fluorine, chlorine or bromine.

Other substituent groups in the formulas 1–11 as described above are as follows: the alkylaryl group is selected from the group consisting of an alkylphenyl and alkylbenzyl group; the alkyldiaryl group is selected from the group consisting of alkylnaphthyl, alkylbenzothiophene, alkylindene, alkylbenzofuran, alkylindole and alkylaminoquinoline; the alkyltriaryl group is an alkylanthracyl group; the substituted aryl, diaryl and triaryl group is selected from the group consisting of a mono-, di- and tri-substituted alkylphenyl and alkylbenzyl group, alkylnaphthyl, alkylbenzothiophene, alkylindole, alkylbenzofuran, alkylindene, alkylaminoquinoline, alkylanthracyl; each substituted alkyldiaryl and alkyltriaryl group is selected from the group consisting of a mono-, di- and tri-substituted alkylnaphthyl, alkylbenzothiophene, alkylindole, alkylbenzofuran, alkylindene, alkylaminoquinoline and alkylanthracyl group; and each substituent is the same or different and is selected from the group consisting of methyl, ethyl, n-propyl, n-butyl, branched n-pentyl, branched pentyl, n-hexyl, branched hexyl, cyclopropyl, cyclobutyl, cyclopentyl, cyclohexyl, methoxy group, chlorine atom, bromine atom and fluorine atom.

In some embodiments of this invention, the compounds, and pharmaceutically acceptable salts thereof, having the general formula 1, 2 and 4–11 wherein X and Y are each $NH_2$, $R_1$ is selected from the group consisting of H, $CH_3$ and CHO, $CH_3CHO$, and zero and R and $R_2$ are selected from the group consisting of 2,5-dimethoxyphenyl, 2,3,4-trimethoxyphenyl, 2,4,6-trimethoxyphenyl, naphthyl, 4-methoxynaphthyl, anthracyl and methoxy anthracyl, florene, benzothiophene, indene, benzofuran, indole, aminoquinoline, 2,3-dichlorophenyl, 2,4-dichlorophenyl, 2,5-dichlorophenyl, 2,6-dichlorophenyl, 3,4-dichlorophenyl and 3,5-dichlorophenyl. $R_3$ is $CH_3$ or hydrogen, $R_4$ is either hydrogen, methyl, ethyl, propyl and butyl group, cyclopropyl, cyclobutyl and cyclohexyl or zero, B is selected from the group consisting of nitrogen, carbon, sulfur and oxygen, A is selected from the group consisting of nitrogen, carbon and sulfur.

In other embodiments of this invention, compounds and pharmaceutically acceptable salts thereof, are provided having the formulas 1, 2 and 4–8 wherein X and Y are each $NH_2$. $R_1$ is selected from the group consisting of H, $CH_3$, NO and CHO, $CH_3CHO$, zero. R and $R_2$ are selected from the group consisting of 2-methoxyphenyl, 3-methoxyphenyl, 4-methoxyphenyl, 2,4-dimethoxyphenyl, 3,4-dimethoxyphenyl, 3–5-dimethoxyphenyl, 2-chlorophenyl, 3-chlorophenyl, 4-chlorophenyl, 2,3,4-trichlorophenyl, 2,4,5-trichlorophenyl, 2,4,6-trichlorophenyl, 3,4,5-trichlorophenyl, 2-bromophenyl, 3-bromophenyl, 4-bromophenyl, 2,4-dibromophenyl, 2,5-dibromophenyl, 2,6-dibromophenyl, 3,4-dibromophenyl, 3,5-dibromophenyl, 2,4,6-tribromophenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,4,5-trifluorophenyl, 2,4,6trifluorophenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, and 2,4,6-trimethylphenyl. $R_3$ is $CH_3$ or hydrogen, and in formulas 3–5. $R_4$ is selected from the group consisting of hydrogen, methyl, ethyl, propyl, and butyl group, cyclopropyl, cyclobutyl, cyclohexyl and zero. B is selected from the group consisting of nitrogen, carbon, sulfur and oxygen and A is selected from the group consisting of nitrogen, carbon and sulfur.

In other embodiments of this invention, compounds and pharmaceutically acceptable salts thereof, are provided having the formulas 1, 2 and 4–8 wherein X and Y are each $NH_2$. $R_1$ is selected from the group consisting of H, $CH_3$, NO and CHO, $CH_3CHO$, zero. R and $R_2$ are selected from the group consisting of methyl, ethyl, n-propyl, n-butyl, cyclopropyl, cyclobutyl, cyclopentyl, cyclohexyl, 2-methoxybenzyl, 3,4-dimethoxybenzyl, 2,3-dimethoxybenzyl, 3,4-dimethoxybenzyl, 2,3,4-trimethoxybenzyl, 3,4,5-trimethoxybenzyl, 2-chlorobenzyl, 3,4-dichlorobenzyl, 2,3-dichlorobenzyl, 2,4-dichlorobenzyl, 2,5-dichlorobenzyl, 2,6dichlorobenzyl, 2,6-dichlorobenzyl, 3,4-dichlorobenzyl, 3,5-dichlorobenzyl, 2-bromobenzyl, 3,4-dibromobenzyl, 2-fluorobenzyl, 3,4-difluorobenzyl, 2,4-difluorobenzyl, 2,5-difluorobenzyl, 2,6-difluiorobenzyl and 3,4-difluorobenzyl. $R_3$ is $CH_3$ and hydrogen, and in formulas 3–5 $R_4$ is selected from the group consisting of a hydrogen, methyl, ethyl, propyl, butyl group, cyclopropyl, cyclobutyl, cyclohexyl; B is selected from the group consisting of nitrogen, carbon, sulfur and oxygen; and A is selected from the group consisting of nitrogen, carbon and sulfur.

The present invention further relates to methods of using the above-described compounds, and pharmaceutically acceptable salts thereof, in therapeutically an/or prophylactically treating a patient with an illness. As used herein, the term "illness" refers to cancer, infection by *Pneumocystis carinii*, infection by *Toxoplasmosis gondii*, or other secondary infections arising in immunocompromised patients, such as those with AIDS, and infections caused by bacteria, malaria, fungi or protozoa.

A method of therapeutically treating a patient for an illness comprises the steps of:

a) employing a compound, or pharmaceutically acceptable salts thereof, having any of the above formulas 1, 2 or 4–11;

b) incorporating said compound in a suitable pharmaceutical carrier; and c) administering a therapeutically effective amount of said compound incorporated in said carrier to a patient.

As used herein, the term "suitable pharmaceutical carrier" refers to any pharmaceutical carrier known in the art, absent compatibility problems with the compounds of formula 1, 2 or 4–11. Preferred carriers include physiologic saline and 5% dextrose.

As used herein, the term "therapeutically effective amount" refers to that amount of any of said compounds of formulas 1, 2 or 4–11 incorporated in a suitable pharmaceutical carrier which is required to bring about a desired effect, such as reducing tumor size, destroying cancerous cells or resisting/treating infection caused by organisms such as Pneumocystis carinii and *Toxoplasmosis gondii*.

As will be understood by one skilled in the art, a therapeutically effective amount of said compound can be administered by any means known in the art, including but not limited to, injection, parenterally, orally, or, where appropriate, topically.

It is well within the skill of one practicing in the art to determine what dosage, and the frequency of this dosage, which will constitute a therapeutically effective amount for each individual patient, depending on the type of illness and the severity of such illness. It is also within the skill of one practicing in the art to select the most appropriate method of administering the compounds based upon the needs of each patient.

Methods of prophylactically treating a patient for an illness comprise the steps of:

a) employing a compound, or pharmaceutically acceptable salts thereof, having any of the formulas 1, 2 or 4–11 as described above;

b) incorporating said compound in a suitable pharmaceutical carrier; and c) administering a prophylactically effective amount of said compound incorporated in said carrier to a patient; wherein said illness is selected from the group consisting of infection caused by *Pneumocystis carinii* and *Toxoplasmosis gondii*.

As used herein, the term "prophylactically effective amount" refers to that amount of any of the compounds described above which will cause the body to generate antibodies in amounts sufficient to resist the onset of infection caused by *Pneumocystis carinii* or *Toxoplasmosis gondii* in immunocompromised patients.

As will be understood by one skilled in the art, a prophylactically effective amount of said compound can be administered by any means known in the art, including but not limited to, injection, parenterally, orally, or, where appropriate, topically.

It is well within the skill of one practicing in the art, to determine what dosage, and the frequency of this dosage, which will constitute a prophylactically effective amount for each individual patient, depending on the type of illness, such as the type of cancer, and the severity of such illness. It is also within the skill of one practicing in the art to select the most appropriate method of administering the compounds based upon the needs of each patient.

EXAMPLES

The following examples are set forth to illustrate various embodiments of the invention, and should not be construed as limiting the invention in any way. Standard test procedures familiar to those skilled in the art were used in the examples, such as those procedures described by Gangjee, A., et al., in "5-Arylthio-substituted 2-amino-4-oxo-6-methyl pyrrolo]2,3-d] pyrimidine antifolates as thymidylate synthase inhibitors and antitumor agents", *J. Med. Chem.*, Vol. 38, pp. 4495–4502 (1995); "Effect of bridge region variation on antifolate and antitumor activity of classical 5-substituted 2,4-diamino furo [2,3-d] pyrimidines", *J. Med. Chem.*, Vol. 38, pp. 3798–3805 (1995); and "Novel 2,4-diamino-5-substituted-pyrrolo[2,3-d]pyrimidines As Classical and Non-Classical Antifolate Inhibitors of Dihydrofolate Reductases", *J. Med. Chem.*, Vol. 38, pp. 2158–2165 (Jun. 6, 1995) and references disclosed therein.

Example I

Compounds 1–6, 8, 301 and 303–312 were evaluated as inhibitors of dihydrofolate reductase (DHFR) from *Pneumocystis carinii* (Pc), *Toxoplasmosis gondii* (Tg) and rat liver (RL). Performance of these compounds was compared with that of trimetrexate (TMQ), piritrexim (PTX), trimethoprim (TMP) and methotroxate (MTX), all of which are currently available. Trimetrexate is available from Warner-Lambert/Parke Davis Pharmaceutical Research, Ann Arbor, Mich. Trimetrexate is approved by the U.S. Food and Drug Administration as an approved new drug for the treatment of *Pneumocystis carinii* infections in patients with AIDS. PTX is an experimental anticancer agent in Phase II clinical trials and is also an agent against *Pneumocystis carinii* and *Toxoplasmosis gondii*. TMP is an agent used against *Pneumocystis carinii* infection in conjunction with sulfonamides. MTX is a clinical used anticancer agent.

The evaluations of Compounds 1–6, 8, 301 and 303–312 consisted of determining the $IC_{50}$ values and selectivity ratios of each compound against Pc DHFR, Tg DHFR and RL DHFR. The $IC_{50}$ value is the concentration of a compound required to inhibit the dihydrofolate reductase activity by 50 percent (%). It will be understood by those skilled in the art that the lower the $IC_{50}$ value the more potent the compound. The selectivity ratio is a measure of the selectivity of a compound for Pc DHFR or Tg DHFR and is expressed as the $IC_{50}$ value of the DHFR from rate liver (RL) divided by the $IC_{50}$ value of either the Pc DHFR or the Tg DHFR, depending on which organism the compounds are being tested against. For example, the selectivity ratio of a compound is calculated by the following formula:

$$\frac{IC_{50} \text{ RL DHFR}}{IC_{50} \text{ (Pc DHFR or Tg DHFR)}}$$

It will be understood by those skilled in the art that the higher the selectivity ratio, the less toxic the compound is to mammalian dihydrofolate reductase, and thus, less toxic to the patient.

Table 4 sets forth the $IC_{50}$ values for Pc DHFR, RL DHFR and Tg DHFR and the corresponding selectivity ratios for the compounds tested.

TABLE 4

Inhibitory Concentrations ($IC_{50}$ μM) and Selectivity Ratios

| Compound # | Pc DHFR[1] | RL DHFR[1] | Selectivity Ratio: RL DHFR/Pc DHFR | Tg DHFR[1] | Selectivity Ratio: RL DHFR/Tg |
|---|---|---|---|---|---|
| 1 | >23 | 56.3 | <2.4 | 8.1 | 7.0 |
| 2 | 119.0 | 116.0 | 1.0 | 4.3 | 27.0 |
| 3 | 279.0 | 63.0 | 0.23 | 6.0 | 10.5 |
| 4 | 45.7 | 156.0 | 3.4 | 1.7 | 92.0 |
| 5 | >21 | 70.0 | <3.3 | 5.3 | 13.2 |
| 6 | 35.3 | 14.4 | 0.4 | 1.4 | 10.3 |
| 8 | 252.0 | >252 | >1 | 3.9 | >65 |
| 9 | 0.038 | 0.044 | 1.20 | 0.21 | 0.21 |
| 301 | 307.0 | 59.3 | 0.2 | 1.1 | 53.9 |
| 303 | 81.0 | 4.2 | 0.05 | 1.4 | 3.0 |
| 304 | >12.0 | >12.0 | ND* | 3.4 | >4.0 |
| 305 | 28.90 | 3.0 | 0.11 | 1.0 | 3.0 |
| 306 | 209.0 | 8.20 | 0.04 | 0.87 | 9.43 |
| 307 | 11.10 | 16.7 | 1.50 | 2.60 | 6.42 |
| 308 | 58.50 | 5.30 | 0.09 | 11.6 | 0.46 |
| 309 | 10.60 | 3.00 | 0.28 | 0.81 | 3.70 |
| 310 | 929.0 | 82.9 | 0.09 | 9.20 | 9.01 |
| 312 | 0.044 | 0.06 | 1.36 | 0.15 | 0.40 |
| TMQ | 0.042 | 0.003 | 0.07 | 0.01 | 0.30 |
| PTX | 0.038 | 0.001 | 0.04 | 0.01 | 0.14 |
| TMP | 12.0 | 133.0 | 11.1 | 2.7 | 49.0 |
| MTX | 0.001 | 0.003 | 3.0 | 0.014 | 0.21 |

*ND = not determined

As can be seen from the above table, Compound 4 is almost two-times as selective at TMP and 306 times as selective as TMQ. Compound 8 similarly showed much higher selectivity than the compounds known in the art. These two compounds, therefore, represent preferred embodiments of the invention for the treatment of infections caused by *Pneumocystis carinii* and *Toxoplasmosis gondii* as well as in treatment of cancer patients as an antitumor agent or to destroy cancerous cells. With regard to *Pneumocystis carinii*, Compounds 4 and 8, with their high potency and high selectivity, may be used clinically with a lesser amount of a leucovorin as compared to TMQ or may be used clinically without the necessity of leucovorin, and thus greatly reduce the cost of administering these compounds to a patient.

Example 2

Compound 9 was tested for DHFR inhibition against the growth of human leukemia CCRF-CEM cells. The performance of Compound 9 was evaluated against NMX. Four different types of cells were used: CCRF-CEM cells were unaltered; R30dm cells had a decreased amount of polyglutamate synthase; R1 cells had a twenty-fold increase in wild type DHFR protein and activity; and R2 cells were deficient in their ability to uptake the compounds into the cell. Results are presented in Table 5 below.

TABLE 5

Growth Inhibition of Parental CCRF-CEM and Sublines with Single, Defined Mechanisms of MTX Resistance During Continuous (0–120 hours) Exposure to MTX and Compound 311 ($EC_{50}$ in nM)

| Compound | CCRF-CEM | R30dm | R1 | R2 |
|---|---|---|---|---|
| MTX | 14.5 ± 0.4 (n = 5) | 14.5 ± 0.5 (n = 2) | 595 ± 5 (n= 2) | 3100 ± 100 (n = 2) |
| 311 | 12.8 ± 2.2 (n = 5) | 36 ± 1 (n = 2) | 515 ± 25 (n= 2) | 1650 ± 200 (n = 2) |

Average values are presented ± the standard deviation range for n = 2 and ± the standard deviation range for n ≧ 3.

As can be seen from the results of the above table, Compound 9 performed comparably to MTX. The example further demonstrates that polyglutamylation may play a limited role in the mechanism of action of Compound 9, even in continuous exposure. Both the R1 subline, with amplified DHFR expression, and the MiX-transport deficient R2 subline displayed resistance to MTX under continuous exposure.

Example 3

Compound 9 and MTX were also tested for growth inhibition of A253 and FaDu human squamous carcinoma cell lines; neither of these cell lines had any deficiencies. Results are presented below in Table 6.

TABLE 6

Growth Inhibition of A253 and FaDu Human Squamous Carcinoma Cell Lines Following Continuous (120 hours) Exposure to MTX and Compound 311 ($EC_{50}$ in nM)

| Compound | A253 | FaDu |
|---|---|---|
| MTX | 17 ± 1 | 31 ± 2 |
| 311 | 46 ± 4 | 22 ± 4 |

All values are average ± standard deviation range for duplicate determinations.

Example 4

Compound 9 and aminopterin were further tested for their activity as substrates for human leukemia cell CCRF-CEM folylpolyglutamate synthetase. Aminopterin is a classical 2,4-diamino antifolate substrate. Results are presented below in Table 7.

TABLE 7

Activity of Aminopterin and Compound 9 as Substrates for CCRF-CEM Human Leukemia Cell Folylpolyglutamate synthetase

| Substrate | KM, μM | $V_{max, red}$ | $V_{max}/K_{m(red)}$ | n |
|---|---|---|---|---|
| Aminopterin | 4.3 ± 0.2 | 1 | 0.23 ± 0.01 | 3 |
| 9 | <1 | 0.72 ± 0.07 | >0.72 | 4 |

Values presented are average ± standard deviation.

This examples demonstrates that Compound 9 is a potent tumor cell growth inhibitor that shares determinates of response with MTX. It is similar in potency to MTX as an inhibitor of the growth of human leukemia and SCC cell lines in culture. DHFR is suggested as the target of Compound 9, which is supported by the data showing relatively potent DHFR inhibition in vitro and the cross-resistance to Compound 9 of a human cell line having amplified expression of DHFR. Compound 9 may also use the MTX/reduced folate-transport protein for uptake as evidenced by the cross-resistance of a human cell line in which this transport system is defective. This example indicates that Compound 9 may be an excellent substrate for human FPGS with a very low $K_m$. The slight cross-resistance to continuous exposure of the cell line having low levels of FPGS suggests that polyglutamate metabolites may play a role in growth inhibition even under these conditions.

Example 5

Compound 9 was further tested for its in vitro anti-cancer activity by the National Cancer Institute. Results are presented in Table 8 below. $GI_{50}$ represents the concentration at which growth was inhibited by 50%.

TABLE 8

In Vitro Anti-Cancer Activity of Compound 311

| Panel/Cell Line | $GI_{50}$ |
|---|---|
| Leukemia | |
| CCRF-CEM | ND |
| HL-60 (TB) | ND |
| MOLT-4 | ND |
| RPMI-8226 | ND |
| SR | >1.00E-04 |
| Non-Small Cell Lung Cancer | |
| A549/ATCC | <1.00E-08 |
| EKVX | 3.97E-05 |
| HOP-62 | <1.00E-08 |
| HOP-92 | 8.40E-06 |
| NCI-H226 | >1.00E-04 |
| NCI-H23 | 5.75E-08 |
| NCI-H322M | >1.00E-04 |
| NCI-H522 | >1.00E-04 |
| Colon Cancer | |
| COLO 205 | >1.00E-04 |
| HCC-2998 | <1.00E-08 |
| HCT-116 | <1.00E-08 |
| HCT-15 | <1.00E-08 |
| HT29 | <1.00E-08 |
| KM12 | 3.32E-05 |
| SW-620 | 3.15E-06 |
| CNS Cancer | |
| SF-268 | <1.00E-08 |
| SF-295 | <1.00E-08 |
| SF-539 | <1.00E-08 |
| SNB-19 | >1.00E-04 |
| SNB-75 | <1.00E-08 |
| U251 | <1.00E-08 |
| Melanoma | |
| LOX IMVI | <1.00E-08 |
| MALME-3M | <1.00E-08 |
| M14 | <1.00E-08 |
| SK-MEL-2 | >1.00E-04 |
| SK-MEL-28 | >1.00E-04 |
| UACC-257 | ND |
| UACC-62 | <1.00E-08 |
| Ovarian Cancer | |
| IGROV1 | <1.00E-08 |
| OVCAR-3 | >1.00E-04 |
| OVCAR-4 | >1.00E-04 |
| OVCAR-5 | >1.00E-04 |
| OVCAR-8 | <1.00E-08 |
| SK-OV-3 | >1.00E-04 |
| Renal Cancer | |
| 786-0 | <1.00E-08 |
| ACHN | <1.00E-08 |

TABLE 8-continued

In Vitro Anti-Cancer Activity of Compound 311

| Panel/Cell Line | $GI_{50}$ |
|---|---|
| CAKI-1 | <1.00E-08 |
| RXF 393 | >1.00E-04 |
| SN12C | <1.00E-08 |
| TK-10 | >1.00E-04 |
| UO-31 | <1.00E-08 |
| Prostate Cancer | |
| PC-3 | >1.00E-04 |
| DU-145 | 1.09E-08 |
| Breast Cancer | |
| MCF7 | <1.00E-08 |
| MCF7/ADR-RES | <1.00E-08 |
| MDA-MB-231/ATCC | >1.00E-04 |
| HS 578T | >1.00E-04 |
| MDA-MB-435 | 6.87E-07 |
| MDA-N | <1.00E-08 |
| BT-549 | >1.00E-04 |
| T-47D | >1.00E-04 |

As will be appreciated by one skilled in the art, the lower the $GI_{50}$, the more effective the compound. A $GI_{50}$ of less than $1.00 \times 10^{-8}$ indicates a very high potency, whereas a $GI_{50}$ greater than $1.00 \times 10^{-4}$ indicates that the compound was relatively inactive.

As demonstrated in Table 8 above, Compound 9 was shown to be highly selective against certain cell lines, with little or no activity against other cell lines. This result indicates that Compound 9 is not a general poison, but rather is very selective. For example, in the eight breast cancer cell lines, Compound 9 was found to be highly potent, with $GI_{50}$ of less than $1.00 \times 10^{-8}$ M, against the MCF7, MCF7-ADR-RES (resistant cell line) and the MDA-N cell lines, but was relatively inactive, with $GI_{50}$ greater than $1.00 \times 10^{-4}$ M against breast cancer cell lines MDA-MB-231/ATCC, HS578T, BT-549 and T47D. The difference in activity of these two sets of breast cancer cells is ten thousand fold, which indicates a very high degree of selectivity. This kind of selectivity is repeated in all of the cell lines tested.

Example 6

The inhibitory concentration of Compounds 313 and 314 against TS was determined. The performance of these compounds was measured against PDDF, which is a standard TS inhibitor and experimental anticancer agent. The compounds were all tested against *Lactobacillus casei* and human lymphoma cells. Results are presented in Table 9 below:

TABLE 9

Inhibitory Concentrations ($IC_{50}$ in $\mu M$) Against TS

| Compound | L. Casei TS | Human TS |
|---|---|---|
| 313 | 180 | 180 |
| 314 | 360 | ND |
| PDDF | 0.036 | 0.036 |

As can be seen from the above table, Compound 313 and 314, when tested, had surprisingly high inhibitory concentration when compared with that of PDDF.

Example 7

Compounds 315 and 317–322 were tested for their inhibitory activity against TS. The performance of these compounds was measured against ZD1694, which is in Phase III clinical trials as an antitumor agent. All of the compounds were tested against human cells, L. casei, E. coli, and S. faecium. Results are presented in the Table 10 below.

TABLE 10

Inhibitory Concentrations ($IC_{50}$ in $\mu M$) Against TS

| Compound | Human | L. Casei | E. Coli | S. Faecium |
|---|---|---|---|---|
| ZD1694 | 0.22 | 8.8 | 5.3 | 8.8 |
| 315 | >25 | >26 | ND | ND |
| 317 | 2.4 | >24 (33%) | >24 (30%) | >24 (12%) |
| 318 | 0.13 | 45 | 45 | >45 (31%) |
| 319 | 1.0 | >26 (0%) | >26 (40%) | 30 |
| 320 | 0.15 | 5.1 | 13 | 15 |
| 321 | 30 | >30 (0%) | >30 (30%) | >30 (20%) |
| 322 | 2.0 | >25 (32%) | >25 (36%) | >25 (0%) |

Example 8

Compounds 317–320 were also tested for their ability to inhibit DHFR. Selectivity ratios were determined as measured against *Pneumocystis carinii* (Pc), *Toxoplasmosis gondii* (Tg) and rat liver (RL). Results are presented in Table 11 below.

TABLE 11

Inhibition of Dihydrofolate Reductase ($IC_{50}$ in $\mu M$)

| Compound | Pc | RL | Selectivity Ratio RL/Pc | Tg | Selectivity Ratio RL/Tg |
|---|---|---|---|---|---|
| 317 | >21 | >21 | ND | 20 | >1 |
| 318 | >20 | >20 | ND | 11.7 | >1.7 |
| 319 | 40 | 24.6 | 0.62 | 3.1 | 7.94 |
| 320 | >15 | 7470 | ND | 244 | 30.61 |

As can be seen from Table 11, Compound 320 is highly selective for *Toxoplasmosis gondii* DHFR.

Example 9

Compounds 317–322 were also tested for their ability to inhibit the growth of FaDu human squamous cell carcinoma cell lines. The performance of these compounds was tested against PDDF, and AG331, which is a TS inhibitor in Phase III clinical trials as an antitumor agent. Results are presented in Table 12 below.

TABLE 12

Growth Inhibition of the FaDu Human Squamous Cell Carcinoma Cell Line By Continuous (120 hours) Exposure to the Inhibitors

| Compound | $EC_{50}$ $\mu M$ | n |
|---|---|---|
| 317 | >10 | 2 |
| 318 | insoluble | — |
| 319 | 6.7 ± 1.5 | 3 |
| 320 | 1.5 ± 0.4 | 3 |
| 321 | >10 | 2 |
| 322 | ND | — |
| PDDF | 1.7 ± 0.2 | 4 |
| AG331 | 1.0 ± 0.1 | 6 |

Values presented are average ± standard deviation.

Example 10

The following example describes methods of synthesizing the compounds represented by formula 2. These methods are illustrated in FIG. 1. Reference numerals and letters correspond with those of FIGS. 1 and 2.

2-amino-3,4-dicyanopyrrole (11)

A mixture of about 4.0 grams (g) of Compound 10, about 4.0 g of 5% Pd on $BaCO_3$, about 15 milliliters (ml) of DMF and about 25 ml methanol was hydrogenated at about 50 psi for approximately 3 hours. The mixture was filtered through Celite®, a filtering composition commercially available from Johns-Mannville Products Corporation, and the filtrate concentrated under reduced pressure to about 10 ml. About 200 ml of cold water was added to the concentrate, and a light brown solid was formed. This solid was collected by filtration to yield about 1.60 g of Compound 11.

2,4-diamino-5-cyanoprrolo[2,3-d]pyrimidine (12)

A mixture of about 2.63 g of Compound 11 and about 2.5 g of chlorformamidine hydrochloride in about 50 ml Dowtherm-A®, a liquid heat transfer media commercial available from Dow Chemical Company, was heated at between about 160° and 170° C. for approximately 48 hours, until Compound 11 could not be detected by thin layer chromatography (TLC). The mixture was cooled to room temperature, and about 50 ml of $Et_2O$ was added thereto. A greenish-brown solid resulted. The solid was filtered and washed with $Et_2O$ to yield about 3.0 g of Compound 12.

2,4-diaminopyrrolo[2,3-d]pyrimidine-5-carboxaldehyde (13)

About 6.0 g of Raney Ni was added to a stirred solution of about 2.0 g of Compound 12 and about 50 ml of HCOOH. The mixture was heated to about 80° C. for about 2 hours, until no starting material could be detected by TLC. The mixture was cooled to room temperature and filtered through Celite®. The filtrate was evaporated under reduced pressure, azeotroping with methanol to remove traces of HCOOH. The residue was dissolved in about 25 ml of hot water, treated with Norit®, an activated adsorption carbon commercially available from American Norit Company, Inc., and filtered through Celite®. The filtrate was neutralized with $NH_4OH$. The light brown precipitate which resulted was filtered and dried to yield about 1.40 g of Compound 13, which was immediately used in subsequent reactions without further purification.

2,4-diamino-5[[N-(3',4',5'-trimethoxyphenyl)imino]methyl]pyrrolo]2,3-d]pyrimidine (14a)

A solution containing about 1.30 g of Compound 12 and about 2.06 g of 3,4,5-trimethoxyaniline in about 75 ml of 70% acetic acid and containing about 6.50 g of damp Raney Ni was hydrogenated at atmospheric pressure for about 24 hours at room temperature. The mixture was treated with Norit® and filtered through Celite® and the solvent removed from the filtrate by evaporation under reduced pressure. About 15 ml of cold water was added to the residue, and the suspension was added to about 100 ml of a stirred, cold, saturated solution of $NaHCO_3$. The mixture was stirred for about 10 minutes and refrigerated for about 6 hours. The brown precipitate which formed was collected, washed with water, and dried. This product, containing Compound 14A, was washed repeatedly with $Et_2O$ until no aniline was detected by TLC in the washings. The residue was then dissolved in about 100 ml methanol and filtered, and the filtrate evaporated under reduced pressure to near dryness. About 50 ml $Et_2O$ was added to the solution, and the precipitate filtered to yield about 1.20 g of Compound 15a.

2,4-diamino-5-[(3',4',5'-trimethoxyanilino)methyl] pyrrolo[2,3-d]pyrimidine(1)

About 0.05 g NaCNBH$_3$ were added to a solution containing about 0.20 g of Compound 15a in about 25 ml methanol. The pH was adjusted to about 2 with a 50% methanol/hydrochloric acid solution. The mixture was continuously stirred at room temperature for about 4 hours. The solvent was evaporated to dryness, and cold water was added to the residue, which was neutralized with NH$_4$OH. The resulting precipitate was filtered, dried, and dissolved in a 9:1 mixture of CHCl$_3$/methanol. This was applied to a silica gel column (2.4cm×20 cm) packed in CHCl$_3$. The column was eluted with a gradient of 1% methanol in CHCl$_3$ to 15% methanol in CHCl$_3$. Fractions corresponding to the product, as determined by TLC, were pooled and evaporated to dryness under reduced pressure. The residue was triturated in cold Et$_2$O and filtered to yield about 010 g of Compound 1.

2,4-diamino-5-[(3',4'-dimethoxyanilino)methyl] pyrrolo[2,3-d]pyrimidine (2)

The Schiff base was prepared as described for Compound 15a, except that the reaction was carried out in 80% acetic acid and using 3,4-dimethokyaniline to yield about 1.20 g of Compound 15b. Reduction of Compound 15b was carried out as described for Compound 1. The crude product was dissolved in methanol and filtered. The filtrate was evaporated under reduced pressure to dryness. The residue was triturated in cold Et$_2$O and filtered to yield about 0.51 g of Compound 2.

2,4-diamino-5-[(4'-methoxyanilino)methvyl]pyrrolo [2,3-d]pyrimidine (3)

The Schiff base was prepared as described above for Compound 15b using 4-methoxyaniline to yield about 0.32 g of Compound 15c. Reduction of Compound 15c was carried out as described for Compound 15b to yield Compound 3.

2,4-diamino-5-[(2',5'-dimethoxvanilino)methyl] pyrrolo[2.3-d]pyrimidine (4)

The Schiff base was prepared as described above for Compound 15b using 2,5-dimethoxyaniline to yield about 0.90 g of Compound 15d. Reduction of Compound 15d was carried out as described above for Compound 15b to yield about 0.25 g of Compound 4.

2,4-diamino-5-[[(2',5'-diethoxyphenyl) iminolmethyl]-pyrrolo[2,3-d]pyrimidine(15e)

Method A, starting from Compound 13: A solution of about 1.15 g of Compound 13 and about 1.76 g of 2,5-diethoxyaniline (14e) in about 75 ml 70% acetic acid containing about 5.75 g of damp Raney Ni was hydrogenated at about 55 psi for about 12 hours at room temperature. The mixture was filtered through Celite® and the filtrate evaporated under reduced pressure. About 15 ml cold water were added to the residue and this suspension was added to about 100 ml of a stirred, cold, saturated solution of NaHCO$_3$. The mixture was stirred for an additional 10 minutes and refrigerated for about 4 hours. The brown precipitate which resulted was collected, washed with water, and dried. The crude product containing Compound 14e was washed repeatedly with Et$_2$O until no aniline could be detected by TLC in the washings. The residue was then dissolved in about 100 ml methanol and filtered, and the filtrate evaporated to dryness under reduced pressure. About 20 ml Et$_2$O was added to the solution, and the precipitate filtered to yield about 1.20 g of Compound 15e.

Method B, starting from Compound 12: The Schiff base was prepared as described above for Compound 15b using 2,5-diethoxyaniline to yield about 0.90 g of Compound 15e, which was identical in all respects with the sample prepared according to Method A described above.

2,4-diamino-5-[(2',5'-diethoxyanilino)methyllpyrrolo [2,3-d]pyrimidine (5)

Reduction of Compound 15e was performed as described above for Compound 15b to yield about 0.36 g of Compound 5.

2,4-diamino-5-[(3',4'-dichloroanilino)methyl]pyrrolo [2,3-d]pyrimidine (6)

The Schiff base was prepared as described above for Compound 15b using 3,4-dichloroaniline to yield about 1.0 g of Compound 15f. Reduction of Compound 15f was performed as described above for Compound 15b to yield about 0.34 g of Compound 6.

2,4-diamino-5-[(1'-naphthylamino)methyl]pyrrolo[2, 3-d]pyrimidine (7)

The Schiff base was prepared as described above for Compound 15b, except that the reaction was carried out at about 30 psi for about 12 hours at room temperature using 1-aminonaphthylene to yield about 0.92 g of Compound 15 g. Reduction of Compound 15 g was carried out as described above for Compound 15b, except that glacial acetic acid was used to adjust the pH to about 2. Crude product 7 was dissolved in a 9:1 mixture of CHCl$_3$/methanol, which was loaded on a silica gel column (2.4cm×20cm) packed in CHCl$_3$. The column was eluted with a gradient of 1% methanol in CHCl$_3$ to 5% methanol in CHCl$_3$. Fractions corresponding to the product, as determined by TLC, were pooled and evaporated under reduced pressure to dryness. The residue was triturated in cold Et$_2$O and the suspension filtered to yield about 0.24 g of Compound 7.

2,4-diamino-5-(anilinomethyl)pyrrolo[2,3-d] pyrimidine (8)

The Schiff base was prepared as described above for Compound 15b using aniline to yield about 0.69 g of Compound 15h. Reduction of Compound 15h was carried out as described for Compound 15b, except that glacial acetic acid was used to adjust the pH to about 2. About 0. 19 g of Compound 8 resulted.

N-[4-[N-](2,4-diaminopyrrolo[2,3-d]pyrimidin-5-yl) methyl]amino]benzoyl]-L-glutamic acid (9)

The Schiff base was prepared as described above for Compound 15b using diethyl(p-aminobenzoyl)-L-glutamate to yield about 1.39 g of the diethylester of Compound 16. Reduction of Compound 16 was carried out as described above for Compound 15b to yield about 0.44 g of Compound 17. Hydrolysis of the esters was carried out by stirring a solution of about 0.30 g Compound 17 in about 10 ml of 1N sodium hydroxide and 10 ml methanol for about 72 hours at room temperature. The solvent was evaporated to 5 ml, and the mixture was carefully acidified with glacial acetic acid in an ice bath. The tan precipitate which resulted was filtered, washed with water, and dried to yield about 0.23 g of Compound 9.

Example 11

The DHFR inhibitory concentrations of Compounds 159–169, 171, 172, 175, 177, 178, and 179 was determined. Performance of these compounds was measured against TMQ and TMP. Inhibitory concentration was measured against *Pneumocystis carinii* and *Toxoplasmosis gondii*, as well as rat liver. Results are presented in Table 13 below.

TABLE 13

Inihibitory Concentrations (IC$_{50}$, μM) and Selectivity Ratios of 5-subsituted furo[2,3-d]pyrimidines

| Compound # | Pc DHFR | RL DHFR | Selectivity Ratio RL/Pc | Tg DHFR | Selectivity Ratio RL/Tg |
|---|---|---|---|---|---|
| 159 | >26 | 252 | ND | >26 | ND |
| 160 | 19 | 23 | 1.2 | 19 | 1.2 |
| 161 | 0.65 | 12.3 | 18.9 | 11.6 | 1.1 |
| 162 | 13.5 | 12 | 0.89 | 37 | 0.32 |
| 163 | 41 | 36.5 | 0.89 | 38 | 0.96 |
| 164 | 14 | 60.3 | 4.31 | >42 | ND |
| 165 | >12 | >12 | ND | >12 | ND |
| 166 | 8.1 | 16.2 | 2.00 | 32.4 | 0.50 |
| 167 | 7.7 | 187 | 17.79 | 45.4 | 3.02 |
| 169 | 50.9 | 71.9 | 1.4 | >47 | ND |
| 171 | 44.8 | >27 | ND | >27 | ND |
| 172 | 284 | 34.3 | 0.1 | 21.5 | 1.6 |
| 175 | >31.3 | >31.3 | ND | >31.3 | ND |
| 177 | 8.6 | >83 | >10 | >83 | ND |
| 178 | >12 | >12 | ND | >12 | ND |
| 179 | >27.9 | >27.9 | ND | >27.9 | ND |
| TMQ | 0.042 | 0.003 | 0.07 | 0.01 | 0.30 |
| TMP | 12 | 133 | 11.1 | 2.7 | 49.0 |

As can be seen from the above table, Compound 161 is approximately 18 times more active than TMP and 1.7 times more selective; Compound 161 is 271 times more selective than TMQ and only 15 times less potent. These compounds, therefore, exhibit high selectivity for Pc DHFR. Compound 167 was also more selective than the compounds known in the art.

Example 12

Figure 6:
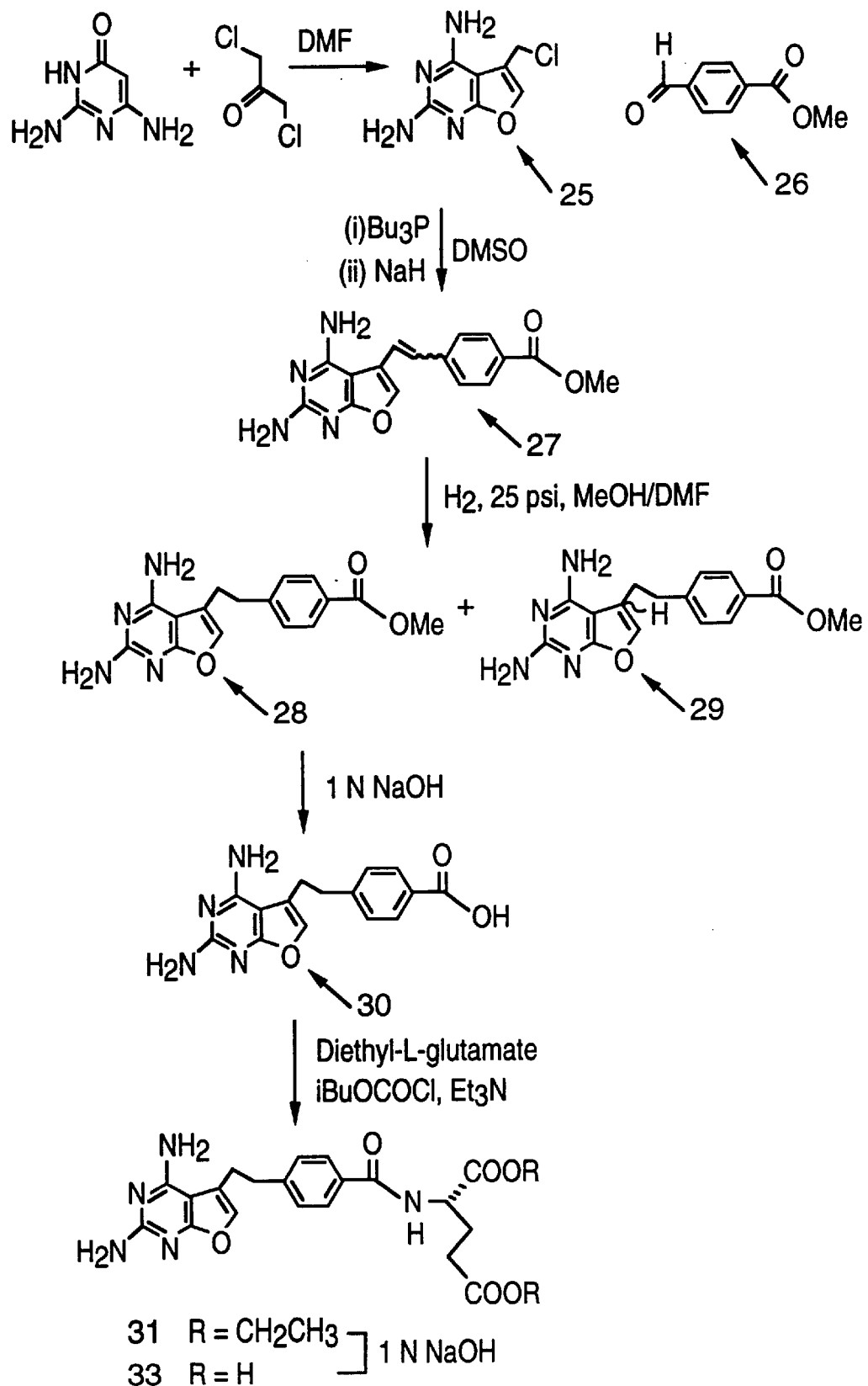
FIG. 6 shows a schematic diagram of the methods of preparing two of compounds having formula 4.
Figure 7:
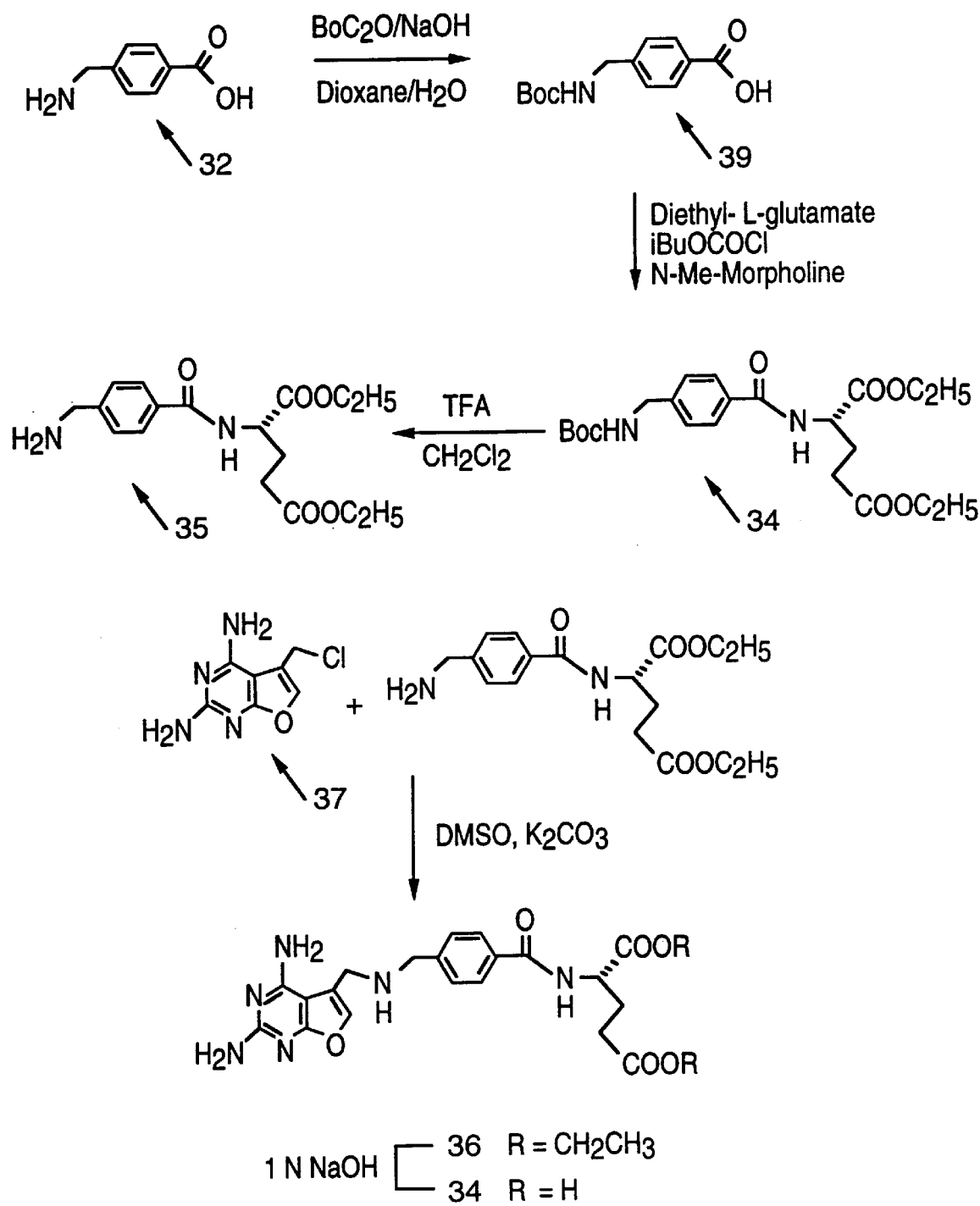
FIG. 7 shows a schematic diagram of the methods of preparing two of compounds having formula 4.
Figure 8:
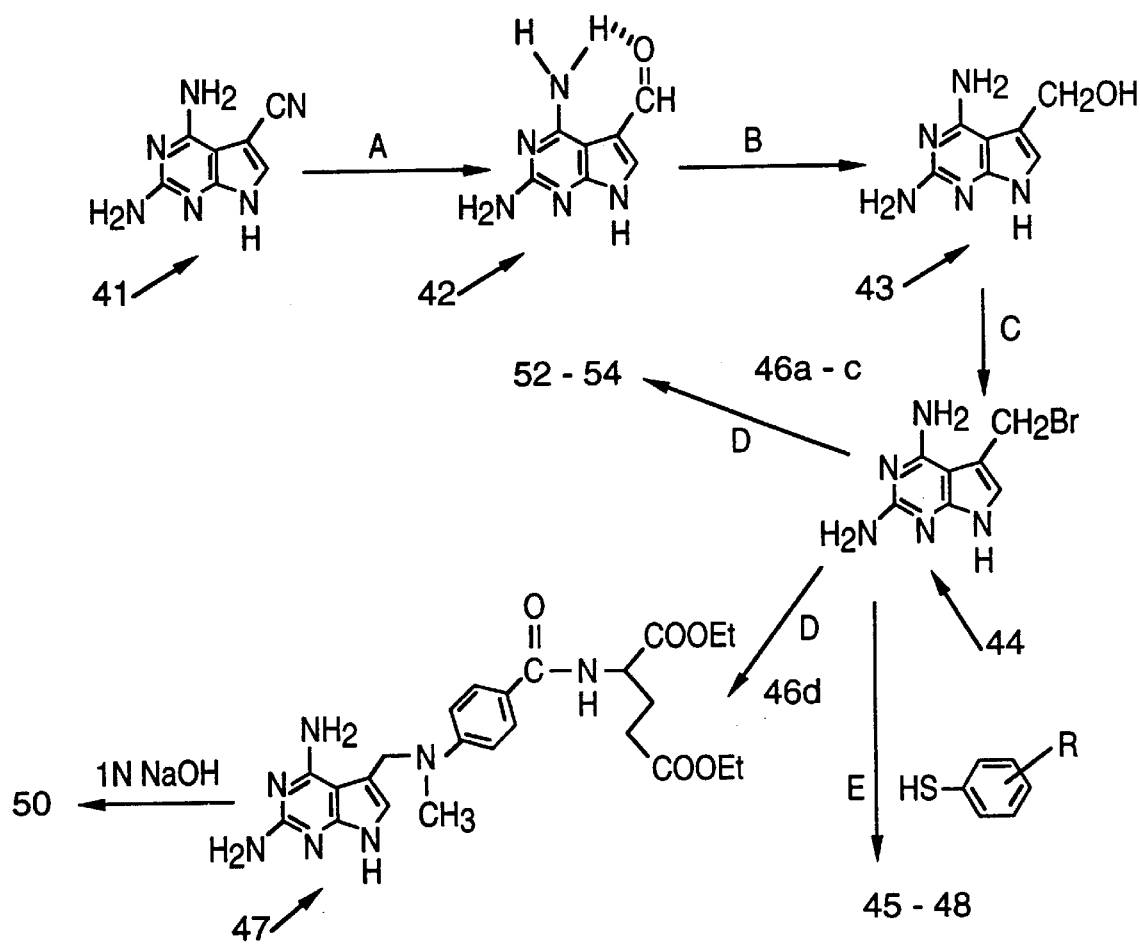
FIG. 8 shows a schematic diagram of the methods of preparing compounds having formula 9.

The following example provides methods for synthesizing compounds of formula 4. Reference numerals correspond with those in FIGS. 6 and 7.

Methyl 4-[2-(2,4-diaminofuro[2,3-d]pyrimidin-5-yl)-ethanvl]benzoate(27)

About 2.64 g of tributylphosphine was added to a solution containing about 0.79 g of 2,4-diamino-5(chloromethyl)furo[2,34pyrimidine (25) in about 10 ml anhydrous DMSO. The mixture was stirred at about 60° C. for about 2 hours under nitrogen to form the phosphonium salt. The solution was cooled to room temperature, at which time 0.35 g of sodium hydride (60% dispersion in mineral oil) followed by about 0.72 g of methyl 4-formylbenzoate (26) was added. The mixture was stirred for about 24 hours at room temperature. The DMSO was removed by vacuum distillation. About 50 ml of ethylether was added to the residue and the supernatant decanted after 10 minutes. About 50 ml of ethylether was added again, the residue stirred for about 1 hour, and the supernatant decanted. This process was repeated 3 more times; the mixture was then stored at 0° C. with about 50 ml ethylether. After about 18 hours, the mixture was ultrasonicated for 2 hours and cooled to 0° C. for a period of about 10 hours. The resulting solid was filtered, washed with ethylether, air dried, washed with water and air dried again. The solid was then suspended in about 250 ml of hot methanol. About 3 g of silica gel were added to the filtrate, and the suspension was evaporated to dryness under reduced pressure. The silica gel plug was loaded on a dry silica gel column (2.4×20cm) and flushed initially with CHCl$_3$ (500 ml). The column was then eluted sequentially with 100 ml portions of 1% to 8% methanol in CHCl$_3$. Fractions which showed a major spot at R$_f$ 0.66, as determined by TLC, were pooled and evaporated to dryness. The resulting residue was dissolved in glacial acetic acid and evaporated to dryness. This residue was redissolved in hot methanol and the solution stored at 0° C. for about 72 hours. The resulting solid was filtered, washed with ether, and dried to yield about 0.52 g of Compound 27.

Methyl 4-[2-(2,4-diaminofuro[2,3-d]pyrimidin-5-yl) ethyl]benzoate(28) and (+)-methyl 4-]2-(2,4-diamino-5,6-dihydrofuro2,3pyrimidin-5-yl)ethyl]benzoate (29)

About 0.31 g of 5% palladium on carbon was added to a solution containing about 0.155 g of Compound 27 in about 20 ml of a 1:1 mixture of methanol/DMF. The suspension was hydrogenated in a Parr apparatus at room temperature and 25 psi of hydrogen pressure for 30 minutes. The reaction mixture was filtered through Celite®, and the catalyst was washed with about 30 ml of a 1:1 methanol/DMF mixture. The filtrate was evaporated to dryness under reduced pressure, and the residue dissolved in about 100 ml methanol. About 500 mg of silica gel was added to the solution, and evaporated to dryness. The silica gel plug was loaded on a dry silica gel column (2.4×1cm) and flushed with about 500 ml CHCl$_3$. The column was then eluted with a gradient of 1–9% methanol in CHCl$_3$, collecting 15 ml fractions. Fractions showing a single spot at R$_f$ 0.63, as determined by TLC, were pooled and evaporated to dryness, and the residue was stirred in ether, filtered, and dried to yield about 0.08 g of Compound 28. Later fractions from the column described above, showing a single spot at R$_f$ 0.52, were pooled and evaporated to dryness under reduced pressure, and the residue obtained was stirred in ether, filtered, and dried to yield about 0.02 g of Compound 29.

4-[2-(2,4-diaminofuro[2,3-d]pyrimidin-5-yl)ethyl] benzoicacid (30)

About 1.5 ml of 1N sodium hydroxide was added to a solution containing about 0.065 g of Compound 28 in about 10 ml of a mixture of 2:1 methanol/DMSO. The mixture was stirred at room temperature for 18 hours and evaporated to dryness under reduced pressure (oil pump). The residue was dissolved in about 5 ml water and 1N HCl was added dropwise to bring the pH of the solution to 5.5. The suspension was cooled to 5° C. for about 12 hours and filtered. The residue was washed sequentially with water, acetone and ether and dried to yield about 0.05 g of Compound 30.

N-[4-[2-(2,4-diaminofuro[2,3-d]pyrimidin-5-yl) ethyl-benzoyl]-L-glutamic acid (33)

About 45 microliters of triethylamine was added to a suspension containing about 0.047 g of Compound 30 in about 3 ml anhydrous DMF, and the mixture stirred under nitrogen at room temperature for about 5 minutes. The solution was cooled to 0° C., about 42 microliters of isobutylchloroformate was added, and the mixture stirred at 0° C. for 30 minutes. About 0.077 g of diethyl-L-glutamate hydrochloride was added to the reaction mixture, followed immediately by about 45 microliters triethylamine. The mixture was slowly allowed to warm to room temperature, and stirred under nitrogen for a period of about 18 hours. The reaction mixture was then subjected to another cycle of activation using ½ of the quantities listed above. The reaction mixture was warmed to room temperature and stirred for 24 hours and evaporated to dryness under reduced pressure. The residue was dissolved in a 4:1 mixture of $CHCl_3$/methanol and chromatographed on a silica gel column (2.4×15cm), packed with $CHCl_3$/methanol (24:1), eluting with 24:1 $CHCl_3$/methanol. Fractions showing a single spot were pooled and evaporated to dryness. The residue was stirred in cold anhydrous ether and filtered to obtain about 0.054 g of Compound 31. About 1 ml of 1N sodium hydroxide was added to a solution containing about 0.052 g of Compound 31 in about 5 ml methanol and the solution stirred at room temperature for 24 hours. The methanol was evaporated under reduced pressure, the residue dissolved in about 5 ml water, and stirring was continued for an additional 24 hours. The pH of the solution was then adjusted to 4.0 by dropwise addition of 1N HCl. The resulting suspension was stored at 5° C. for about 12 hours and filtered; the residue was washed well with water and acetone and dried to yield about 0.044 g of Compound 33.

4-[[N-(tert-butyloxycarbonyl)amino]methyl]benzoic acid (39)

About 10 ml of 1N sodium hydroxide was added to a solution containing about 1.51 g of 4-(aminomethyl)benzoic acid (32) in about 20 ml of 1:1 dioxane/water. The mixture was stirred at room temperature for about 12 hours, and evaporated to half of its original volume under reduced pressure. The pH of the solution was adjusted to 3 by dropwise addition of 50% aqueous HCl, while maintaining the temperature below 10° C. with an ice bath. The resulting suspension was diluted with water (70 ml) and extracted with ethylacetate (3×50 ml). The combined organic layers were washed with about 50 ml saturated NaCl, dried $MgSO_4$, and filtered. The filtrate was evaporated to dryness under reduced pressure and the residue recrystallized from a mixture of ethylacetate/hexanes to yield about 2.10 g of Compound 39.

Diethyl-N-[4-[N-(tert-butyloxycarbonyl)amino]methyl]benzoyl]-L-glutamate (34)

A solution containing about 1.26 g of Compound 39 in about 20 ml anhydrous DMF under nitrogen was cooled in an ice-salt bath. About 0.55 ml of N-methylmorpholin was added to the cooled solution, followed 5 minutes later by about 0.65 ml isobutylchloroformate. After stirring for a period of about 20 minutes, 1.20 g diethyl-L-glutamate hydrochloride was added, followed immediately by about 0.55 ml N-methylmorpholin. The reaction mixture was warmed to room temperature and stirred for 12 hours. At this time, the activation cycle was repeated using ½ the amounts of reagents indicated above, after which the reaction mixture was warmed to room temperature and stirred for an additional 12 hours. The solvents were removed under reduced pressure, and the residue was dissolved in about 100 ml $CH_2Cl_2$, washed with about 75 ml water, 50 ml 0.1 NHCl, and about 50 ml saturated NaCl. The organic layers were dried ($MgSO_4$) and filtered. The filtrate was evaporated under reduced pressure and the residue was flash chromatographed on silica gel (2.4×24cm), eluting first with $CH_2Cl_2$ and then with 1 % methanol in $CH_2Cl_2$. Fractions showing a single spot corresponding to the product were pooled and evaporated under reduced pressure to yield about 1.29 g of Compound 34.

Diethyl N-[4-(aminomethyl)benzoyl]-L-glutamate (35)

About 1.8 ml trifluoroacetic acid was added dropwise to a stirred solution containing about 1.0 g of Compound 34 in about 20 ml $CH_2Cl_2$. The mixture was stirred at room temperature for 15 minutes, evaporated to dryness under reduced pressure, and co-evaporated twice with about 30 ml absolute ethanol. The residue was then subjected to column chromatography on silica gel (1.5×15cm), eluting with a gradient of 5–10% methanol in $CHCl_3$ to yield about 0.68 g of Compound 35.

Diethyl N-[4-[N-](2,4-diaminofuro[2,3-d]pyrimidin-5-yl)methyl(amino)methylllenzoyl)-L-glutamate (37)

About 0.28 g of anhydrous $K_2CO_3$ and about 0.67 g of Compound 35 were added to a solution containing about 0.2 g of Compound 35 in about 3 ml anhydrous DMSO. The reaction mixture was stirred under nitrogen at room temperature for 24 hours. The temperature was then raised to about 45° C. and the reaction continued for an additional 48 hours. The reaction mixture was then cooled to room temperature, diluted with about 50 ml water and stirred for about 8 hours. The solid that separated was filtered, washed with water, air dried, and dissolved in methanol. About 1 g of silica gel was added to the solution and the suspension evaporated to dryness under reduced pressure. The silica plug was loaded on a dry silica gel column (2.4×17 cm) and eluted with a gradient of 1–7% methanol in $CHCl_3$. Fractions corresponding to the product were pooled and evaporated to dryness. The residue was triturated with cold anhydrous ether to yield about 0.25 g of Compound 37.

N-[4-[[N-1(2,4-diaminofuro[2,3-dipyrimidin-5-yl) methyl]amino]methyl]benzoyl]-L-glutamic acid (34)

About 1 ml of 1N sodium hydroxide was added to a solution containing about 0.1 g of Compound 37 in about 10 ml of 2:1 methanol/THF. The mixture was stirred at room temperature for about 24 hours. The volatiles were removed under reduced pressure, and the residue dissolved in about 5 ml water and stirred for an additional 24 hours. The solution was cooled in an ice bath and the pH adjusted carefully to 4.0 by dropwise addition of 1N HCl. The precipitate was collected by filtration, washed well with water and ether, and immediately dried under high vacuum to yield about 0.08 g of Compound 34.

Example 13

Compounds 33 and 34 were evaluated as inhibitors of *Lactobacillus casei* DHFR, human recombinant (REC) DHFR and DHFR isolated from human CCRF-CEM. leukemic cells. The performance of these compounds was compared with that of MTX. The compounds were also evaluated as inhibitors of *L. casei* TS and human recombinant TS. The results are presented in Table 14 below.

TABLE 14

Inihibitory Concentrations ($IC_{50}$ in $\mu M$)

| Compound | Human REC DHFR | L. casei DHFR | CCRF-CEM DHFR | Human REC TS | L. casei TS |
|---|---|---|---|---|---|
| 33 | 1.0 | 0.1 | 0.25 | 220 | 200 |
| 34 | >200 | >200 | 30.5 | 63.0 | >200 |
| MTX | 0.004 | 0.006 | 0.0007 | 170 | ND |

Example 14

Compounds 33 and 34 were also evaluated for their substrate activity in CCRF-CEM human leukemia folylpolyglutamate synthetase; the compounds were compared against aminopterin. Results are presented in Table 15 below.

TABLE 15

Substrate Activity of Compounds 33 and 34 for CCRF-CEM Human Leukemia Cell Folypolyglutamate Synthetase

| Substrate | $K_m$, $\mu M$ | $V_{max(rel)}$ | $V_{max}/K_{m(rel)}$ |
|---|---|---|---|
| Aminopterin | 4.8 ± 0.7 (N = 6) | 1 (N = 6) | 0.21 ± 0.04 (N = 6) |
| 33 | 8.5 ± 2.1 (N = 3) | 0.65 ± 0.01 (N = 3) | 0.07 ± 0.02 (N = 3) |
| 34 | ND | 0.6 (N = 5) | ND |

Example 15

Compounds 33 and 34 were also tested for their growth inhibition of human T-lymphoblastic leukemia cell line CCRF-CEM, its MTX-resistance subline (R30dm), and human squamous cell carcinoma cell lines (FaDu and A235). The performance of these compounds was evaluated against MTX. Results are presented in Table 16 below.

TABLE 16

Growth Inhibition ($EC_{50}$, $\mu M$) During Continuous Exposure (0 to 120 hours)

| Compound | CCRF-CEM | R30DM | FaDu | A253 |
|---|---|---|---|---|
| 33 | 0.29 ± 0.01 (N = 3) | 4.25 ± 0.05 (N = 2) | 0.018 ± 0.02 (N = 2) | 0.54 ± 0.09 (N = 3) |
| 34 | 48.0 ± 23.0 (N = 2) | ND | ND | ND |
| MTX | 0.014 ± 0.001 (N = 10) | 0.018 ± 0.003 (N = 5) | 0.017 ± 0.002 (N = 5) | 0.013 ± 0.0008 (N = 3) |

Average values are presented ± range for N = 2 and ± standard deviation for N ≧ 3.

Example 16

The following example provides methods for preparing the pyrido[2,3-d]pyrimidine compounds and pharmaceutically acceptable salts thereof as described above. Reference letters and numerals correspond with those in FIG. 13. Guanidine (FIG. 13b) is condensed with 2-amino-3,5-dicarbonitrile-4-$R_{13}$-pyridine (FIG. 13a), wherein $R_{13}$ is a lower alkyl group having one to about seven carbon atoms as described herein, in refluxing ethyl alcohol to produce 2,4-diaminopyrido[2,3-d]pyrimidine-5-$R_3$-6-carbonitrile (FIG. 13c). This product, 2,4-diaminopyrido[2,3-d] pyrimidine-5-$R_3$-6-carbonitrile (FIG. 13c), is then subjected to reductive condensation with an alkyl amine, a substituted aniline or benzylamine derivative containing the $R_2$ group as described herein, such as for example, 3,4,5-trimethoxyaniline, and Raney nickel in aqueous acetic acid solution, and preferably about 70% acetic acid solution, to form 2,4-diamino-5-$R_3$-6-[[($R_2$)amino]methyl]pyrido[2,3-d]pyrimidine (FIG. 13d). The starting material 2-amino-3, 5-dicarbonitrile-4-$R_3$-pyrimidine (FIG. 13a) may be synthesized by those skilled in the art by modifying the method of Piper, et al., J. Med. Chem., Vol. 29, p. 1080 (1986).

These methods further include adding the product represented in FIG. 13d to about 37% formaldehyde in acetonitrile at about 25° C., adding sodium cyanoborohydride, glacial acetic acid and methanol, and refrigerating the reaction mixture overnight to form 2,4-diamino-5-$R_{13}$-6[[($R_2$) methylamino]methyl]pyrido[2,3-d]pyrimidine (FIG. 13e).

2,4-Diamino-5-$R_3$-6[($R_2$)formylamino]methyl]pyrido[2, 3-d]pyrimidine (FIG. 13f) is prepared by reacting the product of FIG. 13d in about 98% formic acid as a solvent and acetic anhydride as a catalyst, removing the solvent under reduced pressure, diluting the reaction product with methanol and refrigerating the diluted reaction product overnight.

2,4-Diamino-5-$R_3$-6[[($R_2$)nitrosoamino]methyl]pyrido[2, 3-d]pyrimidine (FIG. 13g) is prepared by reacting a chilled solution of the product of FIG. 13d in aqueous acetic acid and dimethyl formamide (DMF) and then adding $NaNO_2$ (sodium nitrate) in water. This mixture is stirred at about 0° C. to 5° C. for about two hours and then poured into dilute-sodium hydroxide.

It will be appreciated by those skilled in the art that by following the hereinbefore described methods of preparing the products of FIGS. 13d, 13e, 13f and 13g of this invention that the derivatives of the products of FIGS. 13d, 13e, 13f and 13g can be similarly prepared using the appropriate alkylamine, substituted aniline or benzylamine derivative containing the $R_2$ group as described herein.

Further, a method for preparing 4-amino4-oxo derivatives of the products of FIGS. 13d, 13e, 13f or 13g of this invention includes subjecting these products to hydrolysis with 6N (six-normal solution) HCl for about six hours at room temperature.

Another embodiment of this invention is a method for preparing 2,4-dioxo derivatives of the products of FIGS. 13d, 13e, 13f or 13g that includes subjecting these products to hydrolysis with 6N HCl under mild reflux conditions for about two hours.

Example 17

The following example provides a method for preparing 6-(thiophenylmethyl)-2,4-diaminopyrido[2,3-d]pyrimidine (FIG. 14e) and 6-(thionapthylmethyl)-2,4diaminopyrido[2, 3-d]pyrimidine (FIG. 14f) generally represented by formula 11. Reference letters and numerals correspond with those in FIG. 14.

2,4-diaminopyrido[2,3-d]pyrimidine-6-carboxyaldehyde (FIG. 14b)

About 2.0 g of the nitrile (FIG. 14a) was dissolved in about 60 ml warm $HCO_2H$ under $N_2$. About 10 g of damp Raney Ni was added. The mixture was refluxed for 2 hours and filtered through Celite®. The filtrate was concentrated under reduced pressure at a temperature of 50° C. with the aid of EtOH. The resulting viscous orange residue was then dissolved in about 150 ml of boiling $H_2O$. The boiling solution was treated with Norit® and filtered through Celite® while hot. The filtrate was neutralized to pH 7 with 1 N NaOH to give a yellow precipitate. The suspension was refrigerated overnight, filtered and washed with $H_2O$, EtOH and $Et_2O$ to yield about 1.75 g of a yellow solid. Examination by TLC (4:1:0.1 $CHCl_3$:MeOH:$NH_4OH$) showed a dominant UV-absorbing spot at $R_f$=0.38 and contamination spots at $R_f$=0.19 and at baseline. The spot at $R_f$=0.19 was, after chromatographic separation, determined to correspond to the $R_f$ value of compound (FIG. 14c).

2,4-diaminopyrido[2,3-d]pyrimidine-6methanol (FIG. 14c)

About 5.0 g of crude aldehyde (FIG. 14b) was pulverized, dried and stirred in anhydrous MeOH under $N_2$ overnight. About 0.17 g of $NaBH_4$ was added to the mixture four times at intervals of 15 minutes. The mixture was stirred for 5 additional hours. Insoluble material was filtered and the filtrate was treated with about 200 ml $H_2O$. The filtrate was then concentrated under reduced pressure at a temperature of 35° C. until a yellow precipitate began to form. The mixture was then refrigerated overnight, filtered and rinsed with $H_2O$, EtOH and $Et_2O$ to yield about 1.50 g of a yellow solid. TLC (4:1:0.1 $CHCL_3$:MeOH:$NH_4OH$) showed a product spot at $R_f$=0.41 and a slight spot corresponding to the starting material. Separation was carried out by chromatography with silica gel.

6-(Bromomethyl)-2,4-diaminopyrido[2,3-d]pyrimidine (FIG. 14d)

About 0.24 g of crude alcohol (FIG. 14c) was dried with $P_2O_5$ at 110° C. under vacuum overnight and then added to about 10 ml of anhydrous dioxane. The mixture was stirred in an ice bath while dry HBr gas was bubbled through for 15 minutes, after which the flask was quickly stoppered. The mixture continued to stir and the alcohol dissolved after approximately ½ hour. The solution stirred for 24 hours and was then added dropwise to stirred $Et_2O$ under $N_2$ to give a yellow suspension. The suspension was refrigerated overnight, filtered and immediately dried with $P_2O_5$ under vacuum at 50° C. to yield about 45 mg of the compound represented by FIG. 14d.

6-(Thiophenylmethyl-2,4-diaminopyrido[2,3-d]pyrimidine (FIG. 14e)

About 0.12 ml of phenylthiol was dissolved in about 10 ml DMAC and added dropwise to about 0.25 g of the compound of FIG. 14d. About 1 g of $K_2CO_3$ was added to the mixture to adjust the pH to approximately 8. After 1 hour, the compound of FIG. 14d was not detectable by TLC (3:1:0.1 $CHCl_3$:MeOH:$NH_4OH$). A product spot appeared at $R_f$=0.33 with contamination spots at $R_f$=0.51 and at baseline. The solid was filtered and rinsed with $H_2O$, EtOH and $Et_2O$ to yield about 22 mg of the compound of FIG. 14e.

6-(Thionaphthylmethyl)-2,4-diaminopyrido[2,3-d]pyrimidine (FIG. 14f)

About 0.07 g of napthylenethiol was dissolved in DMAC (15 mL) and added dropwise to about 0.10 g of the compound of FIG. 14d. About 0.3 g of $Na_2CO_3$ was added and the color of the reaction mixture changed from yellow to green. The reaction was monitored by TLC (4:1:0.1 $CHCl_3$:MeOH:$NH_4OH$). A product spot occurred at $R_f$=0.5. After 3 hours, starting material was still present. Also, the yellow color returned. The reaction was run overnight. The pH was then checked and found to be slightly acidic. The solution was added dropwise to about 100 ml of 1 N $Na_2CO_3$. The suspension was stirred for 15 minutes and refrigerated for 4 hours. The solid was filtered and rinsed with $H_2O$, EtOH and $Et_2O$ to yield about 25 mg of the compound of FIG. 14f.

Example 18

The following are various methods for making various 2,4-diamino-6-substituted-benzylamino pyrido[2,3-d] pyrimidines generally represented by formula 11. Reference letters and numerals correspond with those in FIG. 15. The synthesis of the desired compounds is achieved via the reductive amination of 2,4-diamino-6 amino pyrido[2,3-d] pyrimidine 2, with the appropriately substituted aldehyde as generally illustrated in FIG. 15.

Figures 15A, 15B, 15C:
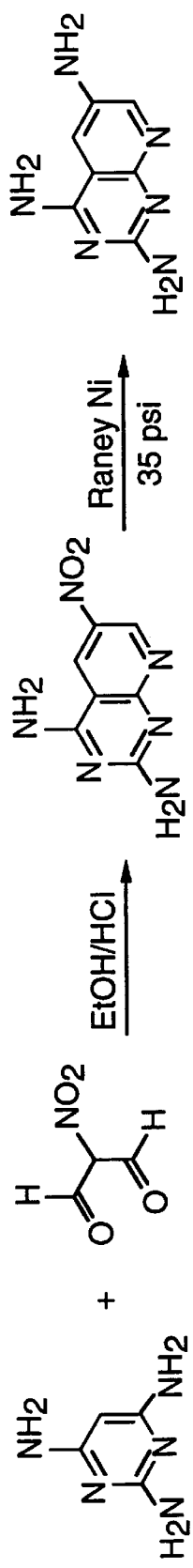
FIG. 15 shows a schematic diagram of the methods of preparing 2,4-diamino-6-substituted-benzylaminopyrido[2,3-d]pyrimidines.

2,4-diamino-6-nitropyrido[2,3-d]pyrimidine (FIG. 15a)

About 1 equivalent of 2,4,6-triamino pyrimidine was suspended in about 50 ml of refluxing absolute ethanol with stirring under an atmosphere of nitrogen. Concentrated HCl was added dropwise to effect solution and as soon as solution occurred, about 1.2 equivalents of nitromalonaldehyde was added all at once. Within 10 minutes, a thick reddish voluminous precipitate started forming. TLC analysis indicated the presence of a yellow spot corresponding to that of the desired product along with staring materials. The reaction mixture was stirred at reflux for 3.5 hours, immediately diluted with 30 ml of water, cooled and neutralized with concentrated $NH_4OH$. The precipitate was collected on a funnel and was washed repeatedly with water to remove unreacted triamino pyrimidine to yield pure 2,4-diamino-6-nitropyrido[2,3-d]pyrimidine.

Example 19

Figure 16A:
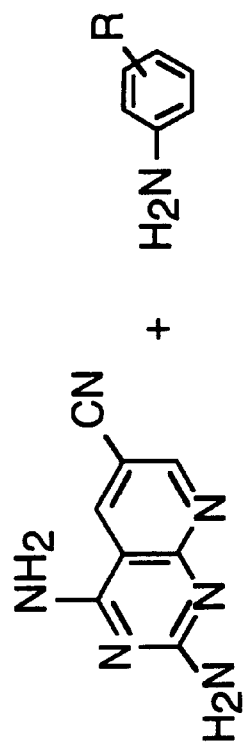
FIG. 16 shows a schematic diagram of the methods of preparing 2,4-diamino-6-(anilinomethyl)pyrido[2,3-d]pyrimidines.

The following is a method of making 2,4-diamino-6-(anilinomethyl) pyrido[2,3-d]pyrimidines generally represented by formula 11. Reference letters and numerals correspond with those in FIG. 16.

Figure 16B:
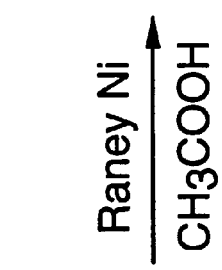
Figure 16C:
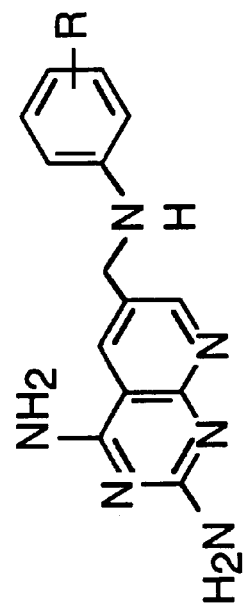

About 1 equivalent of 2,4-diamino-pyrido[2,3-d] pyrimidine-6-carbonitrile (FIG. 16a) (achieved via literature procedures) was dissolved in 80% acetic acid. To this solution was added about 5 equivalents of Raney Nickel followed immediately by about 1.5 equivalents of the appropriately substituted aniline (FIG. 16b). The mixture was hydrogenated under atmospheric pressure and at room temperature for 6 hours. TLC analysis at the end of this period indicated the presence of a spot corresponding to the desired product. The reaction mixture was filtered through Celite® and the filtrate was evaporated to dryness to yield a reddish residue. This residue was dissolved in warm absolute ethanol and then neutralized in the cold with 1 N Na$_2$CO$_3$ dropwise with stirring to deposit the crude product. This solid was collected by filtration and was washed repeatedly with acetone and dissolved in a large volume of methanol; silica gel was added and the methanol stripped off to yield a dry plug. Column chromatography using CHCl$_3$:MeOH (5:1) as the eluant yielded pure target compounds represented by FIG. 16c.

Example 20

The following example provides methods for making pyrido[3,2-d]pyrimidine compounds generally represented by formula 11. Reference letters and numerals correspond with those of FIG. 17.

2,4-dioxo-6-methylpyrido[3,2-d]pyrimidine FIG. 17a)

About 20 g of 5-aminouracil, 80 ml of 20% HCl and 4 ml of crotonaldehyde were heated together under reflux for 1 hour. The solution was evaporated to dryness under rotary evaporation. Water was added to the residue so as to make the mixture just stirrable and then it was triturated with ammonium hydroxide with strong stirring until the pH increased to 10–11. Stirring was continued for another 10 minutes. The precipitate was filtered and was washed with minimal methanol and then chloroform and dried to yield about 17.58 g of the compound of FIG. 17a.

6-(Acetoxymethyl)-2,4-dioxopyrido[3,2-d] pyrimidine (FIG. 17b)

About 1.77 g of the compound of FIG. 17a in 50 ml of glacial acetic acid containing about 6.5 g of MCPBA (57–85%) was refluxed for 3 hours. About 40 ml of acetic anhydride was added to the hot reaction mixture and the refluxing was continued for another 30 minutes. The clear brown solution was evaporated to dryness and the solid was stirred with about 100 ml ether and filtered. The solid was crystallized from ethanol to yield about 1.55 g of the compound of FIG. 17b.

6-(Acetoxymethyl)-2,4-dichloropyrido[3,2-d] pyrimidine (FIG. 17c)

About 1.5 g of the compound of FIG. 17c was refluxed with about 38 mL of phosphoryl chloride containing about 2.5 mL of triethylamine for 8 hours. The volume was reduced to about 5 mL by rotary evaporation. The dark syrup which resulted was poured into crushed ice. The cold suspension was extracted with methylene chloride (3×50 mL) and washed with cold water until the washing were neutral. The organic layer was dried over anhydrous sodium sulfate and evaporated to dryness under rotary evaporation. The dark solid residue was stirred and refluxed with petroleum ether (30–60° C.) and a suitable amount of decoloring charcoal, and filtered through Celite®, which was repeated twice. The combined liquid solution was concentrated until the light yellow solid precipitated out and was allowed to cool to room temperature and stored in a refrigerator for 2 hours. The crystallized solid was filtered and dried to yield about 0.86 g of the compound of FIG. 17c.

2,4-diamino-6-(hydroxymethyl)pyrido[3,2-d] pyrimidine (FIG. 17d)

About 2.5 g of the compound of FIG. 17c was heated with 30 mL of liquid ammonia in a sealed bomb at between about 150–170° C. for 18 hours. After cooling to room temperature, the bomb was opened and the liquid ammonia was allowed to evaporate at room temperature. The solid was crystallized from glacial acetic acid and a small amount of water to yield about 1.24 g of the compound of FIG. 17d.

2,4-diamino-6-(bromomethyl)pyrido[3,2-d] pyrimidine (FIG. 17e)

A suspension of about 0.72 g of the compound of FIG. 17d in 12 mL dry THF was stirred for 8 hours with 1 mL of phosphorus tribromide. The precipitated solid was filtered, washed with cold 50% THF-Ether, and dried to give the compound of FIG. 17e. Because of the instability, this compound was not purified further. The $^1$HNMR showed that the majority of the solid was the desired compound.

2,4-diamino-6-(paramethoxyanilinylmethyl)pyrido [3,2-d]pyrimidine (FIG. 17f)

To a suspension of about 3.5 mmol of the compound of FIG. 17e in anhydrous dimethylacetamide was added 0.92 g anisidine and 1.03 g anhydrous potassium. After the suspension was stirred for 2 days, almost all of the compound of FIG. 17e disappeared. The solvent DMAC was removed under diminished pressure. The solid residue was washed with methanol three times and filtered. To the combined liquid was added silica gel and the methanol was evaporated to dryness. Separation to afford pure product of FIG. 17f was carried out by column chromatography.

2,4-diamino-6-(phenylthiomethyl)pyrido[3,2-d] pyrimidine (FIG. 17g)

To a suspension of about 2.5 mmol of the compound of FIG. 17g in anhydrous dimethylacetamide was added 1 mL thiophenol and 690 mg anhydrous potassium. The suspension was stirred for 3 days. The solvent DMAC was removed under diminished pressure. The solid residue was washed with methanol three times and filtered. The combined liquid was added to silica gel and then the methanol was evaporated to dryness. A small amount of product was separated through a dry column. After crystallization, about 5 mg of pure product of FIG. 17g was obtained.

2,4-diamino-6-(naphathalinylmethyl)pyrido[3,2-d] pyrimidine (FIG. 17h)

The procedure for making the compound of FIG. 17f was repeated with a reaction time of 5 days to yield the compound of FIG. 17h.

Example 21

The following example provides methods for making the tricyclic pyrimidine compounds generally represented by formula 10. Reference letters and numerals correspond with those of FIG. 10.

N-butoxycarbonyl4-piperidone (FIG. 10b)

About 2 g of 4-piperidone hydrochloride monohydrate (FIG. 10a) was dissolved in about 30 ml of N,N-dimethylformamide at temperatures of between about 110–1 15° C. The solution was cooled to room temperature, and to this solution was added about 2.6 g of triethyl amine and a solution containing about 3.06 g of ditertiarybutyl dicarbonate in 10 ml DMF. The reaction was continued for about 24 hours at room temperature. The DMF was removed under reduced pressure. About 100 ml of water was added to the residue and the mixture was extracted with ethyl ether (2×100 ml), and the organic layer dried over anhydrous MgSO$_4$. The ether was evaporated to dryness under reduced pressure to yield about 2.33 g of the compound of FIG. 10b.

3-bromo-4-piperidone hydrobromide (FIG. 10c)

About 2.6 g of N-butoxycarbonyl-4-piperdone (FIG. 10b) was dissolved in about 70 ml of chloroform; to this solution was added about 2.08 g Br$_2$ over a period of about 30 minutes. The reaction was continued for about 2 hours at room temperature during which a white precipitate of the compound of FIG. 10c was formed. The reaction mixture was filtered and washed with chloroform ether to yield about 2.76 g of the compound of FIG. 10c.

2,4-diamino-5,6,7,8-tetrahydro-7-pyrido[4',3':4.5]furo[2,3-d]pyrimidine hydrobromide (FIG. 10f)

A solution containing about 1.83 g of the compound of FIG. 10c in about 10 ml of anhydrous DMF was added dropwise to a suspension containing about 0.504 g of 2,4-diamino-6-hydroxypyrimidine in about 3 ml of anhydrous DMF. The reaction became a clear solution after about 1 hour; the solution was then left at room temperature for about 48 hours. The white precipitate which formed was collected by filitration and air dried to yield about 0.66 g of the compound of FIG. 10f.

2,4-diamino-5,6,7,8-tetrahydro-(7-butoxycarbonyl)pyrido[4',3':4,5]furo [2,3-d]pyrimidine hydrobromide (FIG. 10e)

The filtrate obtained in preparing the compound of FIG. 10c was diluted with about 150 ml of chloroform and washed with water, saturated sodium bicarbonate and brine. The organic layer was dried over anhydrous MgSO$_4$, and the chloroform was removed under reduced pressure to yield a viscous brown oil. The residue was dissolved immediately in about 5 ml of anhydrous DMF, and added to a suspension containing about 0.252 g of 2,4-diamino-6-hydroxypyrimidine in anhydrous DMF. The reaction was continued for about 48 hours at room temperature. The DMF was removed under reduced pressure, and the residue was dissolved in 50 ml of methanol; about 1.7 g of silica gel was added and the mixture was evaporated to dryness under reduced pressure. About 50 ml of ether was added to the silica gel plug; the homogenous plug collected after filtration was air-dried and then placed on top of a dry silica gel column (1.5 cm×10 cm) and gradiantly eluted with MEOH in CHCl$_3$. Fractions containing the compound of FIG. 10e were pooled and evaporated to dryness under reduced pressure to yield 0.025 g of the compound.

2,4-diamino-5,6,7,8-tetrahydro-7-(benzyl)pyrido[4',3':4,5]furo[2,3-d]pyrimidine (FIG. 10g)

About 0.46 g of the compound of FIG. 10f was suspended in 5 ml of anhydrous DMSO. About 0.483 g of anhydrous potassium carbonate and 0.24 g of benzyl bromide were added to the suspension; the reaction was continued for 24 hours at room temperature. The mixture was then diluted with about 30 ml of water and stirred for 24 hours at room temperature. The resulting precipitate was collected by filtration, washed with water, acetone, ether and air-dried. The crude solid was dissolved in a mixture of DMF:MeOH (1:5); about 1.2 g of silica gel was added and the mixture was evaporated to dryness under reduced pressure. The resulting silica gel plug was placed on a top of a dry silica gel column (1.5 cm×10 cm) and gradiantly eluted with MeOH in CHCl$_3$. The fractions containing the compound of FIG. 10g were pooled and evaporated to dryness under reduced pressure; the resulting solid was triturated with ether and filtered to yield about 0.156 g of product.

2,4-diamino-5,6,7,8-tetrahydro-7-[(3',4',5'-trimethoxy)benzyl]pyrido[4',3',:4,5]furo[2,3-d]pyrimide (FIG. 10h)

The compound of FIG. 10h was prepared and purified in the same manner as the compound of FIG. 10g, only using 3',4',5'-trimethoxybenzyl chloride instead of benzyl bromide to yield about 0.12 g of the compound of FIG. 10h as a yellow solid.

2,4-diamino-5,6,7,8-tetrahydro-7-[(3',5'-dimethoxy)benzyl]pyrido[4',3':4,5]furo[2,3-d]pyrimide (FIG. 10i)

The compound of FIG. 10i was prepared and purified in the same manner as the compound of FIG. 10g, only using 3',5'-dimethoxybenzyl chloride instead of benzyl bromide to yield about 0.126 g of the compound of FIG. 10i.

2,4-diamino-5,6,7,8-tetrahydro-7-[(2',4'-dichloro)benzyl]pyrido[4',3':4,5]furo[2,3-d]pyrimide (FIG. 10i)

The compound of FIG. 10j was prepared and purified in the same manner as the compound of FIG. 10g, only using 2',4'-dichlorobenzyl chloride instead of benzyl bromide to yield about 0.151 g of the compound of FIG. 10j.

2,4-diamino-5,6,7,8-tetrahydro-7-[(3',4'-dichloro)benzyl]pyrido[4',3':4,5]furo[2,3-d]pyrimide (FIG. 10k)

The compound of FIG. 10k was prepared and purified in the same manner as the compound of FIG. 10g, only using 3',4'-dichlorobenzyl chloride instead of benzyl bromide to yield about 0.131 g of the compound of FIG. 10k.

2,4-diamino-5,6,7,8-tetrahydro-7-[(2',6'-dichloro)benzyl]pyrido[4',3':4,5]furo[2,3-d]pyrimide (FIG. 10l)

The compound of FIG. 10l was prepared and purified in the same manner as the compound of FIG. 10g, only using 2',6'-dichlorobenzyl chloride instead of benzyl bromide to yield about 0.093 g of the compound of FIG. 10l.

2,4-diamino-5,6,7,8-tetrahydro-7-[(2',4'-dichloro)benzyl]pyrido[4',3':4,5]furo[2,3-d]pyrimide (FIG. 10m)

2,4-Diamino-5,6,7,8-tetrahydro-7-[(4"-benzoyl)diethyl-L-glutamic acid)]pyrido[4',3':4,5]furo[2,3-d]pyrimidine was prepared and purified in the same manner as the compound of FIG. 10g, only using 4'-(chloromethyl)benzoyl glutamic acid diethyl ester instead of benzyl bromide. About 1.5 ml of 1 N NaOH was added to a solution containing about 0.183 g of this compound in 10 ml methoxyethanol, and the solution stirred at room temperature for about 24 hours. The ethoxyethanol was evaporated under reduced pressure, the residue was dissolved in about 10 ml of water and stirring continued for an additional 24 hours. The solution was cooled in an ice bath and the pH was adjusted to about 3.5 via dropwise addition of 1 N HCl. The precipitate formed was collected by filtration, washed with water, acetone and ether and air-dried to obtain about 0.160 g of the compound of FIG. 10m.

Example 22

The compound of FIG. 10m was tested for DHFR inhibition, as discussed above in Example I, against *Pneumocystis carinii* (Pc), *Toxoplasmosis gondii* (Tg), *Macrobacterium avium* (Ma) and rat liver (RL). Ma is an opportunistic infection in HIV infected patients. Table 17 sets forth the $IC_{50}$ values.

TABLE 17

Inihibitory Concentrations ($IC_{50}$, microM) and Selectivity Ratios

| Compound | Pc | Tg | RL | RL/Pc | RL/Tg | M. avium |
|---|---|---|---|---|---|---|
| 10m | 10.9 | 21.5 | 85.8 | 7.9 | 4 | 0.97 |

The compound of FIG. 10m showed a weak inhibitory activity against DHFR, but displayed promising selectivity ratios of 7.9 and 4 against Pc DHFR and Tg DHFR, respectively, against RL DHFR. In addition, compound 10 m showed significant inhibitory activity against Ma DHFR and had a selectivity ratio of 88 versus RL DHFR.

In addition, the ability of the compound of FIG. 10m to function as a substrate of human CCRF-CEM folylpolyglutamate synthetase was assessed, as discussed above in Example 4. Results are presented in Table 18.

TABLE 18

Activity of the Compound of Figure 10m as Substrate for CCRF-CEM Human Leukemia Cell Folylpolyglutamate Synthetase

| substrate | $K_m$, microM | $V_{max,rel}$ | $V_{max}/K_{m(rel)}$ | n |
|---|---|---|---|---|
| Aminopterin | 4.8 ± 0.7 | 1 | 0.21 ± 0.04 | 6 |
| 10m | 6.2 ± 1.4 | 0.29 ± 0.05 | 0.06 ± 0.01 | 2 |

Example 23

The following example provides methods for making pyrido[3,2-d]pyrimidine compounds generally represented by formula 11. Reference letters and numerals correspond with those of FIG. 11.

Figure 11A:
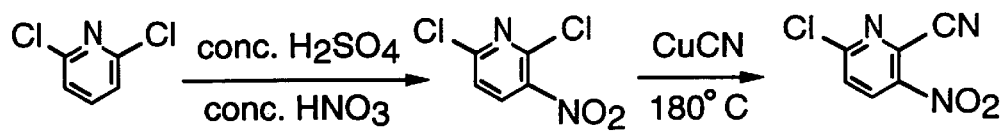
FIG. 11 shows a schematic diagram of the methods of preparing pyrido[3,2-d]pyrimidines.
Figures 11B, 11C:
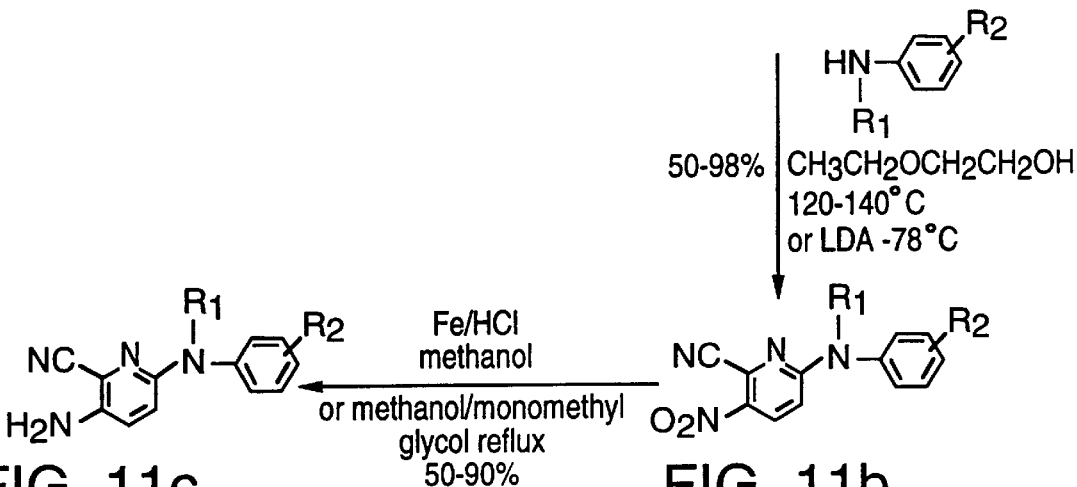
Figure 11D:
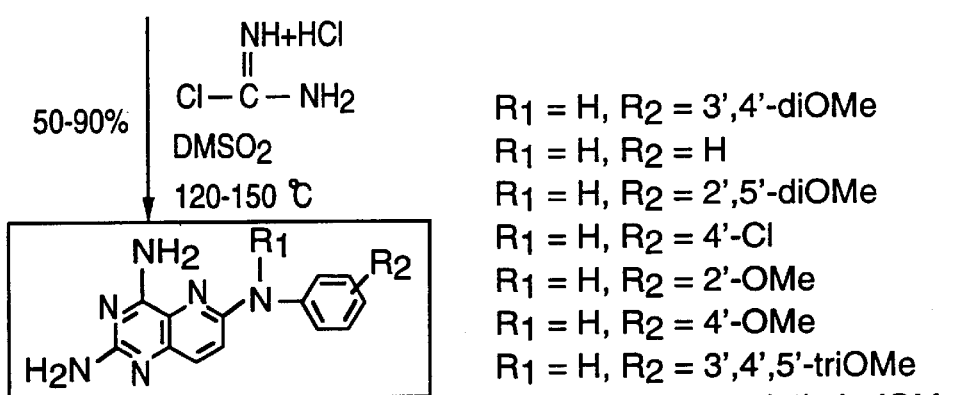

The compound of FIG. 11a was synthesized from 2,6-dichloropyridine in two steps—nitration at the 3 position with concentrated sulfuric acid and 90% nitric acid, followed by substitution of the 2-chloro moiety with a cyano group using CuCN at 180° C. The compound of FIG. 11b was synthesized via a direct aromatic substitution of FIG. 11a with arylamines, 3',4',5'-trimethoxybenzylamine, or N-methylarylamines in 2 ethoxyethanol at temperatures between about 120–140° C. The compound of FIG. 11b was then reduced by iron in acidic conditions under reflux in methanol to yield the intermediate 2-cyano-3-amino-6-substituted pyridines (FIG. 11c). Monomethylglycol was added to increase the solubility. The compound of FIG. 11c was condensed with formamidine hydrochloride in dimethyl sulfone at temperatures between about 120 and 150° C. to provide the compound of FIG. 11d.

Example 24

The following example provides methods for making pyrido[3,2-d]pyrimidine compounds generally represented by formula 11. Reference letters and numerals correspond with those of FIG. 12.

The compound of FIG. 12a was reduced with iron powder, followed by condensation with chlorohydrochloride in DMSO at temperatures of between about 120 and 150° C. to yield 2,4-diamino-6chloro-pyrido[3,2-d]pyrimidine (FIG. 12c). The compound of FIG. 12c was subjected to a substitution reaction with substituted thiophenols, to yield three arylthiol compounds (FIGS. 12f, 12g, and 12h) generally represented by FIG. 12d. The oxidation of these compounds with hydrogen peroxide in acetic acid provided three corresponding sulfonyl compounds with the general structure represented by FIG. 12e.

Example 25

The following example provides methods for making pyrido[3,2-d]pyrimidine compounds generally represented by formula 11. Reference letters and numerals correspond with those of FIG. 18.

The compound of FIG. 18a was prepared from 2,6-dichloropyridine by methods known in the art. The 3-amino group of the compound of FIG. 18a was protected with an acetyl group by reacting the compound with acetyl anhydride and triethylamine in the presence of DMAP under reflux conditions in methylene chloride for 20 hours. Part of the starting material was converted to the N,N-diacetylated amino derivative, which was in turn converted in situ into the compound of FIG. 18b when stirred in a saturated sodium bicarbonate solution at room temperature for about 1.5 hours. The compound of FIG. 18b was then oxidated with trifluroperacetic acid in methylene chloride at room temperature for 24 hours to yield the compound of FIG. 18c, 2-amidylpyridine-N-oxide. The compound of FIG. 18c was then heated at about 140° C. with a guanidine carbonate base in 2-ethoxyethanol for about one hour to yield the compound of FIG. 18d, 6chloro-2-methyl4-oxo-pyrido[3,2-d]pyrimidine. The compound of FIG. 18d was then reacted with the sodium salt of p-thiocresol in anhydrous DMF at 125° C. to yield the pyrido[3,2-d]pyrimidine compound of FIG. 18e.

Any compatible sulfur, oxygen or nitrogen containing nucleophile can be reacted with the compound of FIG. 18d to yield the corresponding pyrido[3,2-d]pyrimidine compound.

It will be appreciated by those skilled in the art that the present invention provides compounds, and pharmaceutically acceptable salts thereof, effective against infections caused by *Pneumocystis carinii* and *Toxoplasmosis gondii*, methods of preparing these compounds, and methods of using these compounds in a patient for therapeutic or prophylactic purposes. It will be further appreciated by those skilled in the art that this invention provides compounds, and pharmaceutically acceptable salts thereof, effective in reducing tumors or otherwise destroying cancerous cells in patients with cancer, methods of preparing these compounds, and methods of using these compounds in a patient for therapeutic purposes.

Whereas particular embodiments of this invention have been described above for purposes of illustration, it will be evident to those skilled in the art that numerous variations of the details of the present invention may be made without departing from the invention as defined in the appended claims.

What is claimed is:

1. A method of therapeutically treating a patient for an illness comprising the steps of:

a) employing a compound, or pharmaceutically acceptable salts thereof, having the formula:

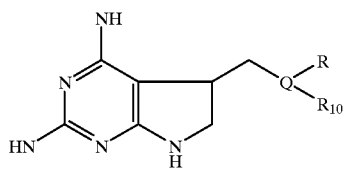

(9)

wherein Q is selected from the group consisting of nitrogen and sulfur;

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyl diaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen;

wherein $R_{10}$ is selected from the group consisting of hydrogen and a lower alkyl group; and wherein $R_{10}$ is a lower alkyl group when Q is nitrogen; and wherein each lower alkyl group is independently selected from the group consisting of lower alkyl groups having from 1 to 6 carbons;

b) incorporating said compound in a suitable pharmaceutical carrier; and c) administering a therapeutically effective amount of said compound incorporated in said carrier to a patient.

2. The method of claim 1, wherein said illness is cancer.

3. The method of claim 1, wherein said illness is selected from the group consisting of infection caused by *Pneumocystis carinii* and *Toxoplasmosis gondii*.

4. The method of claim 1, wherein said carrier is selected from the group consisting of physiologic saline and 5% dextrose for injection.

5. The method of claim 1, including administering said compound incorporated in said carrier to a patient parenterally.

6. The method of claim 1, including administering said compound incorporated in said carrier to a patient orally.

7. The method of claim 1, including administering said compound incorporated in said carrier to a patient topically.

8. A method of prophylactically treating a patient for an illness comprising the steps of:

a) employing a compound, or pharmaceutically acceptable salts thereof, having the formula:

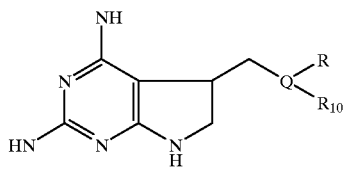

(9)

wherein Q is selected from the group consisting of nitrogen and sulfur;

wherein R is selected from the group consisting of a lower alkyl group, a p-aroyl-L-plutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen;

wherein $R_{10}$ is selected from the group consisting of hydrogen and a lower alkyl group; and wherein $R_{10}$ is a lower alkyl group when Q is nitrogen; and wherein each lower alkyl group is independently selected from the group consisting of lower alkyl groups having from 1 to 6 carbons;

b) incorporating said compound in a suitable pharmaceutical carrier; and c) administering a prophylactically effective amount of said compound incorporated in said carrier to a patient; wherein said illness is selected from the group consisting of infection caused by *Pneumocystis carinii* and *Toxoplasmosis gondii*.

9. The method of claim 8, wherein said carrier is selected from the group consisting of physiologic saline and 5% dextrose for injection.

10. The method of claim 8, including administering said compound incorporated in said carrier to a patient parenterally.

11. The method of claim 8, including administering said compound incorporated in said carrier to a patient orally.

12. The method of claim 8, including administering said compound incorporated in said carrier to a patient topically.

* * * * *

UNITED STATES PATENT AND TRADEMARK OFFICE
CERTIFICATE OF CORRECTION

PATENT NO.   : 6,103,727
DATED        : August 15, 2000
INVENTOR(S)  : Aleem Gangjee It is certified that error appears in the above-identified patent and that said Letters Patent is hereby corrected as shown below:

Title page,
*Assistant Examiner's* name should read -- Pavanaram K. Sripada --.

Column 1,
Line 37, "*Pnewnocystis*" should read -- *Pneumocystis* --.

Column 2,
Line 25, "6-Keto Esters" should read -- 6-Keto Esters --.
Line 32, "[2,34pyrimidines." should read -- [2,3-*d*]pyrimidines. --.
Line 41, "2,5Sdimewthoxybenzyl)" should read -- 2,5-dimethoxybenzyl) --.

Column 3,
Line 13, "*Pnewnocystis*" should read -- *Pneumocystis* --.

Column 4,
Line 40, "[2,3d]" should read -- [2,3-*d*] --.

Column 7,
Line 23, "[3,24d]" should read -- [3,2-*d*] --.

Column 11,
Line 24, "Z, is $R_4$" should read -- $Z_1$ is $R_4$ --.
Line 35, "$R_2$" should read -- $R_1$ --.
Line 66, "[3,4-d]" should read -- [2,3-*d*] --.

Column 12,
Line 41, after "sulfur", insert -- sulfoxide --.
Line 51, "alkyldiaryi" should read -- alkyldiaryl --.

Column 15,
Line 20, "*Pnewnocystis*" should read -- *Pneumocystis* --.

Column 16,
Line 20, "wherein Z" should read -- wherein $Z_2$ --.

Column 19,
Line 65, "diethylip-aminoaroyl)" should read -- diethyl(*p*-aminoaroyl) --.

Column 32,
Line 11, "[2,3-]" should read, -- [2,3*d*] --.

UNITED STATES PATENT AND TRADEMARK OFFICE
CERTIFICATE OF CORRECTION

PATENT NO. : 6,103,727
DATED : August 15, 2000
INVENTOR(S) : Aleem Gangjee

It is certified that error appears in the above-identified patent and that said Letters Patent is hereby corrected as shown below:

Column 32,
Line 11, "[2,3-]" should read, -- [2,3$d$] --.

Column 33,
Line 4, "groug" should read -- group --.

Column 34,
Line 33, "2,4,6trifluorophenyl" should read -- 2,4,6-trifluorophenyl --.

Column 37,
Line 61, "NMX" should read -- MTX --.

Column 38,
Line 20, "MiX" should read -- MTX --.
Table 7, 3$^{rd}$ and 4$^{th}$ column, title reads "$V_{max,\ red}$" and "$V_{max}/K_{m(red)}$", the titles should read -- $V_{max,\ rel}$ and "$V_{max}/K_{m(rel)}$ --.

Column 40,
Line 39, "T47D" should read -- T-47D --.

Column 43,
Line 17, "010" should read -- 0.10 --.
Line 25, "3,4-dimethokyaniline", should read -- 3,4-dimethoxyaniline --.
Line 42, "dimethoxvanilino" should read -- dimethoxyanilino --.
Line 51, "iminol" should read -- imino] --.

Column 44,
Line 10, "methylpyrrolo" should read -- methyl]pyrrolo --.

Column 45,
Line 47, "-ethanvl]benzoate(27)" should read -- -ethanyl]benzoate(27) --.
Line 51, "[2,3-]" should read, -- [2,3-$d$] --.

Column 46,
Line 18, "2,3pyrimidin-5yl)" should read -- [2,3-$d$]pyrimidin-5-yl) --.
Line 31, "(2.4x1cm)" should read -- (2.4x16cm) --.

Column 48,
Line 19, "methylllenzoyl)" should read -- methyl(benzoyl) --.
Line 42, "[2,3-dipyrimidin" should read -- [2,3-$d$]pyrimidin- --.
Line 63, eliminate the -- period (.) -- after "CCRF-CEM".

UNITED STATES PATENT AND TRADEMARK OFFICE
CERTIFICATE OF CORRECTION

PATENT NO.    : 6,103,727
DATED         : August 15, 2000
INVENTOR(S)   : Aleem Gangjee It is certified that error appears in the above-identified patent and that said Letters Patent is hereby corrected as shown below:

Column 50,
Line 5, "5-R$_3$" should read, -- 5-R$_{13}$ --.
Line 17, "5-R$_3$-6[(R$_2$)" should read -- 5-R$_3$-6[[(R$_2$) --.
Line 36, "4-amino4" should read -- 4-amino-4 --.

Column 51,
Line 25, "6methanol" should read -- 6-methanol --.

Column 53,
Line 62, "(hvdroxymethyl)" should read -- (hydroxymethyl) --.

Column 54,
Line 56, "N-butoxycarbony14-piperidone" should read -- N-butoxycarbonyl-4-piperidone --.

Column 55,
Line 47, "MEOH" should read -- MeOH --.

Column 56,
Line 25, "10i" should read -- 10$j$ --

Column 58,
Line 2, "6chloro-pyrido" should read -- 6-chloro-pyrido --.
Line 33, "methy14-oxy" should read, -- methyl-4-oxy --.

UNITED STATES PATENT AND TRADEMARK OFFICE
CERTIFICATE OF CORRECTION

PATENT NO. : 6,103,727
DATED : August 15, 2000
INVENTOR(S) : Aleem Gangjee

It is certified that error appears in the above-identified patent and that said Letters Patent is hereby corrected as shown below:

<u>Column 60,</u>
Line 16, "plutamate" should read --glutamate --.

Signed and Sealed this

Twenty-seventh Day of August, 2002

*Attest:*

JAMES E. ROGAN
*Attesting Officer          Director of the United States Patent and Trademark Office*